(12) United States Patent
Devaux et al.

(10) Patent No.: US 7,435,416 B2
(45) Date of Patent: Oct. 14, 2008

(54) ANTI-TUMOR ANTIBODY COMPOSITIONS AND METHODS OF USE

(75) Inventors: Brigitte Devaux, Palo Alto, CA (US); Gilbert-Andre Keller, Belmont, CA (US); Hartmut Koeppen, Berkeley, CA (US); Lawrence A. Lasky, Sausalito, CA (US)

(73) Assignee: Genetech, Inc., South San Francisco, CA (US)

( * ) Notice: Subject to any disclaimer, the term of this patent is extended or adjusted under 35 U.S.C. 154(b) by 260 days.

(21) Appl. No.: 10/937,046

(22) Filed: Sep. 8, 2004

(65) Prior Publication Data

US 2005/0036942 A1 Feb. 17, 2005

Related U.S. Application Data

(62) Division of application No. 09/698,705, filed on Oct. 27, 2000, now Pat. No. 6,824,780.

(60) Provisional application No. 60/162,558, filed on Oct. 29, 1999, provisional application No. 60/182,872, filed on Feb. 16, 2000.

(51) Int. Cl.
A61K 39/395 (2006.01)

(52) U.S. Cl. .................................. 424/156.1; 530/388.1

(58) Field of Classification Search ........................ None
See application file for complete search history.

(56) References Cited

U.S. PATENT DOCUMENTS

| | | | |
|---|---|---|---|
| 5,208,020 A | 5/1993 | Chari et al. | |
| 5,416,064 A | 5/1995 | Chari et al. | |
| 5,648,237 A | 7/1997 | Carter | |
| 5,789,199 A | 8/1998 | Joly et al. | |
| 5,840,523 A | 11/1998 | Simmons et al. | |
| 5,856,136 A | 1/1999 | Au-Young | |
| 6,756,036 B2 * | 6/2004 | Reiter et al. | 424/156.1 |

FOREIGN PATENT DOCUMENTS

| | | |
|---|---|---|
| CA | 2351887 | 6/2000 |
| CA | 2378946 | 1/2001 |
| EP | 425235 B1 | 9/1996 |
| WO | WO 98/00540 | 1/1998 |
| WO | WO 98/40403 * | 9/1998 |
| WO | WO 98/51805 | 11/1998 |
| WO | WO 98/51824 | 11/1998 |
| WO | WO 99/14328 | 3/1999 |
| WO | WO 00/32752 | 6/2000 |
| WO | WO 01/05427 A1 | 1/2001 |

OTHER PUBLICATIONS

Little et al., "Of Mice and Men: Hybridoma and Recombinant Antibodies." *Immunology Today* 21(8):364-370 (Aug. 2000).
Amara et al., "Monoclonal antibodies against prostate stem cell antigen inhibit prostate cancer tumour formation in SCID mice" *Eur. Urol.* (Abstract No. 420) 37(suppl 2):105 (2000).
Bahrenberg et al., "Reduced Expression of PSCA, a Member of the LY-6 Family of Cell Surface Antigens, in Bladder, Esophagus, and Stomach Tumors" *Biochemical and Biophysical Research Communications* 275:783-788 (2000).
Dannull et al., "Prostate Stem Cell Antigen Is a Promising Candidate for Immunotherapy of Advanced Prostate Cancer" *Cancer Research* 60:5222-5528 (2000).
Gingrich et al., "Pathologic Progression of Autochthonous Prostate Cancer in the TRAMP Model." *Prostate Cancer and Prostatic Diseases.* 2:70-75 (1999).
Greenberg et al., "Prostate Cancer in a Transgenic Mouse." *Proc. Natl. Acad. Sci. USA* 92:3439-3443 (1995).
Gu et al., "Prostate stem cell antigen (PSCA) expression increases with high gleason score, advanced stage and bone metastasis in prostate cancer" *Oncogene* 19:1288-1296 (2000).
Liu et al., "Eradication of Large Colon Tumor Xenografts by Targeted Delivery of Maytansinoids." *Proc. Natl. Acad. Sci. USA* 93:8618-8623 (Aug. 1996).
Reiter et al., "Prostate stem cell antigen: a cell surface marker overexpressed in prostate cancer" *Proc. Natl. Acad. Sci. USA* 95(4):1735-1740 (Feb. 17, 1998).
Saffran et al., "Anti-PSCA mABs inhibit tumor growth and metastasis formation and prolong the survival of mice bearing human prostate cancer xenografts" *Proc. Natl. Acad. Sci. USA* 98(5):2658-2663 (2001).

* cited by examiner

*Primary Examiner*—Misook Yu
(74) *Attorney, Agent, or Firm*—Lee K. Tan

(57) ABSTRACT

The invention provides antibodies targeted at a tumor antigen prevalent on prostate tumors and methods useful in alleviating cancers expressing the antigen, as well as nucleic acids and cells for expressing the antibodies.

7 Claims, 18 Drawing Sheets

HEAVY CHAIN SEQUENCES OF ANTI-PSCA MAbs

```
                              CDR1                                              CDR2
2395 : N---------ELVKPGAPVKLSCKASGYTFTNYWMNWVKQRPGRGLEWIGRIDPSXXXTXXXQTFKDKA
2399 : N---------PGAELVKPGAPVKLSCKASGYTFTNYWMNWVKQRPGRGLEWIGRIDPSDSETQYNQTFKDKA
2403 : N-QVQVQQPGAELVKPGAPVKLSCKASGYTFTNYWLNWVKQRPGRGLEWIGRIDPSDSEIHYDQKFKDKA
2761 : N-EVQLQQSGPDLEKPGASVKISCKPSGNSFTGYYIHWVKQSHGKSLEWIGRVDPNNGFTSYNQKFKGKA

CDR3
2395 : TLTVDKSSSTAYIQLSSLTSEDSAVYYCAITAAIAMDYWGQGTSVTVSSAKTTGPS-C
2399 : TLTVDKSSSTAYIQLSSLTSEDSAVYYCAITAAIAMDYWGQGTSVTVSSAKTTGPS-C
2403 : TLTVDKSSSTAYIQLSSLTSEDSAVYYCALTGIYAMAYWGQGTSVTVSSAKTTGPS-C
2761 : ILTVDKSSSTAYMELRSLTSEDSAVYYCVG-NFFDS--WGQGTTLTVSSAKTTGPS-C
```

LIGHT CHAIN SEQUENCES OF ANTI-PSCA MAbs

```
                              CDR1                                              CDR2
2395 : N--------------SVSISCRSSKSLLHSNGNTYLYLYWFLQRPGQSPQLLIYRMSNLASGVPDRFS
2403 : N-DIVMTQAAPSVPVTPGESVSISCRSSKSLLHSNGNTYLYLYWFLQRPGQSPQLLIYRMSNLASGVPDRFS
2761 : N-DVVMTQTPLTLSVTIGQPASISCKSSQSLLDSDGKTYLNWLLQRPGQSPKRLIYLVSTLDSGVPDRFT

CDR3
2395 : GSGSGTVFTLRISRVEAAEDVGVYYCMQHLESPFTFGSGTKLEIKR-C
2403 : GSGSGTAFTLRISRVEAAEDVGVYYCLQHLEYPYTFGGGTKLELKR-C
2761 : GSGSGTDFTLKISRVEAEDLGVYYCWQGTHFPRTFGGGTKLEIKR-C
```

FIG. 12 chimeric 2403 (5F2.4H4.1E3) Light Chain
signal peptide MGWSCIILFLVATATGVHS
DIVMTQAAPSVPVTPGESVSISCRSSKSLLHSNGNTYLYWFLQRPGQSPQLLIYRMSNLASGVPDRFSGSGSGTAFTLRISRVEAEDVG
VYYCLQHLEYPYTFGGGTKLELK/RTVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC chimeric 2403 (5F2.4H4.1E3) IgG Heavy Chain
signal peptide MGWSCIILFLVATATGVHS
QVQVQQPGAELVKPGAPVKLSCKASGYTFTNYWLNWVKQRPGRGLEWIGRIDPSDSEIHYDQKFKDKATLTVDKSSSTAYIQLSSLT
SEDSAVYYCALTGIYAMAYWGQGTSVTVSSAKTTG/PSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSRWQQGNVFSCSVMHEALHNHYT
QKSLSLSPGK chimeric 2761 (6B8.1D7.2B3) Fab - Light Chain
DVVMTQTPLTLSVTIGQPASISCKSSQSLLDSDGKTYLNWLLQRPGQSPKRLIYLVSTLDSGVPDRFTGSGSGTDFTLKISRVEAEDLGV
YYCWQGTHFPRTFGGGTKLEIKR [VL/Cκ junction]
TVAAPSVFIFPPSDEQLKSGTASVVCLLNNFYPREAKVQWKVDNALQSGNSQESVTEQDSKDSTYSLSSTLTLSKADYEKHKVYACET
HQGLSSPVTKSFNRGEC chimeric 2761 (6B8.1D7.2B3) Fab - Heavy chain
EVQLQQSGPDLEKPGASVKISCKPSGNSFTGYYIHWVKQSHGKSLEWIGRVDPNNGFTSYNQKFKGKAILTVDKSSSTAYMELRSLTSE
DSAVYYCVGNFFDSWGQGTTLTVSSA [VH/Cγ1 junction]
KTTGPSVFPLAPSSKSTSGGTAALGCLVKDYFPEPVTVSWNSGALTSGVHTFPAVLQSSGLYSLSSVVTVPSSSLGTQTYICNVNHKPSN
TKVDKKVEPKSCDKTHT

FIG. 13

```
  1 ATGAAGGCTG TGCTGCTTGC CCTGTTGATG GCAGGCTTGG CCCTGCAGCC AGGCACTGCC
    TACTTCCGAC ACGACGAACG GGACAACTAC CGTCCGAACC GGGACGTCGG TCCGTGACGG
  1 M  K  A  V    L  L  A    L  L  M    A  G  L    A  L  Q  P    G  T  A

61 CTGCTGTGCT ACTCCTGCAA GGCCCAGGTG AGCAACGAGG ACTGCCTGAA TGTGGAGAAC
    GACGACACGA TGAGGACGTT CCGGGTCCAC TCGTTGCTCC TGACGGACTT ACACCTCTTG
 21 L  L  C  Y    S  C  K    A  Q  V    S  N  E  D    C  L  N    V  E  N

121 TGCACGCAGC CGGAGGAGCA GTGCTGGACC GAGCGCATCC GCGCCGTGGG CCTCCTGACC
    ACGTGCGTCG GCCTCCTCGT CACGACCTGG CTCGCGTAGG CGCGGCACCC GGAGGACTGG
 41 C  T  Q  P    E  E  Q    C  W  T    E  R  I  R    A  V  G    L  L  T

181 GTCATCAGCA AAGGCTGCAG CTCAAACTGC GTGGATGACT CACAGGACTA CTACGTGGGC
    CAGTAGTCGT TTCCGACGTC GAGTTTGACG CACCTACTGA GTGTCCTGAT GATGCACCCG
 61 V  I  S  K    G  C  S    S  N  C    V  D  D  S    Q  D  Y    Y  V  G

241 AAGAAGAACA TCACCTGCTG TGACACCGAC TTGTGCAACG CCAGCGGGGC CCATGCACTG
    TTCTTCTTGT AGTGGACGAC ACTGTGGCTG AACACGTTGC GGTCGCCCCG GGTACGTGAC
 81 K  K  N  I    T  C  C    D  T  D    L  C  N  A    S  G  A    H  A  L

301 CAGCCGGCTG CTGCCATCCT GGCACTGCTC CCTGCACTCA GTCTGCTGCT TTGGAGCCCC
    GTCGGCCGAC GACGGTAGGA CCGTGACGAG GGACGTGAGT CAGACGACGA AACCTCGGGG
101 Q  P  A  A    A  I  L    A  L  L    P  A  L  S    L  L  L    W  S  P

361 AGACAGCTGT AG
    TCTGTCGACA TC
121 R  Q  L  0
```

FIG. 15

```
  1 ATGAAGGCTG TGCTGCTTGC CCTGTTGATG GCAGGCTTGG CCCTGCAGCC AGGCACTGCC
    TACTTCCGAC ACGACGAACG GGACAACTAC CGTCCGAACC GGGACGTCGG TCCGTGACGG
  1 M  K  A  V  L  L  A  L  L  M  A  G  L  A  L  Q  P  G  T  A

61 CTGTTGTGCT ACTCCTGCAA GGCCCAGGTG AGCAACGAGG ACTGCCTGAA TGTGGAGAAC
    GACAACACGA TGAGGACGTT CCGGGTCCAC TCGTTGCTCC TGACGGACTT ACACCTCTTG
 21 L  L  C  Y  S  C  K  A  Q  V  S  N  E  D  C  L  N  V  E  N

121 TGCACGCAGC CGGAGGAGCA GTGCTGGACC GAGCGCATCC GCGCCGTGGG CCTCCTGACC
    ACGTGCGTCG GCCTCCTCGT CACGACCTGG CTCGCGTAGG CGCGGCACCC GGAGGACTGG
 41 C  T  Q  P  E  E  Q  C  W  T  E  R  I  R  A  V  G  L  L  T

181 GTCATCAGCA AAGGCTGCAG CTCAAACTGC GTGGATGACT CACAGGACTA CTACGTGGGC
    CAGTAGTCGT TTCCGACGTC GAGTTTGACG CACCTACTGA GTGTCCTGAT GATGCACCCG
 61 V  I  S  K  G  C  S  S  N  C  V  D  D  S  Q  D  Y  Y  V  G

241 AAGAAGAACA TCACCTGCTG TGACACCGAC TTGTGCAACG CCAGCGGGGC CCATGCCCTG
    TTCTTCTTGT AGTGGACGAC ACTGTGGCTG AACACGTTGC GGTCGCCCCG GGTACGGGAC
 81 K  K  N  I  T  C  C  D  T  D  L  C  N  A  S  G  A  H  A  L

301 CAGCCAGCTG CTGCCATCCT GGCACTGCTC CCTGCACTCA GCCTGCTGCT TTGGGGCCCC
    GTCGGTCGAC GACGGTAGGA CCGTGACGAG GGACGTGAGT CGGACGACGA AACCCCGGGG
101 Q  P  A  A  A  I  L  A  L  L  P  A  L  S  L  L  L  W  G  P

361 AGACAGCTGT AG
    TCTGTCGACA TC
121 R  Q  L  O
```

FIG. 16

```
                  10         20         30         40         50
HUMAN       MKAVLLALLMAGLALQPGTALLCYSCKAQVSNEDCLQVENCTQLGEQCWT
            *********************************** ****** ****
CYNOMOLGUS  MKAVLLALLMAGLALQPGTALLCYSCKAQVSNEDCLNVENCTQPEEQCWT
                  10         20         30         40         50

60         70         80         90        100
HUMAN       ARIRAVGLLTVISKGCSLNCVDDSQDYYVGKKNITCCDTDLCNASGAHAL
            ************** ***********************************
CYNOMOLGUS  ERIRAVGLLTVISKGCSSNCVDDSQDYYVGKKNITCCDTDLCNASGAHAL
                  60         70         80         90        100

110        120
HUMAN       QPAAAILALLPALGLLLWGPGQL
            ************ **** * **
CYNOMOLGUS  QPAAAILALLPALSLLLWSPRQL
                  110        120
```

FIG. 17

Source: Nocardia

```
                            SEQUENCE LISTING

<160> NUMBER OF SEQ ID NOS: 25

<210> SEQ ID NO 1
<211> LENGTH: 123
<212> TYPE: PRT
<213> ORGANISM: Homo sapiens

<400> SEQUENCE: 1

Met Lys Ala Val Leu Leu Ala Leu Leu Met Ala Gly Leu Ala Leu
 1               5                   10                  15

Gln Pro Gly Thr Ala Leu Leu Cys Tyr Ser Cys Lys Ala Gln Val
                20                  25                  30

Ser Asn Glu Asp Cys Leu Gln Val Glu Asn Cys Thr Gln Leu Gly
                35                  40                  45

Glu Gln Cys Trp Thr Ala Arg Ile Arg Ala Val Gly Leu Leu Thr
                50                  55                  60

Val Ile Ser Lys Gly Cys Ser Leu Asn Cys Val Asp Asp Ser Gln
                65                  70                  75

Asp Tyr Tyr Val Gly Lys Lys Asn Ile Thr Cys Cys Asp Thr Asp
                80                  85                  90

Leu Cys Asn Ala Ser Gly Ala His Ala Leu Gln Pro Ala Ala Ala
                95                  100                 105

Ile Leu Ala Leu Leu Pro Ala Leu Gly Leu Leu Leu Trp Gly Pro
                110                 115                 120

Gly Gln Leu

<210> SEQ ID NO 2
<211> LENGTH: 372
<212> TYPE: DNA
<213> ORGANISM: Homo sapiens

<400> SEQUENCE: 2 atg aag gct gtg ctg ctt gcc ctg ttg atg gca ggc              36
    Met Lys Ala Val Leu Leu Ala Leu Leu Met Ala Gly
     1               5                   10 ttg gcc ctg cag cca ggc act gcc ctg ctg tgc tac tcc              75
Leu Ala Leu Gln Pro Gly Thr Ala Leu Leu Cys Tyr Ser
         15                  20                  25 tgc aaa gcc cag gtg agc aac gag gac tgc ctg cag gtg             114
Cys Lys Ala Gln Val Ser Asn Glu Asp Cys Leu Gln Val
                30                  35 gag aac tgc acc cag ctg ggg gag cag tgc tgg acc gcg             153
Glu Asn Cys Thr Gln Leu Gly Glu Gln Cys Trp Thr Ala
     40                  45                  50 cgc atc cgc gca gtt ggc ctc ctg acc gtc atc agc aaa             192
Arg Ile Arg Ala Val Gly Leu Leu Thr Val Ile Ser Lys
             55                  60 ggc tgc agc ttg aac tgc gtg gat gac tca cag gac tac             231
Gly Cys Ser Leu Asn Cys Val Asp Asp Ser Gln Asp Tyr
 65                  70                  75
```

```
tac gtg ggc aag aag aac atc acg tgc tgt gac acc gac        270
Tyr Val Gly Lys Lys Asn Ile Thr Cys Cys Asp Thr Asp
        80                  85                  90 ttg tgc aac gcc agc ggg gcc cat gcc ctg cag ccg gct        309
Leu Cys Asn Ala Ser Gly Ala His Ala Leu Gln Pro Ala
                95                  100 gcc gcc atc ctt gcg ctg ctc cct gca ctc ggc ctg ctg        348
Ala Ala Ile Leu Ala Leu Leu Pro Ala Leu Gly Leu Leu
        105                 110                 115 ctc tgg gga ccc ggc cag cta tag                            372
Leu Trp Gly Pro Gly Gln Leu
                120

<210> SEQ ID NO 3
<211> LENGTH: 96
<212> TYPE: PRT
<213> ORGANISM: Mus musculus

<400> SEQUENCE: 3

Ser Val Ser Ile Ser Cys Arg Ser Ser Lys Ser Leu Leu His Ser
 1               5                   10                  15

Asn Gly Asn Thr Tyr Leu Tyr Trp Phe Leu Gln Arg Pro Gly Gln
                20                  25                  30

Ser Pro Gln Leu Leu Ile Tyr Arg Met Ser Asn Leu Ala Ser Gly
                35                  40                  45

Val Pro Asp Arg Phe Ser Gly Ser Gly Ser Gly Thr Val Phe Thr
                50                  55                  60

Leu Arg Ile Ser Arg Val Glu Ala Glu Asp Val Gly Val Tyr Tyr
                65                  70                  75

Cys Met Gln His Leu Glu Ser Pro Phe Thr Phe Gly Ser Gly Thr
                80                  85                  90

Lys Leu Glu Ile Lys Arg
                95

<210> SEQ ID NO 4
<211> LENGTH: 115
<212> TYPE: PRT
<213> ORGANISM: Mus Musculus
<220> FEATURE:
<221> NAME/KEY: unsure
<222> LOCATION: 46-48, 50-52
<223> OTHER INFORMATION: unknown amino acid

<400> SEQUENCE: 4

Glu Leu Val Lys Pro Gly Ala Pro Val Lys Leu Ser Cys Lys Ala
 1               5                   10                  15

Ser Gly Tyr Thr Phe Thr Asn Tyr Trp Met Asn Trp Val Lys Gln
                20                  25                  30

Arg Pro Gly Arg Gly Leu Glu Trp Ile Gly Arg Ile Asp Pro Ser
                35                  40                  45

Xaa Xaa Xaa Thr Xaa Xaa Xaa Gln Thr Phe Lys Asp Lys Ala Thr
                50                  55                  60

Leu Thr Val Asp Lys Ser Ser Ser Thr Ala Tyr Ile Gln Leu Ser
                65                  70                  75

Ser Leu Thr Ser Glu Asp Ser Ala Val Tyr Tyr Cys Ala Ile Thr
                80                  85                  90

Ala Ala Ile Ala Met Asp Tyr Trp Gly Gln Gly Thr Ser Val Thr
                95                  100                 105
```

```
Val Ser Ser Ala Lys Thr Thr Gly Pro Ser
            110             115
```

<210> SEQ ID NO 5
<211> LENGTH: 113
<212> TYPE: PRT
<213> ORGANISM: Mus musculus

<400> SEQUENCE: 5

```
Asp Ile Val Met Thr Gln Ala Ala Pro Ser Val Pro Val Thr Pro
1               5                  10                  15

Gly Glu Ser Val Ser Ile Ser Cys Arg Ser Lys Ser Leu Leu
                20                  25                  30

His Ser Asn Gly Asn Thr Tyr Leu Tyr Trp Phe Leu Gln Arg Pro
                35                  40                  45

Gly Gln Ser Pro Gln Leu Leu Ile Tyr Arg Met Ser Asn Leu Ala
                50                  55                  60

Ser Gly Val Pro Asp Arg Phe Ser Gly Ser Gly Ser Gly Thr Ala
                65                  70                  75

Phe Thr Leu Arg Ile Ser Arg Val Glu Ala Glu Asp Val Gly Val
                80                  85                  90

Tyr Tyr Cys Leu Gln His Leu Glu Tyr Pro Tyr Thr Phe Gly Gly
                95                  100                 105

Gly Thr Lys Leu Glu Leu Lys Arg
                110
```

<210> SEQ ID NO 6
<211> LENGTH: 124
<212> TYPE: PRT
<213> ORGANISM: Mus musculus

<400> SEQUENCE: 6

```
Gln Val Gln Val Gln Gln Pro Gly Ala Glu Leu Val Lys Pro Gly
1               5                  10                  15

Ala Pro Val Lys Leu Ser Cys Lys Ala Ser Gly Tyr Thr Phe Thr
                20                  25                  30

Asn Tyr Trp Leu Asn Trp Val Lys Gln Arg Pro Gly Arg Gly Leu
                35                  40                  45

Glu Trp Ile Gly Arg Ile Asp Pro Ser Asp Ser Glu Ile His Tyr
                50                  55                  60

Asp Gln Lys Phe Lys Asp Lys Ala Thr Leu Thr Val Asp Lys Ser
                65                  70                  75

Ser Ser Thr Ala Tyr Ile Gln Leu Ser Ser Leu Thr Ser Glu Asp
                80                  85                  90

Ser Ala Val Tyr Tyr Cys Ala Leu Thr Gly Ile Tyr Ala Met Ala
                95                  100                 105

Tyr Trp Gly Gln Gly Thr Ser Val Thr Val Ser Ser Ala Lys Thr
                110                 115                 120

Thr Gly Pro Ser
```

<210> SEQ ID NO 7
<211> LENGTH: 113
<212> TYPE: PRT
<213> ORGANISM: Mus musculus

<400> SEQUENCE: 7

```
Asp Val Val Met Thr Gln Thr Pro Leu Thr Leu Ser Val Thr Ile
1               5                  10                  15
```

Gly Gln Pro Ala Ser Ile Ser Cys Lys Ser Ser Gln Ser Leu Leu
                20                  25                  30

Asp Ser Asp Gly Lys Thr Tyr Leu Asn Trp Leu Leu Gln Arg Pro
                35                  40                  45

Gly Gln Ser Pro Lys Arg Leu Ile Tyr Leu Val Ser Thr Leu Asp
                50                  55                  60

Ser Gly Val Pro Asp Arg Phe Thr Gly Ser Gly Ser Gly Thr Asp
                65                  70                  75

Phe Thr Leu Lys Ile Ser Arg Val Glu Ala Glu Asp Leu Gly Val
                80                  85                  90

Tyr Tyr Cys Trp Gln Gly Thr His Phe Pro Arg Thr Phe Gly Gly
                95                 100                 105

Gly Thr Lys Leu Glu Ile Lys Arg
                110

<210> SEQ ID NO 8
<211> LENGTH: 121
<212> TYPE: PRT
<213> ORGANISM: Mus musculus

<400> SEQUENCE: 8

Glu Val Gln Leu Gln Gln Ser Gly Pro Asp Leu Glu Lys Pro Gly
 1               5                  10                  15

Ala Ser Val Lys Ile Ser Cys Lys Pro Ser Gly Asn Ser Phe Thr
                20                  25                  30

Gly Tyr Tyr Ile His Trp Val Lys Gln Ser His Gly Lys Ser Leu
                35                  40                  45

Glu Trp Ile Gly Arg Val Asp Pro Asn Asn Gly Phe Thr Ser Tyr
                50                  55                  60

Asn Gln Lys Phe Lys Gly Lys Ala Ile Leu Thr Val Asp Lys Ser
                65                  70                  75

Ser Ser Thr Ala Tyr Met Glu Leu Arg Ser Leu Thr Ser Glu Asp
                80                  85                  90

Ser Ala Val Tyr Tyr Cys Val Gly Asn Phe Phe Asp Ser Trp Gly
                95                 100                 105

Gln Gly Thr Thr Leu Thr Val Ser Ser Ala Lys Thr Thr Gly Pro
                110                 115                 120

Ser

<210> SEQ ID NO 9
<211> LENGTH: 118
<212> TYPE: PRT
<213> ORGANISM: Mus musculus

<400> SEQUENCE: 9

Pro Gly Ala Glu Leu Val Lys Pro Gly Ala Pro Val Lys Leu Ser
 1               5                  10                  15

Cys Lys Ala Ser Gly Tyr Thr Phe Thr Asn Tyr Trp Met Asn Trp
                20                  25                  30

Val Lys Gln Arg Pro Gly Arg Gly Leu Glu Trp Ile Gly Arg Ile
                35                  40                  45

Asp Pro Ser Asp Ser Glu Thr Gln Tyr Asn Gln Thr Phe Lys Asp
                50                  55                  60

Lys Ala Thr Leu Thr Val Asp Lys Ser Ser Ser Thr Ala Tyr Ile
                65                  70                  75

-continued

Gln Leu Ser Ser Leu Thr Ser Glu Asp Ser Ala Val Tyr Tyr Cys
                80                  85                  90

Ala Ile Thr Ala Ala Ile Ala Met Asp Tyr Trp Gly Gln Gly Thr
            95                 100                 105

Ser Val Thr Val Ser Ser Ala Lys Thr Thr Gly Pro Ser
            110                 115

<210> SEQ ID NO 10
<211> LENGTH: 238
<212> TYPE: PRT
<213> ORGANISM: Artificial Sequence
<220> FEATURE:
<223> OTHER INFORMATION: sequence is chimeric mouse/human

<400> SEQUENCE: 10

Met Gly Trp Ser Cys Ile Ile Leu Phe Leu Val Ala Thr Ala Thr
 1               5                  10                  15

Gly Val His Ser Asp Ile Val Met Thr Gln Ala Ala Pro Ser Val
                20                  25                  30

Pro Val Thr Pro Gly Glu Ser Val Ser Ile Ser Cys Arg Ser Ser
                35                  40                  45

Lys Ser Leu Leu His Ser Asn Gly Asn Thr Tyr Leu Tyr Trp Phe
                50                  55                  60

Leu Gln Arg Pro Gly Gln Ser Pro Gln Leu Leu Ile Tyr Arg Met
                65                  70                  75

Ser Asn Leu Ala Ser Gly Val Pro Asp Arg Phe Ser Gly Ser Gly
                80                  85                  90

Ser Gly Thr Ala Phe Thr Leu Arg Ile Ser Arg Val Glu Ala Glu
                95                 100                 105

Asp Val Gly Val Tyr Tyr Cys Leu Gln His Leu Glu Tyr Pro Tyr
                110                 115                 120

Thr Phe Gly Gly Gly Thr Lys Leu Glu Leu Lys Arg Thr Val Ala
                125                 130                 135

Ala Pro Ser Val Phe Ile Phe Pro Pro Ser Asp Glu Gln Leu Lys
                140                 145                 150

Ser Gly Thr Ala Ser Val Val Cys Leu Leu Asn Asn Phe Tyr Pro
                155                 160                 165

Arg Glu Ala Lys Val Gln Trp Lys Val Asp Asn Ala Leu Gln Ser
                170                 175                 180

Gly Asn Ser Gln Glu Ser Val Thr Glu Gln Asp Ser Lys Asp Ser
                185                 190                 195

Thr Tyr Ser Leu Ser Ser Thr Leu Thr Leu Ser Lys Ala Asp Tyr
                200                 205                 210

Glu Lys His Lys Val Tyr Ala Cys Glu Val Thr His Gln Gly Leu
                215                 220                 225

Ser Ser Pro Val Thr Lys Ser Phe Asn Arg Gly Glu Cys
                230                 235

<210> SEQ ID NO 11
<211> LENGTH: 466
<212> TYPE: PRT
<213> ORGANISM: Artificial Sequence
<220> FEATURE:
<223> OTHER INFORMATION: sequence is chimeric mouse/human

<400> SEQUENCE: 11

Met Gly Trp Ser Cys Ile Ile Leu Phe Leu Val Ala Thr Ala Thr
 1               5                  10                  15

-continued

Gly Val His Ser Gln Val Gln Val Gln Pro Gly Ala Glu Leu
                20                  25                  30

Val Lys Pro Gly Ala Pro Val Lys Leu Ser Cys Lys Ala Ser Gly
            35                  40                  45

Tyr Thr Phe Thr Asn Tyr Trp Leu Asn Trp Val Lys Gln Arg Pro
            50                  55                  60

Gly Arg Gly Leu Glu Trp Ile Gly Arg Ile Asp Pro Ser Asp Ser
            65                  70                  75

Glu Ile His Tyr Asp Gln Lys Phe Lys Asp Lys Ala Thr Leu Thr
            80                  85                  90

Val Asp Lys Ser Ser Ser Thr Ala Tyr Ile Gln Leu Ser Ser Leu
            95                  100                 105

Thr Ser Glu Asp Ser Ala Val Tyr Tyr Cys Ala Leu Thr Gly Ile
            110                 115                 120

Tyr Ala Met Ala Tyr Trp Gly Gln Gly Thr Ser Val Thr Val Ser
            125                 130                 135

Ser Ala Lys Thr Thr Gly Pro Ser Val Phe Pro Leu Ala Pro Ser
            140                 145                 150

Ser Lys Ser Thr Ser Gly Gly Thr Ala Ala Leu Gly Cys Leu Val
            155                 160                 165

Lys Asp Tyr Phe Pro Glu Pro Val Thr Val Ser Trp Asn Ser Gly
            170                 175                 180

Ala Leu Thr Ser Gly Val His Thr Phe Pro Ala Val Leu Gln Ser
            185                 190                 195

Ser Gly Leu Tyr Ser Leu Ser Ser Val Val Thr Val Pro Ser Ser
            200                 205                 210

Ser Leu Gly Thr Gln Thr Tyr Ile Cys Asn Val Asn His Lys Pro
            215                 220                 225

Ser Asn Thr Lys Val Asp Lys Lys Val Glu Pro Lys Ser Cys Asp
            230                 235                 240

Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr
            305                 310                 315

Asn Ser Thr Tyr Arg Val Val Ser Val Leu Thr Val Leu His Gln
            320                 325                 330

Asp Trp Leu Asn Gly Lys Glu Tyr Lys Cys Lys Val Ser Asn Lys
            335                 340                 345

Ala Leu Pro Ala Pro Ile Glu Lys Thr Ile Ser Lys Ala Lys Gly
            350                 355                 360

Gln Pro Arg Glu Pro Gln Val Tyr Thr Leu Pro Pro Ser Arg Glu
            365                 370                 375

Glu Met Thr Lys Asn Gln Val Ser Leu Thr Cys Leu Val Lys Gly
            380                 385                 390

Phe Tyr Pro Ser Asp Ile Ala Val Glu Trp Glu Ser Asn Gly Gln
            395                 400                 405

```
Pro Glu Asn Asn Tyr Lys Thr Thr Pro Pro Val Leu Asp Ser Asp
            410                 415                 420

Gly Ser Phe Phe Leu Tyr Ser Lys Leu Thr Val Asp Lys Ser Arg
            425                 430                 435

Trp Gln Gln Gly Asn Val Phe Ser Cys Ser Val Met His Glu Ala
            440                 445                 450

Leu His Asn His Tyr Thr Gln Lys Ser Leu Ser Leu Ser Pro Gly
            455                 460                 465

Lys

<210> SEQ ID NO 12
<211> LENGTH: 218
<212> TYPE: PRT
<213> ORGANISM: Artificial Sequence
<220> FEATURE:
<223> OTHER INFORMATION: sequence is chimeric mouse/human

<400> SEQUENCE: 12

Asp Val Val Met Thr Gln Thr Pro Leu Thr Leu Ser Val Thr Ile
  1               5                  10                  15

Gly Gln Pro Ala Ser Ile Ser Cys Lys Ser Ser Gln Ser Leu Leu
                 20                  25                  30

Asp Ser Asp Gly Lys Thr Tyr Leu Asn Trp Leu Leu Gln Arg Pro
             35                  40                  45

Gly Gln Ser Pro Lys Arg Leu Ile Tyr Leu Val Ser Thr Leu Asp
             50                  55                  60

Ser Gly Val Pro Asp Arg Phe Thr Gly Ser Gly Ser Gly Thr Asp
             65                  70                  75

Phe Thr Leu Lys Ile Ser Arg Val Glu Ala Glu Asp Leu Gly Val
             80                  85                  90

Tyr Tyr Cys Trp Gln Gly Thr His Phe Pro Arg Thr Phe Gly Gly
             95                 100                 105

Gly Thr Lys Leu Glu Ile Lys Arg Thr Val Ala Ala Pro Ser Val
            110                 115                 120

Phe Ile Phe Pro Pro Ser Asp Glu Gln Leu Lys Ser Gly Thr Ala
            125                 130                 135

Ser Val Val Cys Leu Leu Asn Asn Phe Tyr Pro Arg Glu Ala Lys
            140                 145                 150

Val Gln Trp Lys Val Asp Asn Ala Leu Gln Ser Gly Asn Ser Gln
            155                 160                 165

Glu Ser Val Thr Glu Gln Asp Ser Lys Asp Ser Thr Tyr Ser Leu
            170                 175                 180

Ser Ser Thr Leu Thr Leu Ser Lys Ala Asp Tyr Glu Lys His Lys
            185                 190                 195

Val Tyr Ala Cys Glu Thr His Gln Gly Leu Ser Ser Pro Val Thr
            200                 205                 210

Lys Ser Phe Asn Arg Gly Glu Cys
            215

<210> SEQ ID NO 13
<211> LENGTH: 222
<212> TYPE: PRT
<213> ORGANISM: Artificial Sequence
<220> FEATURE:
<223> OTHER INFORMATION: sequence is chimeric mouse/human

<400> SEQUENCE: 13
```

```
Glu Val Gln Leu Gln Gln Ser Gly Pro Asp Leu Glu Lys Pro Gly
 1               5                  10                  15

Ala Ser Val Lys Ile Ser Cys Lys Pro Ser Gly Asn Ser Phe Thr
            20                  25                  30

Gly Tyr Tyr Ile His Trp Val Lys Gln Ser His Gly Lys Ser Leu
            35                  40                  45

Glu Trp Ile Gly Arg Val Asp Pro Asn Gly Phe Thr Ser Tyr
            50                  55                  60

Asn Gln Lys Phe Lys Gly Lys Ala Ile Leu Thr Val Asp Lys Ser
            65                  70                  75

Ser Ser Thr Ala Tyr Met Glu Leu Arg Ser Leu Thr Ser Glu Asp
            80                  85                  90

Ser Ala Val Tyr Tyr Cys Val Gly Asn Phe Phe Asp Ser Trp Gly
            95                 100                 105

Gln Gly Thr Thr Leu Thr Val Ser Ser Ala Lys Thr Thr Gly Pro
           110                 115                 120

Ser Val Phe Pro Leu Ala Pro Ser Ser Lys Ser Thr Ser Gly Gly
           125                 130                 135

Thr Ala Ala Leu Gly Cys Leu Val Lys Asp Tyr Phe Pro Glu Pro
           140                 145                 150

Val Thr Val Ser Trp Asn Ser Gly Ala Leu Thr Ser Gly Val His
           155                 160                 165

Thr Phe Pro Ala Val Leu Gln Ser Ser Gly Leu Tyr Ser Leu Ser
           170                 175                 180

Ser Val Val Thr Val Pro Ser Ser Ser Leu Gly Thr Gln Thr Tyr
           185                 190                 195

Ile Cys Asn Val Asn His Lys Pro Ser Asn Thr Lys Val Asp Lys
           200                 205                 210

Lys Val Glu Pro Lys Ser Cys Asp Lys Thr His Thr
           215                 220

<210> SEQ ID NO 14
<211> LENGTH: 20
<212> TYPE: DNA
<213> ORGANISM: Artificial Sequence
<220> FEATURE:
<223> OTHER INFORMATION: Sequence is a primer

<400> SEQUENCE: 14
aaggctgtgc tgcttgccct                                              20

<210> SEQ ID NO 15
<211> LENGTH: 20
<212> TYPE: DNA
<213> ORGANISM: Artificial Sequence
<220> FEATURE:
<223> OTHER INFORMATION: Sequence is a primer

<400> SEQUENCE: 15
gagtggcaca aaggcctggg                                              20

<210> SEQ ID NO 16
<211> LENGTH: 372
<212> TYPE: DNA
<213> ORGANISM: Macaca fascicularis

<400> SEQUENCE: 16 atg aag gct gtg ctg ctt gcc ctg ttg atg gca ggc                 36
    Met Lys Ala Val Leu Leu Ala Leu Leu Met Ala Gly
```

```
                  1               5                       10
ttg gcc ctg cag cca ggc act gcc ctg ctg tgc tac tcc                      75
Leu Ala Leu Gln Pro Gly Thr Ala Leu Leu Cys Tyr Ser
             15                  20                  25 tgc aag gcc cag gtg agc aac gag gac tgc ctg aat gtg                     114
Cys Lys Ala Gln Val Ser Asn Glu Asp Cys Leu Asn Val
                 30                  35 gag aac tgc acg cag ccg gag gag cag tgc tgg acc gag                     153
Glu Asn Cys Thr Gln Pro Glu Glu Gln Cys Trp Thr Glu
         40                  45                  50 cgc atc cgc gcc gtg ggc ctc ctg acc gtc atc agc aaa                     192
Arg Ile Arg Ala Val Gly Leu Leu Thr Val Ile Ser Lys
                     55                  60 ggc tgc agc tca aac tgc gtg gat gac tca cag gac tac                     231
Gly Cys Ser Ser Asn Cys Val Asp Asp Ser Gln Asp Tyr
 65                  70                  75 tac gtg ggc aag aag aac atc acc tgc tgt gac acc gac                     270
Tyr Val Gly Lys Lys Asn Ile Thr Cys Cys Asp Thr Asp
         80                  85                  90 ttg tgc aac gcc agc ggg gcc cat gca ctg cag ccg gct                     309
Leu Cys Asn Ala Ser Gly Ala His Ala Leu Gln Pro Ala
                 95                 100 gct gcc atc ctg gca ctg ctc cct gca ctc agt ctg ctg                     348
Ala Ala Ile Leu Ala Leu Leu Pro Ala Leu Ser Leu Leu
        105                 110                 115 ctt tgg agc ccc aga cag ctg t  ag                                       372
Leu Trp Ser Pro Arg Gln Leu
                120         123
```

<210> SEQ ID NO 17
<211> LENGTH: 123
<212> TYPE: PRT
<213> ORGANISM: Macaca fascicularis

<400> SEQUENCE: 17

```
Met Lys Ala Val Leu Leu Ala Leu Leu Met Ala Gly Leu Ala Leu
 1               5                   10                  15

Gln Pro Gly Thr Ala Leu Leu Cys Tyr Ser Cys Lys Ala Gln Val
                 20                  25                  30

Ser Asn Glu Asp Cys Leu Asn Val Glu Asn Cys Thr Gln Pro Glu
                 35                  40                  45

Glu Gln Cys Trp Thr Glu Arg Ile Arg Ala Val Gly Leu Leu Thr
                 50                  55                  60

Val Ile Ser Lys Gly Cys Ser Ser Asn Cys Val Asp Asp Ser Gln
                 65                  70                  75

Asp Tyr Tyr Val Gly Lys Lys Asn Ile Thr Cys Cys Asp Thr Asp
                 80                  85                  90

Leu Cys Asn Ala Ser Gly Ala His Ala Leu Gln Pro Ala Ala Ala
                 95                 100                 105

Ile Leu Ala Leu Leu Pro Ala Leu Ser Leu Leu Leu Trp Ser Pro
                110                 115                 120

Arg Gln Leu
```

<210> SEQ ID NO 18
<211> LENGTH: 372
<212> TYPE: DNA
<213> ORGANISM: Macaca fascicularis

<400> SEQUENCE: 18

```
atg aag gct gtg ctg ctt gcc ctg ttg atg gca ggc                    36
Met Lys Ala Val Leu Leu Ala Leu Leu Met Ala Gly
 1               5                  10 ttg gcc ctg cag cca ggc act gcc ctg ttg tgc tac tcc                75
Leu Ala Leu Gln Pro Gly Thr Ala Leu Leu Cys Tyr Ser
         15                  20                  25 tgc aag gcc cag gtg agc aac gag gac tgc ctg aat gtg               114
Cys Lys Ala Gln Val Ser Asn Glu Asp Cys Leu Asn Val
                 30                  35 gag aac tgc acg cag ccg gag gag cag tgc tgg acc gag               153
Glu Asn Cys Thr Gln Pro Glu Glu Gln Cys Trp Thr Glu
         40                  45                  50 cgc atc cgc gcc gtg ggc ctc ctg acc gtc atc agc aaa               192
Arg Ile Arg Ala Val Gly Leu Leu Thr Val Ile Ser Lys
                 55                  60 ggc tgc agc tca aac tgc gtg gat gac tca cag gac tac               231
Gly Cys Ser Ser Asn Cys Val Asp Asp Ser Gln Asp Tyr
 65                  70                  75 tac gtg ggc aag aag aac atc acc tgc tgt gac acc gac               270
Tyr Val Gly Lys Lys Asn Ile Thr Cys Cys Asp Thr Asp
         80                  85                  90 ttg tgc aac gcc agc ggg gcc cat gcc ctg cag cca gct               309
Leu Cys Asn Ala Ser Gly Ala His Ala Leu Gln Pro Ala
                 95                 100 gct gcc atc ctg gca ctg ctc cct gca ctc agc ctg ctg               348
Ala Ala Ile Leu Ala Leu Leu Pro Ala Leu Ser Leu Leu
        105                 110                 115 ctt tgg ggc ccc aga cag ctg t  ag                                 372
Leu Trp Gly Pro Arg Gln Leu
                120     123

<210> SEQ ID NO 19
<211> LENGTH: 123
<212> TYPE: PRT
<213> ORGANISM: Macaca fascicularis

<400> SEQUENCE: 19

Met Lys Ala Val Leu Leu Ala Leu Leu Met Ala Gly Leu Ala Leu
 1               5                  10                  15

Gln Pro Gly Thr Ala Leu Leu Cys Tyr Ser Cys Lys Ala Gln Val
                 20                  25                  30

Ser Asn Glu Asp Cys Leu Asn Val Glu Asn Cys Thr Gln Pro Glu
                 35                  40                  45

Glu Gln Cys Trp Thr Glu Arg Ile Arg Ala Val Gly Leu Leu Thr
                 50                  55                  60

Val Ile Ser Lys Gly Cys Ser Ser Asn Cys Val Asp Asp Ser Gln
                 65                  70                  75

Asp Tyr Tyr Val Gly Lys Lys Asn Ile Thr Cys Cys Asp Thr Asp
                 80                  85                  90

Leu Cys Asn Ala Ser Gly Ala His Ala Leu Gln Pro Ala Ala Ala
                 95                 100                 105

Ile Leu Ala Leu Leu Pro Ala Leu Ser Leu Leu Leu Trp Gly Pro
                110                 115                 120

Arg Gln Leu

<210> SEQ ID NO 20
<211> LENGTH: 35
<212> TYPE: DNA
```

```
<213> ORGANISM: Artificial Sequence
<220> FEATURE:
<223> OTHER INFORMATION: Sequence is a primer

<400> SEQUENCE: 20
actatgaagc tttgcagctc atcccttcac aatcg                                35

<210> SEQ ID NO 21
<211> LENGTH: 42
<212> TYPE: DNA
<213> ORGANISM: Artificial Sequence
<220> FEATURE:
<223> OTHER INFORMATION: Sequence is a primer

<400> SEQUENCE: 21
gaattcggat ccaccatgaa gaccgtcttc tttctcctgc tg                        42

<210> SEQ ID NO 22
<211> LENGTH: 17
<212> TYPE: DNA
<213> ORGANISM: Artificial Sequence
<220> FEATURE:
<223> OTHER INFORMATION: Sequence is a PCR primer

<400> SEQUENCE: 22
cctgctggcc acctact                                                    17

<210> SEQ ID NO 23
<211> LENGTH: 18
<212> TYPE: DNA
<213> ORGANISM: Artificial Sequence
<220> FEATURE:
<223> OTHER INFORMATION: Sequence is a primer

<400> SEQUENCE: 23
ccttcacaat cgggctat                                                   18

<210> SEQ ID NO 24
<211> LENGTH: 20
<212> TYPE: DNA
<213> ORGANISM: Artificial Sequence
<220> FEATURE:
<223> OTHER INFORMATION: Sequence is a PCR primer

<400> SEQUENCE: 24
acccacgcgt ccggctgctt                                                 20

<210> SEQ ID NO 25
<211> LENGTH: 21
<212> TYPE: DNA
<213> ORGANISM: Artificial Sequence
<220> FEATURE:
<223> OTHER INFORMATION: Sequence is a PCR primer

<400> SEQUENCE: 25
cgggggacac cacggaccag a                                               21
```

ANTI-TUMOR ANTIBODY COMPOSITIONS AND METHODS OF USE

RELATED APPLICATIONS

This application is a divisional application of U.S. patent application Ser. No. 09/698,705 now U.S. Pat. No. 6,824,780, filed on Oct. 27, 2000, which claims the benefit under 35 U.S.C. §1.19(e) to provisional application 60/162,558 filed Oct. 29, 1999, and 60/182,872 filed Feb. 16, 2000, the entire disclosures of which are hereby incorporated by reference.

FIELD OF THE INVENTION

The present invention relates to anti-PSCA antibody compositions and methods of killing PSCA-expressing cancers cells.

BACKGROUND OF THE INVENTION

In humans, prostate cancer is one of the most commonly diagnosed malignancies in males and is the second leading cause of cancer related death in men. The American Cancer Society estimates that for the year 2000, 180,400 new cases of prostate cancer will be diagnosed with 31,900 deaths from the disease. In advanced stages, prostate cancer metastasizes to the bone. While advances in early diagnosis and treatment of locally confined tumors have been achieved, prostate cancer is incurable once it has metastasized. Patients with metastatic prostate cancer on hormonal therapy will eventually develop an androgen-refractory (androgen independent) state that will lead to disease progression and death. Currently, prostate-specific antigen (PSA) is the most widely used tumor marker for screening, diagnosis, and monitoring prostate cancer. However, widespread use of PSA as a tool for screening is controversial since PSA fails to discriminate accurately between benign and malignant prostate disease.

Depending on the stage of the cancer, prostate and bladder cancer treatment involves one or a combination of the following therapies: surgery to remove the cancerous tissue, radiation therapy, chemotherapy, androgen deprivation (e.g., hormonal therapy) in the case of prostate cancer. While surgical or radiation therapy significantly improves survival in patients with early stages of the disease, the therapeutic options are very limited for advanced cases, particularly for tumor recurrences following hormone ablation. The majority of patients who undergo hormone therapy progress to develop androgen-independent disease. Currently, there is no effective treatment for the 20-40% of prostate cancer patients who develop recurrent disease after surgery or radiation therapy, or for those in whom the cancer has metastasized at the time of diagnosis. Chemotherapy has its toxic side effects, especially in elderly patients. Development of new forms of therapy especially for disease refractory to androgen deprivation is an urgent need in the management of prostatic carcinoma.

The identification of a novel cell surface antigen, prostate stem cell antigen (PSCA) has been described, see, e.g., U.S. Pat. No. 5,856,136 (SCAH2), WO 99/14328 (protein PRO232), WO 98/40403 (PSCA), WO 98/51805 (PS116) and Reiter et al. *Proc. Nat. Acad. Sci.* 95:1735-1740 (1998). PSCA was initially cloned from a cDNA library of a LAPC-4 xenograft from a prostate cancer patient.

PSCA is a GPI-linked molecule of 123 amino acids that is expressed on the surface of a number of cell types including prostate and bladder tumor cells. The gene is located on the myc locus on 8Q24.2 which is a region amplified in 80% of prostate cancers. PSCA shows 30% homology with SCA-2. The protein has a hydrophobic signal sequence at the first 20 amino acids of the N-terminus and a GPI-anchoring sequence at amino acid 100-123 of the C-terminus (FIG. 2 on page 1737 of Reiter et al. (1998)). There are four predicted glycoslylation sites. The cell surface protein is shed with a $t_{1/2}$ of about 10 hours in culture. It has been reported that PSCA is widely over-expressed across all stages of prostate cancer, including high grade prostatic intraepithelial neoplasia (PIN), and both androgen-dependent and -independent prostate tumors. Antibodies that are able to target PSCA-expressing tumor cells in vivo and that can internalize upon binding to the cells, have not been reported.

Antibody-based therapy has proved very effective in the treatment of various cancers. For example, HERCEPTIN® and RITUXAN® (both from Genentech, S. San Francisco), have been used successfully to treat breast cancer and non-Hodgkin's lymphoma, respectively. HERCEPTIN® is a recombinant DNA-derived humanized monoclonal antibody that selectively binds to the extracellular domain of the human epidermal growth factor receptor 2 (HER2) proto-oncogene. HER2 protein overexpression is observed in 25-30% of primary breast cancers. RITUXAN® is a genetically engineered chimeric murine/human monoclonal antibody directed against the CD20 antigen found on the surface of normal and malignant B lymphocytes. Both these antibodies are produced in CHO cells.

The present invention provides alternative methods of treating cancer that overcome the limitations of conventional therapeutic methods as well as offer additional advantages that will be apparent from the detailed description below.

SUMMARY OF THE INVENTION

The invention provides isolated anti-PSCA antibodies that internalize upon binding to PSCA on a mammalian cell in vivo. These antibodies can also target a PCSA-expressing tumor cell in vivo. In a specific embodiment, the anti-PSCA antibodies internalize upon binding to PSCA on cancer cells, including prostate cancer, urinary tract cancers (e.g., bladder cancer) and lung cancer. Provided are internalizing anti-PSCA antibodies that are monoclonal antibodies. In specific embodiments, the antibodies are 10E3, 6F8, 8D11, 5F2, 6C3, 6B8 and 10C5, produced by the hybridomas deposited under American Type Culture Collection accession number PTA-717, PTA-718, PTA-719, PTA-720, PTA-880, PTA-2265, and PTA-2264. The V region sequences of the 6F8, 8D11, 5F2, 6B8 antibodies are shown in FIG. 12 (SEQ ID NOs. 3-9). The chimeric murine-human antibody polypeptides having the amino acid sequence of SEQ ID NO.10, SEQ ID NO.11, SEQ ID NO.12, or SEQ ID NO.13, are provided. The invention provides anti-PSCA antibodies and antibody fusion polypeptides that comprise the amino acid sequences of any one of SEQ ID NO. 1-13.

Also provided are antibodies that compete for binding to the same epitope as the epitope bound by any of the aforementioned monoclonal antibodies. In another embodiment, an isolated anti-PSCA monoclonal antibody that inhibits the growth of PSCA-expressing cancer cells in vivo, or is cytotoxic in vivo, to such cells and tumors containing such cells, is provided.

The invention also provides anti-PSCA antibodies that are conjugated to a cytotoxic agent or to a growth inhibitory agent. The antibodies are internalizing and/or growth inhibitory antibodies. The cytotoxic agent can be a toxin, antibiotic, radioactive isotope or nucleolytic enzyme. In a preferred embodiment, the toxin is a maytansinoid, more preferably the maytansinoid having the structure shown in FIG. 22.

The anti-PSCA antibodies of the preceding embodiments include intact (full length) antibodies as well as antibody fragments. The anti-PSCA antibodies of the invention include human antibodies and chimeric antibodies as well as antibody fusion polypeptides comprising at least the antibody V region sequences fused to a heterologous polypeptide. In a preferred embodiment, the anti-PSCA antibody of any of the preceding embodiments is a chimeric or human antibody. In a preferred embodiment, the chimeric antibody is a humanized antibody. The humanized anti-PSCA antibodies include humanized forms of any of the antibodies produced by the hybridomas deposited under American Type Culture Collection accession number PTA-717, PTA-718, PTA-719, PTA-720, PTA-880, and PTA-2265 and the chimeric antibodies include those having amino acid sequences of SEQ ID NO.10-13 as shown in FIG. 13. The antibodies of the invention include those produced in mammalian or bacterial cells.

The invention also encompasses a composition comprising any one of the anti-PSCA antibodies of the above embodiments, and a carrier. In one embodiment, the antibody in the composition is a human antibody or a humanized form of the monoclonal antibody produced by any one of the hybridomas deposited under ATCC accession number PTA-717, PTA-718, PTA-719, PTA-720, PTA-880, PTA-2265, and PTA-2264. In one specific embodiment, the antibody in the composition is conjugated to a maytansinoid. In a preferred embodiment, the carrier is a pharmaceutically-acceptable carrier. These compositions can be provided in an article of manufacture or a kit.

Another aspect of the invention is an isolated nucleic acid encoding any one of the anti-PSCA antibodies of the above embodiments, as well as an expression vector comprising the isolated nucleic acid operably linked to an expression regulatory sequence.

Also provided by the invention are cells that produce the above-described anti-PSCA antibodies. In one embodiment, the antibody producing cells are hybridoma cells including the specific hybridoma cells having ATCC accession numbers PTA-717, PTA-718, PTA-719, PTA-720, PTA-880, PTA-2265, and PTA-2264. In another embodiment, the cell is a bacterial cell. A host cell comprising the above-described vector is specifically provided.

The invention further encompasses a method of producing the anti-PSCA antibodies of the above embodiments, comprising culturing the cells of the above embodiments and recovering the antibody from the cell culture.

Yet a separate aspect of the invention is a method of killing a PSCA-expressing cancer cell, comprising contacting the cancer cell with an anti-PSCA antibody of any of the above embodiments, thereby killing the cancer cell. Another aspect is a method of alleviating or treating a PSCA-expressing cancer in a mammal, comprising administering a therapeutically effective amount of the anti-PSCA antibodies of the invention to the mammal. In preferred embodiments of the preceding two methods, the cancer is a prostate, bladder or lung cancer, more preferably prostate cancer and especially an androgen independent prostate cancer cell or a metastatic prostate cancer. In a preferred embodiment of these methods, the anti-PSCA antibody is a human or a humanized antibody. In another preferred embodiment, the antibody is conjugated to a cytotoxic agent such as a toxin or a radioactive isotope. Preferably, the toxin is calicheamicin or a maytansinoid such as "DM1" having the structure shown in FIG. 22. The method of alleviating the PSCA-expressing cancer anticipates administration of the anti-PSCA antibody in conjuction with chemotherapy wherein the mammal is also receiving at least one chemotherapeutic agent. In a specific embodiment, the chemotherapeutic agent is a taxane such as paclitaxel (TAXOL®) or docetaxel, or derivatives and analogs thereof.

In a further aspect, the invention provides an article of manufacture comprising a container and a composition contained therein, wherein the composition comprises an anti-PSCA antibody of the above embodiments, and further comprising a package insert indicating that the composition can be used to alleviate or treat a PSCA-expressing cancer and in particular, prostate cancer.

BRIEF DESCRIPTION OF THE FIGURES

FIGS. 9A and 9B show cells incubated with antibody 6C3 for 15 minutes and 1 hour, respectively. FIGS. 9C and 9D show cells incubated with antibody 10E3 for 15 minutes and 1 hour, respectively.

FIG. 12 shows the amino acid sequences of the heavy and light chain variable region domains ($V_H$ and $V_L$) of the antibodies from hybridoma clones 6F8.2F4, Asc# 2395; 8D11.2E9, Asc# 2399; 5F2.4H4.1E3, Asc# 2403; and 6B8.1D7.2B3, Asc#2761.

FIG. 13 shows the amino acid sequences of the full length chimeric 2403 IgG including the signal peptide sequences, and the sequences of chimeric 6B8 Fab.

FIG. 15 shows the DNA and protein sequences of the Cynomolgus monkey PSCA type 1 (SEQ ID NO: 16 and NO:17, respectively), see Example 6. The "o" at the end of the amino acid sequence stands for the Ochre stop codon.

FIG. 16 shows the DNA and protein sequences of the Cynomolgus monkey PSCA type II (SEQ ID NO: 18 and NO: 19, respectively), see Example 6. The "o" at the end of the amino acid sequence stands for the Ochre stop codon.

FIG. 17 compares the amino acid sequences for human PSCA (SEQ ID NO.1) and Cynomolgus monkey type I PSCA (SEQ ID NO. 17).

DETAILED DESCRIPTION OF PREFERRED EMBODIMENTS

I. Definitions

Figure 1:
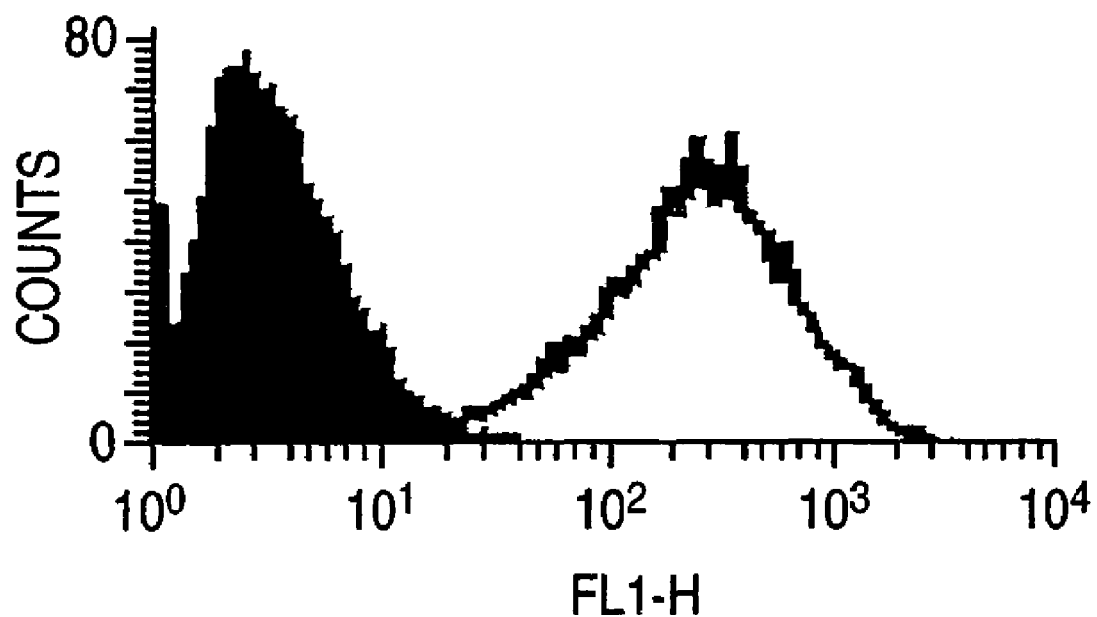
FIG. 1 shows the binding to and staining of gD-PSCA transfected CHO cells by Mab by 5F2, as assayed by FACS (see Example 1).
Figure 2:
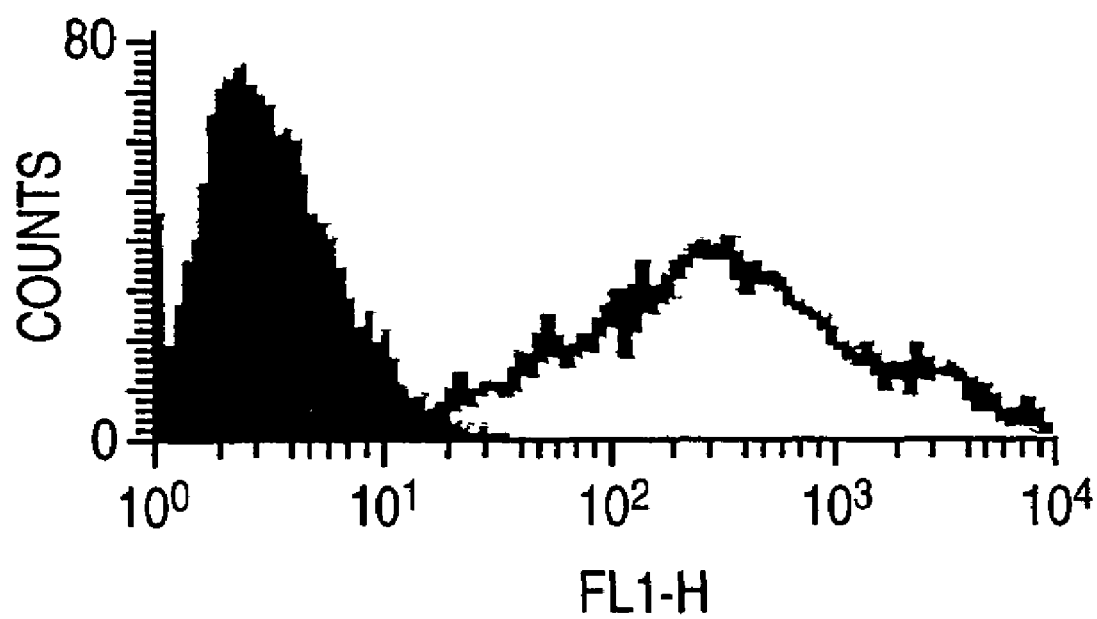
FIG. 2 shows the binding to and staining of gD-PSCA transfected CHO cells by Mab by 10C5, as assayed by FACS (see Example 1).

Human "PSCA" or "prostate stem cell antigen" as used herein, refers to a single subunit glycoprotein of 123 amino acids that is expressed on the cell surface as a glycosylphosphatidylinositol (GPI)-anchored protein, whose nucleotide and amino acid sequence sequences are as disclosed in e.g., U.S. Pat. No. 5,856,136 (SCAH2; SEQ ID NO:4); WO 99/14328 (PRO232, nucleotide sequence in SEQ ID NO:1, FIG. 1; amino acid sequence in FIG. 2; SEQ ID NO:2); FIG. 2 (amino acid sequence) on page 1737 of Reiter et al. *Proc. Nat. Acad. Sci.* 95:1735-1740 (1998); WO 98/51805 (SEQ ID NOs: 12 and 25); and WO 98/40403 (FIGS. 1A and 1B). The amino acid sequence of murine PSCA is provided in FIG. 2 on page 1737 of Reiter et al. *Proc. Nat. Acad. Sci.* 95:1735-1740 (1998). The protein has a signal sequence at the amino-terminus and the GPI-anchoring sequence is present at the carboxy terminus. In the human PSCA sequence, amino acids 1-20 represent the N-terminal signal sequence which gets cleaved in the mature protein, and amino acid positions 100-123 represent C-terminal GPI-anchoring sequences (Reiter et al., 1998, see FIG. 2). Thus, the amino acids 21 to about 100 are presumably on the cell surface. PSCA as used herein include allelic variants and conservative substitution mutants of the protein which have PSCA biological activity. These allelic variants and conservative substitution mutants may be GPI-linked or secreted forms of the protein.

The term "antibody" (Ab) as used herein includes monoclonal antibodies, polyclonal antibodies, multispecific antibodies (e.g. bispecific antibodies), and antibody fragments, so long as they exhibit the desired biological activity. The term "immunoglobulin" (Ig) is used interchangeably with "antibody" herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ and μ, respectively. The y and a classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody obtained from a population of substantially homogeneous antibodies, ie., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature*, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

A "native sequence" polypeptide is one which has the same amino acid sequence as a polypeptide (e.g., antibody) derived from nature. Such native sequence polypeptides can be isolated from nature or can be produced by recombinant or synthetic means. Thus, a native sequence polypeptide can have the amino acid sequence of a naturally occurring human polypeptide, murine polypeptide, or polypeptide from any other mammalian species.

The term "amino acid sequence variant" refers to a polypeptide that has amino acid sequences that differ to some extent from a native sequence polypeptide. Ordinarily, amino acid sequence variants of PSCA will possess at least about 70% homology with the native sequence PSCA, preferably, at least about 80%, more preferably at least about 85%, even more preferably at least about 90% homology, and most preferably at least 95%. The amino acid sequence variants can possess substitutions, deletions, and/or insertions at certain positions within the amino acid sequence of the native amino acid sequence.

The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such molecule from having the ability to bind to the high affinity receptor, FcεRI.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

As used herein, an anti-PSCA antibody that "internalizes" is one that is taken up by (i.e., enters) the cell upon binding to PSCA on a mammalian cell (i.e. cell surface PSCA). The internalizing antibody will of course include antibody fragments, human or humanized antibody and antibody conjugate. For therapeutic applications, internalization in vivo is contemplated. The number of antibody molecules internalized will be sufficient or adequate to kill a PSCA-expressing cell, especially a PSCA-expressing cancer cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugate to the antibody is sufficient to kill the tumor cell.

Whether an anti-PSCA antibody internalizes upon binding PSCA on a mammalian cell can be determined by various assays including those described in the experimental examples below. For example, to test internalization in vivo, the test antibody is labeled and introduced into an animal known to have PSCA expressed on the surface of certain cells. The antibody can be radiolabeled or labeled with fluorescent or gold particles, for instance. Animals suitable for this assay include a mammal such as a NCR nude mouse that contains a human PSCA-expressing tumor transplant or xenograft, or a mouse into which cells transfected with human PSCA have been introduced, or a transgenic mouse expressing the human PSCA transgene. Appropriate controls include animals that did not receive the test antibody or that received an unrelated antibody, and animals that received an antibody to another antigen on the cells of interest, which antibody is known to be internalized upon binding to the antigen (e.g., HERCEPTIN which binds to Her2 expressed on the human breast tumor cell line, MCF-7 in Example 3). The antibody can be administered to the animal, e.g., by intravenous injection. At suitable time intervals, tissue sections of the animal can be prepared using known methods or as described in the experimental examples below, and analyzed by light microscopy or electron microscopy, for internalization as well as the location of the internalized antibody in the cell. For internalization in vitro, the cells can be incubated in tissue culture dishes in the presence or absence of the relevant antibodies added to the culture media and processed for microscopic analysis at desired time points. The presence of an internalized, labeled antibody in the cells can be directly visualized by microscopy or by autoradiography if radiolabeled antibody is used. Alternatively, in a quantitative biochemical assay, a population of cells comprising PSCA-expressing cells are contacted in vitro or in vivo with a radiolabeled test antibody and the cells (if contacted in vivo, cells are then isolated after a suitable amount of time) are treated with a protease or subjected to an acid wash to remove uninternalized antibody on the cell surface. The cells are ground up and the amount of protease resistant, radioactive counts per minute (cpm) associated with each batch of cells is measured by passing the homogenate through a scintillation counter. Based on the known specific activity of the radiolabeled antibody, the number of antibody molecules internalized per cell can be deduced from the scintillation counts of the ground-up cells. Cells are "contacted" with antibody in vitro preferably in solution form such as by adding the cells to the cell culture media in the culture dish or flask and mixing the antibody well with the media to ensure uniform exposure of the cells to the antibody. Instead of adding to the culture media, the cells can be contacted with the test antibody in an isotonic solution such as PBS in a test tube for the desired time period. In vivo, the cells are contacted with antibody by any suitable method of administering the test antibody such as the methods of administration described below when administered to a patient.

The faster the rate of internalization of the antibody upon binding to the PSCA expressing cell in vivo, the faster the desired killing or growth inhibitory effect on the target PSCA-expressing cell can be achieved, e.g., by a cytotoxic immunoconjugate. Preferably, the kinetics of internalization of the anti-PSCA antibodies are such that they favor rapid killing of the PSCA-expressing target cell. Therefore, it is desirable that the anti-PSCA antibody exhibit a rapid rate of internalization preferably, within 24 hours from administration of the antibody in vivo, more preferably within about 12 hours, even more preferably within about 30 minutes to 1 hour, and most preferably, within about 30 minutes. The present invention provides antibodies that internalize as fast as about 15 minutes from the time of introducing the anti-PSCA antibody in vivo. The antibody will preferably be internalized into the cell within a few hours upon binding to PSCA on the cell surface, preferably within 1 hour, even more preferably within 15-30 minutes.

To determine if a test antibody can compete for binding to the same epitope as the epitope bound by the anti-PSCA antibodies of the present invention including the antibodies produced by the hybridomas deposited with the ATCC, a cross-blocking assay e.g., a competitive ELISA assay can be performed. In an exemplary competitive ELISA assay, PSCA coated on the wells of a microtiter plate is pre-incubated with or without candidate competing antibody and then the biotin-labeled anti-PSCA antibody of the invention is added. The amount of labeled anti-PSCA antibody bound to the PSCA antigen in the wells is measured using avidin-peroxidase conjugate and appropriate substrate. The antibody can be labeled with a radioactive or fluorescent label or some other detectable and measurable label. The amount of labeled anti-PSCA antibody that bound to the antigen will have an indirect correlation to the ability of the candidate competing antibody (test antibody) to compete for binding to the same epitope, i.e., the greater the affinity of the test antibody for the same epitope, the less labeled antibody will be bound to the antigen-coated wells. A candidate competing antibody is considered an antibody that binds substantially to the same epitope or that competes for binding to the same epitope as an anti-PSCA antibody of the invention if the candidate antibody can block binding of the PSCA antibody by at least 20%, preferably by at least 20-50%, even more preferably, by at least 50% as compared to the control performed in parallel in the absence of the candidate competing antibody (but may be in the presence of a known non-competing antibody). It will be understood that variations of this assay can be performed to arrive at the same quantitative value.

An antibody having a "biological characteristic" of a designated antibody, such as any of the monoclonal antibodies 10E3, 6F8, 8D11 and 5F2, is one which possesses one or more of the biological characteristics of that antibody which distinguish it from other antibodies that bind to the same antigen, PSCA. For example, an antibody with a biological characteristic of 6F8 will bind the same epitope as that bound by 6F8 (e.g. which competes for binding or blocks binding of monoclonal antibody 6F8 to PSCA), be able to target a PSCA expressing tumor cell in vivo and will internalize upon binding to PSCA on a mammalian cell in vivo. Likewise, an antibody with the biological characteristic of the 5F2 or 6B8 antibody will have the same epitope binding, targeting, internalizing, tumor growth inhibitory and cytotoxic properties of the antibody.

The term "antagonist" antibody is used in the broadest sense, and includes an antibody that partially or fully blocks, inhibits, or neutralizes a biological activity of a native PSCA protein disclosed herein. Methods for identifying antagonists of a PSCA polypeptide may comprise contacting a PSCA polypeptide or a cell expressing PSCA on the cell surface, with a candidate antagonist antibody and measuring a detectable change in one or more biological activities normally associated with the PSCA polypeptide.

An "antibody that inhibits the growth of tumor cells expressing PSCA" or a "growth inhibitory" antibody is one which binds to and results in measurable growth inhibition of cancer cells expressing or overexpressing PSCA. Preferred growth inhibitory anti-PSCA antibodies inhibit growth of PSCA-expressing tumor cells (e.g., prostate cancer cells) by greater than 20%, preferably from about 20% to about 50%, and even more preferably, by greater than 50% (e.g. from about 50% to about 100%) as compared to the appropriate control, the control typically being tumor cells not treated with the antibody being tested. Growth inhibition can be measured at an antibody concentration of about 0.1 to 30 µg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-PSCA antibody at about 1 µg/kg to about 100 mg/kg body weight results in reduction in tumor size or tumor cell proliferation within about 5 days to 3 months from the first administration of the antibody, preferably within about 5 to 30 days.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses PSCA. Preferably the cell is a tumor cell, e.g. a prostate, breast, ovarian, stomach, endometrial, lung, kidney, colon, bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS* (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g. from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

A "PSCA-expressing cell" is a cell which expresses endogenous or transfected PSCA on the cell surface. A "PSCA-expressing cancer" is a cancer comprising cells that have PSCA protein present on the cell surface. A "PSCA-expressing cancer" produces sufficient levels of PSCA on the surface of cells thereof, such that an anti-PSCA antibody can bind thereto and have a therapeutic effect with respect to the cancer. A cancer which "overexpresses" PSCA is one which has significantly higher levels of PSCA at the cell surface thereof, compared to a noncancerous cell of the same tissue type. Such overexpression may be caused by gene amplification or by increased transcription or translation. PSCA overexpression may be determined in a diagnostic or prognostic assay by evaluating increased levels of the PSCA protein present on the surface of a cell (e.g. via an immunohistochemistry assay; FACS analysis). Alternatively, or additionally, one may measure levels of PSCA-encoding nucleic acid or mRNA in the cell, e.g. via fluorescent in situ hybridization; (FISH; see WO98/45479 published October, 1998), Southern blotting, Northern blotting, or polymerase chain reaction (PCR) techniques, such as real time quantitative PCR (RT-PCR). One may also study PSCA overexpression by measuring shed antigen in a biological fluid such as serum, e.g, using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al.

J. Immunol. Methods 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody. A PSCA-expressing cancer includes prostate, bladder, lung, uterine and breast cancer.

A "mammal" for purposes of treating a cancer or alleviating the symptoms of cancer, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a PSCA-expressing cancer if, after receiving a therapeutic amount of an anti-PSCA antibody according to the methods of the present invention, the patient shows observable and/or measurable reduction in or absence of one or more of the following: reduction of PSA levels, reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-PSCA antibody may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). For prostate cancer, the progress of therapy can be assessed by routine methods, usually by measuring serum PSA (prostate specific antigen) levels; the higher the level of PSA in the blood, the more extensive the cancer. Commercial assays for detecting PSA are available, e.g, Hybitech Tandem-E and Tandem-R PSA assay kits, the Yang ProsCheck polyclonal assay (Yang Labs, Bellevue, WA), Abbott Imx (Abbott Labs, Abbott Park, Ill.), etc. Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

For bladder cancer, which is a more localized cancer, methods to determine progress of disease include urinary cytologic evaluation by cystoscopy, monitoring for presence of blood in the urine, visualization of the urothelial tract by sonography or an intravenous pyelogram, computed tomography (CT) and magnetic resonance imaging (MRI). The presence of distant metastases can be assessed by CT of the abdomen, chest x-rays, or radionuclide imaging of the skeleton.

The term "therapeutically effective amount" refers to an amount of an antibody or a drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See preceding definition of "treating". To the extent the drug may prevent growth and/or kill existing cancer cells, it may be cytostatic and/or cytotoxic.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "growth inhibitory agent" when used herein refers to a compound or composition which inhibits growth of a cell, especially a PSCA expressing cancer cell, either in vitro or in vivo. Thus, the growth inhibitory agent may be one which significantly reduces the percentage of PSCA expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (*W B Saunders: Philadelphia*, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

The term "epitope tagged" used herein refers to a chimeric polypeptide comprising an anti-PSCA antibody polypeptide fused to a "tag polypeptide". The tag polypeptide has enough residues to provide an epitope against which an antibody can be made, yet is short enough such that it does not interfere with activity of the Ig polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The term "package insert" is used to refer to instructions customarily included in commercial packages of therapeutic products, that contain information about the indications, usage, dosage, administration, contraindications and/or warnings concerning the use of such therapeutic products.

An "isolated nucleic acid" is a nucleic acid, e.g., an RNA, DNA, or a mixed polymer, which is substantially separated from other genome DNA sequences as well as proteins or complexes such as ribosomes and polymerases, which naturally accompany a native sequence. The term embraces a nucleic acid sequence which has been removed from its naturally occurring environment, and includes recombinant or cloned DNA isolates and chemically synthesized analogues or analogues biologically synthesized by heterologous systems. A substantially pure molecule includes isolated forms of the molecule.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells. Suitable vectors are disclosed below.

The cell that produces an anti-PSCA antibody of the invention will include the parent hybridoma cell e.g., the hybridomas that are deposited with the ATCC, as well as bacterial and eukaryotic host cells into which nucleic acid encoding the antibodies have been introduced. Suitable host cells are disclosed below.

II. Compositions and Methods of the Invention

The invention provides anti-PSCA antibodies. In a preferred embodiment, the anti-PSCA antibodies internalize upon binding to cell surface PSCA on a mammalian cell. In another preferred embodiment, the anti-PSCA antibodies destroy or lead to the destruction of tumor cells bearing PSCA.

The pathway and kinetics of internalization of GPI anchored molecules has not been as well studied as the clathrin coated receptor-mediated internalization pathway. It was not apparent that PSCA was internalization-competent. In addition, the ability of an antibody to internalize depends on several factors including the affinity, avidity, and isotype of the antibody, and the epitope that it binds. We have demonstrated herein that the GPI-linked, cell surface PSCA is internalization competent upon binding by the anti-PSCA antibodies of the invention. Additionally, it was demonstrated that the anti-PSCA antibodies of the present invention can specifically target PSCA-expressing tumor cells in vivo and inhibit or kill these cells. These in vivo tumor targeting, internalization and growth inhibitory properties of the anti-PSCA antibodies make these antibodies very suitable for therapeutic uses, e.g., in the treatment of various cancers including prostate, urinary tract and lung cancer. Internalization of the anti-PSCA antibody is preferred, e.g., if the antibody or antibody conjugate has an intracellular site of action and if the cytotoxic agent conjugated to the antibody does not readily cross the plasma (e.g., the toxin, calicheamicin). Internalization is not necessary if the antibodies or the agent conjugated to the antibodies do not have intracellular sites of action, e.g., if the antibody can kill the tumor cell by ADCC or some other mechanism.

The anti-PSCA antibodies of the invention also have various non-therapeutic applications. In view of the fact that the use of PSA as a tool for screening or diagnosing prostate cancer is controversial, the anti-PSCA antibodies of the present invention can be useful for diagnosis and staging of PSCA-expressing cancers (e.g., in radioimaging). The antibodies are also useful for purification or immunoprecipitation of PSCA from cells, for detection and quantitation of PSCA in vitro, e.g. in an ELISA or a Western blot, to kill and eliminate PSCA-expressing cells from a population of mixed cells as a step in the purification of other cells.

The internalizing anti-PSCA antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies an antibody sequence is fused to a heterologous polypeptide sequence. The antibodies can be modified in the Fc region to provide desired effector functions. As discussed in more detail in the sections below, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

In one embodiment, the antibody competes for binding or bind substantially to, the same epitope as the antibodies of the invention. Antibodies having the biological characteristics of the present anti-PSCA antibodies of the invention are also contemplated, e.g., an anti-PSCA antibody which has the biological characteristics of a monoclonal antibody produced by the hybridomas accorded ATCC accession numbers PTA-717, PTA-718, PTA-719, PTA-720, PTA-880, PTA-2265, or PTA-2264, specifically including the in vivo tumor targeting, internalization and any cell proliferation inhibition or cytotoxic characteristics.

Specifically provided are anti-PSCA antibodies that bind to an epitope present in amino acids 21-40, or 41-60, or 61-80, or 81-100 of human PSCA, shown in SEQ ID NO.1.

Methods of producing the above antibodies are described in detail below.

The present anti-PSCA antibodies are useful for treating a PSCA-expressing cancer or alleviating one or more symptoms of the cancer in a mammal. Such a cancer includes prostate cancer, cancer of the urinary tract, lung cancer, breast cancer, colon cancer and ovarian cancer, more specifically, prostate adenocarcinoma, renal cell carcinomas, colorectal adenocarcinomas, lung adenocarcinomas, lung squamous cell carcinomas, and pleural mesothelioma. The cancers encompass metastatic cancers of any of the preceding, e.g., prostate cancer metastases. The antibody is able to bind to at least a portion of the cancer cells that express PSCA in the mammal and preferably is one that does not induce or that minimizes HAMA response. In a preferred embodiment, the antibody is effective to destroy or kill PSCA-expressing tumor cells or inhibit the growth of such tumor cells, in vitro or in vivo, upon binding to PSCA on the cell. Such an antibody includes a naked anti-PSCA antibody (not conjugated to any agent). Naked anti-PSCA antibodies having tumor growth inhibition properties in vivo include the antibodies described in the Experimental Examples below. Naked antibodies that have cytotoxic or cell growth inhibition properties can be further harnessed with a cytotoxic agent to render them even more potent in tumor cell destruction. Cytotoxic properties can be conferred to an anti-PSCA antibody by, e.g., conjugating the antibody with a cytotoxic agent, to form an immunoconjugate as described below. The cytotoxic agent or a growth inhibitory agent is preferably a small molecule. Toxins such as calicheamicin or a maytansinoid and analogs or derivatives thereof, are preferable.

The invention provides a composition comprising an anti-PSCA antibody of the invention, and a carrier. For the purposes of treating cancer, compositions can be administered to the patient in need of such treatment, wherein the composition can comprise one or more anti-PSCA antibodies present as an immunoconjugate or as the naked antibody. In a further embodiment, the compositions can comprise these antibodies in combination with other therapeutic agents such as cytotoxic or growth inhibitory agents, including chemotherapeutic agents. The invention also provides formulations comprising an anti-PSCA antibody of the invention, and a carrier. In one embodiment, the formulation is a therapeutic formulation comprising a pharmaceutically acceptable carrier.

Another aspect of the invention is isolated nucleic acids encoding the internalizing anti-PSCA antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a PSCA-expressing cancer or alleviating one or more symptoms of the cancer in a mammal, comprising administering a therapeutically effective amount of an internalizing anti-PSCA antibody to the mammal. The antibody therapeutic compositions can be administered short term (acute) or chronic, or intermittent as directed by physician. Also provided are methods of inhibiting the growth of, and killing a PSCA expressing cell.

Finally, the invention also provides kits and articles of manufacture comprising at least one internalizing anti-PSCA antibody. Kits containing anti-PSCA antibodies find use e.g., for PSCA cell killing assays, for purification or immunoprecipitation of PSCA from cells. For example, for isolation and purification of PSCA, the kit can contain an anti-PSCA antibody coupled to beads (e.g., sepharose beads). Kits can be provided which contain the antibodies for detection and quantitation of PSCA in vitro, e.g. in an ELISA or a Western blot. Such antibody useful for detection may be provided with a label such as a fluorescent or radiolabel.

III. Production of Anti-PSCA Antibodies

The following describes exemplary techniques for the production of the antibodies useful in the present invention. Some of these techniques are described further in Example 1 and Table 2A. The PSCA antigen to be used for production of antibodies may be, e.g., the full length polypeptide or a portion thereof, including a soluble form of PSCA lacking the GPI anchor sequence (which can be obtained by enzymatic cleavage with phosphatidylinositol phospholipases), or synthetic peptides to selected portions of the protein. Alternatively, cells expressing PSCA at their cell surface (e.g. CHO or NIH-3T3 cells transformed to overexpress PSCA; prostate or other PSCA-expressing tumor cell line), or membranes prepared from such cells can be used to generate antibodies. The nucleotide and amino acid sequences of human and murine PSCA are available as provided above. PSCA can be produced recombinantly in and isolated from, bacterial or eukaryotic cells using standard recombinant DNA methodology. PSCA can be expressed as a tagged (e.g., epitope tag) or other fusion protein to facilitate isolation as well as identification in various assays. Antibodies or binding proteins that bind to various tags and fusion sequences are available as elaborated below. Other forms of PSCA useful for generating antibodies will be apparent to those skilled in the art.

Tags

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. The FLAG-peptide [Hopp et al., *BioTechnology*, 6:1204-1210 (1988)] is recognized by an anti-FLAG M2 monoclonal antibody (Eastman Kodak Co., New Haven, Conn.). Purification of a protein containing the FLAG peptide can be performed by immunoaffinity chromatography using an affinity matrix comprising the anti-FLAG M2 monoclonal antibody covalently attached to agarose (Eastman Kodak Co., New Haven, Conn.). Other tag polypeptides include the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

(ii) Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp.59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp.51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp.59-103 (Academic Press, 1986)). Suitable culture media for this purpose include, for example, D-MEM or RPMI-1640 medium. In addition, the hybridoma cells may be grown in vivo as ascites tumors in an animal e.g, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Pluckthun, Immunol. Revs., 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl. Acad. Sci. USA*, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Reichmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-PSCA antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggemann et al., *Year in Immuno.*, 7:33 (1993); U.S. Pat. Nos. 5,545,806, 5,569,825, 5,591,669 (all of GenPharm); U.S. Pat. No. 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

(v) Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869, 046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641, 870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the PSCA protein. Other such antibodies may combine an PSCA binding site with a binding site for another protein. Alternatively, an anti-PSCA arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the PSCA-expressing cell. Bispecific antibodies may also be used to localize cytotoxic agents to cells which express PSCA. These antibodies possess a PSCA-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci USA*, 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

(vii) Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a $C_L$ domain.

(viii) Other Amino Acid Sequence Modifications

Amino acid sequence modification(s) of the anti-PSCA antibodies described herein are contemplated. For example, it may be desirable to improve the binding affinity and/or other biological properties of the antibody. Amino acid sequence variants of the anti-PSCA antibody are prepared by introducing appropriate nucleotide changes into the anti-PSCA antibody nucleic acid, or by peptide synthesis. Such modifications include, for example, deletions from, and/or insertions into and/or substitutions of, residues within the amino acid sequences of the anti-PSCA antibody. Any combination of deletion, insertion, and substitution is made to arrive at the final construct, provided that the final construct possesses the desired characteristics. The amino acid changes also may alter post-translational processes of the anti-PSCA antibody, such as changing the number or position of glycosylation sites.

A useful method for identification of certain residues or regions of the anti-PSCA antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with PSCA antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-PSCA antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-PSCA antibody with an N-terminal methionyl residue or the antibody fused to a cytotoxic polypeptide. Other insertional variants of the anti-PSCA antibody molecule include the fusion to the N- or C-terminus of the anti-PSCA antibody to an enzyme (e.g. for ADEPT) or a polypeptide which increases the serum half-life of the antibody.

Another type of variant is an amino acid substitution variant. These variants have at least one amino acid residue in the anti-PSCA antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the anti-PSCA antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human PSCA. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-PSCA antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-PSCA antibody.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

(ix) Screening for Antibodies with the Desired Properties

Techniques for generating antibodies have been described above. One may further select antibodies with certain biological characteristics, as desired.

The growth inhibitory effects of an anti-PSCA antibody of the invention may be assessed by methods known in the art, e.g., using cells which express PSCA either endogenously or following transfection with the PSCA gene. For example, the tumor cell lines and PSCA-transfected cells provided in Example 2 below may treated with an anti-PSCA monoclonal antibody of the invention at various concentrations for a few days (e.g., 2-7) days and stained with crystal violet or MTT or analyzed by some other colorimetric assay. Another method of measuring proliferation would be by comparing 3H-thymidine uptake by the cells treated in the presence or absence an anti-PSCA antibody of the invention. After antibody treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways such as is described in the Experimental Examples section below (see Example 6). Preferably, the tumor cell is one that over-expresses PSCA. Preferably, the anti-PSCA antibody will inhibit cell proliferation of a PSCA-expressing tumor cell in vitro or in vivo by about 25-100% compared to the untreated tumor cell, more preferably, by about 30-100%, and even more preferably by about 50-100% or 70-100%, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-PSCA antibody at about 1 µg/kg to about 100 mg/kg body weight results in reduction in tumor size or tumor cell proliferation within about 5 days to 3 months from the first administration of the antibody, preferably within about 5 to 30 days.

To select for antibodies which induce cell death, loss of membrane integrity as indicated by, e.g., propidium iodide (PI), trypan blue or 7AAD uptake may be assessed relative to control. A PI uptake assay can be performed in the absence of complement and immune effector cells. PSCA-expressing tumor cells are incubated with medium alone or medium containing of the appropriate monoclonal antibody at e.g, about 10 µg/ml. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those antibodies which induce statistically significant levels of cell death as determined by PI uptake may be selected as cell death-inducing antibodies.

To screen for antibodies which bind to an epitope on PSCA bound by an antibody of interest, a routine cross-blocking assay such as that described in *Antibodies, A Laboratory Manual*, Cold Spring Harbor Laboratory, Ed Harlow and David Lane (1988), can be performed. This assay can be used to determine if a test antibody binds the same site or epitope as an anti-PSCA antibody of the invention. Alternatively, or additionally, epitope mapping can be performed by methods known in the art. For example, the antibody sequence can be mutagenized such as by alanine scanning, to identify contact residues. The mutant antibody is initailly tested for binding with polyclonal antibody to ensure proper folding. In a different method, peptides corresponding to different regions of PSCA can be used in competition assays with the test antibodies or with a test antibody and an antibody with a characterized or known epitope.

(x) Immunoconjugates

The invention also pertains to therapy with immunoconjugates comprising an antibody conjugated to an anti-cancer agent such as a cytotoxic agent or a growth inhibitory agent.

Chemotherapeutic agents useful in the generation of such immunoconjugates have been described above.

Conjugates of an antibody and one or more small molecule toxins, such as a calicheamicin, maytansinoids, a trichothene, and CC1065, and the derivatives of these toxins that have toxin activity, are also contemplated herein.

A. Maytansine and Maytansinoids

In one preferred embodiment, an anti-PSCA antibody (full length or fragments) of the invention is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

B. Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al. *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

C. Anti-PSCA Antibody-Maytansinoid Conjugates (Immunoconjugates)

Anti-PSCA antibody-maytansinoid conjugates are prepared by chemically linking an anti-PSCA antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al. *Cancer Research* 52: 127-131 (1992). The linking groups include disufide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., *Biochem. J.* 173:723-737 [1978]) and N-succinimidyl-4-(2-pyridylthio)pentanoate (SPP) to provide for a disulfide linkage. See Example 7 below.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. In a preferred embodiment, the linkage is formed at the C-3 position of maytansinol or a maytansinol analogue.

Calicheamicin

Another immunoconjugate of interest comprises an anti-PSCA antibody conjugated to one or more calicheamicin molecules. The calicheamicin family of antibiotics are capable of producing double-stranded DNA breaks at subpicomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I, \gamma_2^I, \gamma_3^I$, N-acetyl-$\gamma_1^I$, PSAG and $\theta^I_1$ (Hinman et al. *Cancer Research* 53: 3336-3342 (1993), Lode et al. *Cancer Research* 58: 2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-PSCA antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-PSCA antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al. *Cancer Research* 52: 127-131 (1992); U.S. Pat. No. 5,208,020) may be used.

Alternatively, a fusion protein comprising the anti-PSCA antibody and cytotoxic agent may be made, e.g. by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(xi) Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuramimidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The enzymes of this invention can be covalently bound to the anti-PSCA antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature,* 312: 604-608 (1984)).

(xi) Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980).

The anti-PSCA antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA,* 82:3688 (1985); Hwang et al., *Proc. Natl. Acad. Sci. USA,* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.*81(19)1484 (1989).

IV. Vectors, Host Cells and Recombinant Methods

The invention also provides isolated nucleic acid encoding the humanized anti-PSCA antibody, vectors and host cells comprising the nucleic acid, and recombinant techniques for the production of the antibody.

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The anti-PSCA antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native anti-PSCA antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the anti-PSCA antibody.

(ii) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the anti-PSCA antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding anti-PSCA antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

(iv) Promoter Component

Expression and cloning vectors usually contain a promoter that is recognized by the host organism and is operably linked to the anti-PSCA antibody nucleic acid. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-PSCA antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-PSCA antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419, 446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(v) Enhancer Element Component

Transcription of a DNA encoding the anti-PSCA antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the anti-PSCA antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-PSCA antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis (e.g., B. licheniformis 41P disclosed in DD 266,710 published 12 Apr. 1989), Pseudomonas such as P. aeruginosa, and Streptomyces. One preferred E. coli cloning host is E. coli 294 (ATCC 31,446), although other strains such as E. coli B, E. coli X1776 (ATCC 31,537), and E. coli W3110 (ATCC 27,325) are suitable. These examples are illustrative rather than limiting.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in E. coli is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.) which describes translation initiation regio (TIR) and signal sequences for optimizing expression and secretion, these patents incorporated herein by reference. After expression, the antibody is isolated from the E. coli cell paste in a soluble fraction and can be purified through, e.g., a protein A or G column depending on the isotype. Final purification can be carried out similar to the process for purifying antibody expressed e.g, in CHO cells.

In addition to prokaryotes, eukaryotic microbes such as filamentous fungi or yeast are suitable cloning or expression hosts for anti-PSCA antibody-encoding vectors. Saccharomyces cerevisiae, or common baker's yeast, is the most commonly used among lower eukaryotic host microorganisms. However, a number of other genera, species, and strains are commonly available and useful herein, such as Schizosaccharomyces pombe; Kluyveromyces hosts such as, e.g., K. lactis, K. fragilis (ATCC 12,424), K. bulgaricus (ATCC 16,045), K. wickeramii (ATCC 24,178), K. waltii (ATCC 56,500), K. drosophilarum (ATCC 36,906), K. thermotolerans, and K. marxianus; yarrowia (EP 402,226); Pichia pastoris (EP 183, 070); Candida; Trichoderma reesia (EP 244,234); Neurospora crassa; Schwanniomyces such as Schwanniomyces occidentalis; and filamentous fungi such as, e.g., Neurospora, Penicillium, Tolypocladium, and Aspergillus hosts such as A. nidulans and A. niger.

Suitable host cells for the expression of glycosylated anti-PSCA antibody are derived from multicellular organisms. Examples of invertebrate cells include plant and insect cells. Numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruitfly), and Bombyx mori have been identified. A variety of viral strains for transfection are publicly available, e.g., the L-1 variant of Autographa californica NPV and the Bm-5 strain of Bombyx mori NPV, and such viruses may be used as the virus herein according to the present invention, particularly for transfection of Spodoptera frugiperda cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for anti-PSCA antibody production and cultured in conventional nutrient media modified as appropriate for inducing promoters, selecting transformants, or amplifying the genes encoding the desired sequences.

(viii) Culturing the Host Cells

The host cells used to produce the anti-PSCA antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.*102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Anti-PSCA Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

V. Pharmaceutical Formulations

Therapeutic formulations of the antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). The antibody preferably comprises the antibody at a concentration of between 5-200 mg/ml, preferably between 10-100 mg/ml.

The formulation herein may also contain more than one active compound as necessary for the particular indication being treated, preferably those with complementary activities that do not adversely affect each other. For example, in addition to the anti-PSCA antibody which internalizes, it may be desirable to include in the one formulation, an additional antibody, e.g. a second anti-PSCA antibody which binds a different epitope on PSCA, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

VI. Treatment with the Anti-PSCA Antibodies

According to the present invention, the anti-PSCA antibody that internalizes upon binding PSCA on a cell surface is used to treat a PSCA-expressing cancer cell, in particular, bladder and prostate cancer, such as androgen independent prostate cancer or androgen dependent prostate cancer, and associated metastases. A patient may be diagnosed as having androgen independent prostate cancer in that he no longer responds to anti-androgen therapy and the patient diagnosed as having androgen dependent prostate cancer may be one who responds to anti-androgen therapy. The cancer will generally comprise PSCA-expressing cells, such that the anti-PSCA antibody is able to bind thereto. While the cancer may be characterized by overexpression of the PSCA molecule, the present application further provides a method for treating cancer which is not considered to be an PSCA-overexpressing cancer.

To determine PSCA expression in the cancer, various diagnostic assays are available. In one embodiment, PSCA overexpression may be analyzed by immunohistochemistry (IHC). Parrafin embedded tissue sections from a tumor biopsy may be subjected to the IHC assay and accorded a PSCA protein staining intensity criteria as follows:

Score 0 no staining is observed or membrane staining is observed in less than 10% of tumor cells.

Score 1+a faint/barely perceptible membrane staining is detected in more than 10% of the tumor cells.

The cells are only stained in part of their membrane.

Score 2+a weak to moderate complete membrane staining is observed in more than 10% of the tumor cells.

Score 3+a moderate to strong complete membrane staining is observed in more than 10% of the tumor cells.

Those tumors with 0 or 1+scores for PSCA expression may be characterized as not overexpressing PSCA, whereas those tumors with 2+ or 3+scores may be characterized as overexpressing PSCA.

Alternatively, or additionally, FISH assays such as the INFORM™ (sold by Ventana, Ariz.) or PATHVISION™ (Vysis, Ill.) may be carried out on formalin-fixed, paraffin-embedded tumor tissue to determine the extent (if any) of PSCA overexpression in the tumor.

PSCA overexpression or amplification may be evaluated using an in vivo diagnostic assay, e.g. by administering a molecule (such as an antibody) which binds the molecule to be detected and is tagged with a detectable label (e.g. a radioactive isotope or a fluorescent label) and externally scanning the patient for localization of the label.

Currently, depending on the stage of the cancer, prostate cancer treatment involves one or a combination of the following therapies: surgery to remove the cancerous tissue, radiation therapy, androgen deprivation (e.g., hormonal therapy), and chemotherapy. Anti-PSCA antibody therapy may be especially desirable in elderly patients who do not tolerate the toxicity and side effects of chemotherapy well, in metastatic disease where radiation therapy has limited usefulness, and for the management of prostatic carcinoma that is resistant to androgen deprivation treatment. The tumor targeting and internalizing anti-PSCA antibodies of the invention are useful to alleviate PSCA-expressing cancers, e.g. prostate and bladder cancers upon initial diagnosis of the disease or during relapse. For therapeutic applications, the anti-PSCA antibody can be used alone, or in combination therapy with, e.g., hormones, antiangiogens, or radiolabelled compounds, or with surgery, cryotherapy, and/or radiotherapy, notably for prostate cancers, also particularly where shed cells cannot be reached. Anti-PSCA antibody treatment can be administered in conjunction with other forms of conventional therapy, either consecutively with, pre- or post-conventional therapy. Chemotherapeutic drugs such as taxotere® (docetaxel), taxol® (palictaxel), estramustine and mitoxantrone are used in treating metastatic and hormone refractory prostate cancer, in particular, in good risk patients. In the present method of the invention for treating or alleviating cancer, in particular, androgen independent and/or metastatic prostate cancer, the cancer patient can be administered anti-PSCA antibody in conjuction with treatment with the one or more of the preceding chemotherapeutic agents. In particular, combination therapy with palictaxel and modified derivatives (see, e.g., EP0600517) is contemplated. The anti-PSCA antibody will be administered with a therapeutically effective dose of the chemotherapeutic agent. In another embodiment, the anti-PSCA antibody is administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In one particular embodiment, an immunoconjugate comprising the anti-PSCA antibody conjugated with a cytotoxic agent is administered to the patient. Preferably, the immunoconjugate bound to the PSCA protein is internalized by the cell, resulting in increased therapeutic efficacy of the immunoconjugate in killing the cancer cell to which it binds. In a preferred embodiment, the cytotoxic agent targets or interferes with the nucleic acid in the cancer cell. Examples of such cytotoxic agents are described above and include maytansinoids, calicheamicins, ribonucleases and DNA endonucleases.

The anti-PSCA antibodies or immunoconjugates are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

Other therapeutic regimens may be combined with the administration of the anti-PSCA antibody. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-PSCA antibody or antibodies, with administration of an antibody directed against another tumor antigen associated with the particular cancer.

In another embodiment, the antibody therapeutic treatment method of the present invention involves the combined administration of an anti-PSCA antibody (or antibodies) and one or more chemotherapeutic agents or growth inhibitory agents, including co-administration of cocktails of different chemotherapeutic agents. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/ or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-PSCA antibody (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody therapy. Suitable dosages for any of the above co-administered agents are those presently used and may be lowered due to the combined action (synergy) of the agent and anti-PSCA antibody.

For the prevention or treatment of disease, the dosage and mode of administration will be chosen by the physician according to known criteria. The appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 µg/kg to about 50 mg/kg body weight (e.g. about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-PSCA antibody. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., *Science* 256:808-813 (1992). See also WO 93/25673 and the references cited therein.

VII. Articles of Manufacture and Kits

Another embodiment of the invention is an article of manufacture containing materials useful for the treatment of anti-PSCA expressing cancer, in particular prostate cancer and bladder cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the cancer condition and may have a sterile access port (for example the container may be an intravenous solution bag or a vial having a stopper pierceable by a hypodermic injection needle). At least one active agent in the composition is an anti-PSCA antibody of the invention. The label or package insert indicates that the composition is used for treating prostate cancer, androgen independent prostate cancer, or androgen dependent prostate cancer, or bladder cancer. The label or package insert will further comprise instructions for administering the antibody composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for PSCA cell killing assays, for purification or immunoprecipitation of PSCA from cells. For isolation and purification of PSCA, the kit can contain an anti-PSCA antibody coupled to beads (e.g., sepharose beads). Kits can be provided which contain the antibodies for detection and quantitation of PSCA in vitro, e.g. in an ELISA or a Western blot. As with the article of manufacture, the kit comprises a container and a label or package insert on or associated with the container. The container holds a composition comprising at least one anti-PSCA antibody of the invention. Additional containers may be included that contain, e.g., diluents and buffers, control antibodies. The label or package insert may provide a description of the composition as well as instructions for the intended in vitro or diagnostic use.

VIII. EXPERIMENTAL EXAMPLES

The above and other features of the invention will now be described more particularly with reference to the accompanying figures and pointed out in the claims. The particular embodiments described below are provided by way of illustration and are not meant to be construed as a limitation on the scope of the invention. It will be apparent to one of ordinary skill in the art that many modifications can be made to the present invention without departing from the spirit or essential characteristics of the invention.

Example 1

The preparation and characterization of the anti-PSCA monoclonal antibodies are described.

I. Materials and Methods

Hybridomas producing murine and human anti-PSCA monoclonal antibodies (Mabs) were generated. The fusion partner was the mouse myeloma line P3X63Ag8.653 (Kearney, J. F. et al., *J. Immunology* 123:1548-1550, 1979).

Table 2A summarizes the immunization strategies and shows the nature of the antigen used for immunization, the adjuvant, dosage, route of administration, dosing schedule and host animal used. Table 2B summarizes the characteristics of the anti-PSCA Mabs as determined by various assays. The antibody names herein are derived from the first 3-4 characters of the hybridoma clone producing the antibody (see Table 2B). The first 3-4 characters before the period in the clone name indicate the parental clone followed after the first period by the name of further subclones, if any. Alternatively, the anti-PSCA antibodies herein are also referred to by their designated ascites number. Except where muPSCA is indicated, human (hu) PSCA by itself or fused to a gD tag (gDPSCA) or histidine tag (his-PSCA), was used. Human or murine PSCA expressed in *E. coli* was histidine-tagged. Unless otherwise indicated, PSCA expressed in *E. coli* was refolded, as described below, for immunization. gDPSCA-CHO refers to soluble PSCA expressed in and purified from CHO cells. Antibodies prepared from Xenomice (Abgenix, Fremont, Calif.) are fully human antibodies.

For the hu PSCA nucleotide and amino acid sequences, refer to WO 99/14328 (Genentech; PRO232 protein, nucleotide sequence in FIG. 1; amino acid sequence in FIG. 2); U.S. Pat. No. 5,856,136 issued Jan. 5, 1999 (Incyte; SCAH2 SEQ ID4); or FIG. 2 on page 1737 of Reiter et al. *Proc. Nat. Acad. Sci.* 95:1735-1740 (1998). For convenience, the 123 amino acid sequence and the coding sequence of the cDNA of PSCA are provided herein as SEQ ID NO. 1 and SEQ ID NO. 2, respectively. The numbering of the amino acid sequence referred to herein will be according to that shown in SEQ ID NO. 1 which is the same as in Reiter et al. (1998).

Cell Lines and Transfections

A plasmid vector encoding hu PSCA or gDPSCA was transfected into the following cells: NIH 3T3 cells expressing Ras (Ras 3T3); and CHO; HCT116. For expression in *E. coli*, the sequence encoding hu PSCA amino acids 10-101 was used (fused to a His tag), with the GPI anchor sequence removed. For expression in 3T3 cells, the N-terminal signal sequence (aa 1-20) of PSCA was replaced by the signal sequence of the gD tag followed by 25 amino acids of the mature gD.

Binding Assays

The anti-PSCA antibodies were analyzed for binding to PSCA on cells by Fluorescence Activated Cell Sorter (FACS). Purified murine anti-PSCA 6B8.1D7.2B3 (#2761) antibody and fully human anti-PSCA 10C5.6E4.6D1 (#2910) antibody from hybridoma supernatant were analyzed for cell surface binding by FACS. Confluent adherent stable CHO cells transfected with huPSCA with a gD tag at its N-terminus were washed with PBS and detached using Cell Dissociation Solution (Sigma). Cells were incubated with the anti-PSCA antibodies at various concentrations (1-10 µg/ml) and washed with PBS prior to incubation with a FITC conjugated secondary antibody. Cells were resuspended in PBS containing 1% FBS or 1% formaldehyde for cell fixation. The binding of antibodies to the cell surface was then analyzed on a FACScan.

To assess the ability of the Mabs to capture PSCA in solution, an assay was developed in which each antibody was either directly coated onto microtiter plates or bound to an anti-mouse IgG specific to the Fc region, previously coated on the plate. Biotinylated PSCA antigen (1 µg/ml) was then added to the plate prior to incubation with streptavidin-HRP. OPD was used as a substrate and plates were read at 492 nm.

Figure 4:
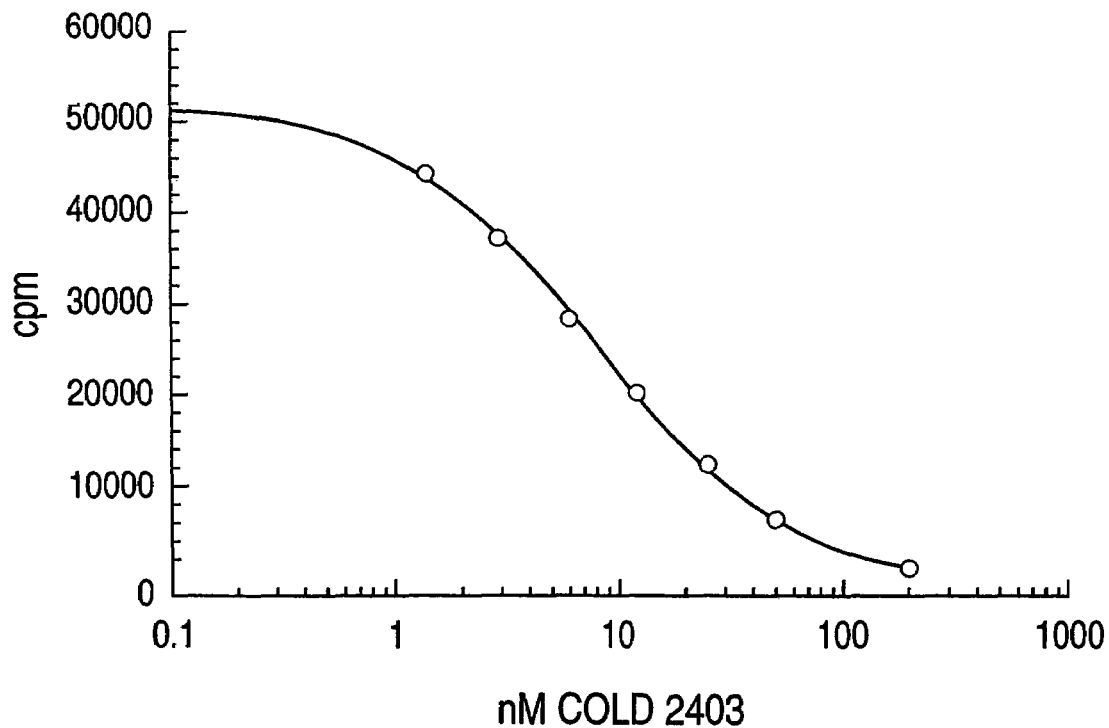
FIG. 4 shows the binding curve for antibody ascites no. 2403 (5F2) (see Example 1).
Figure 5:
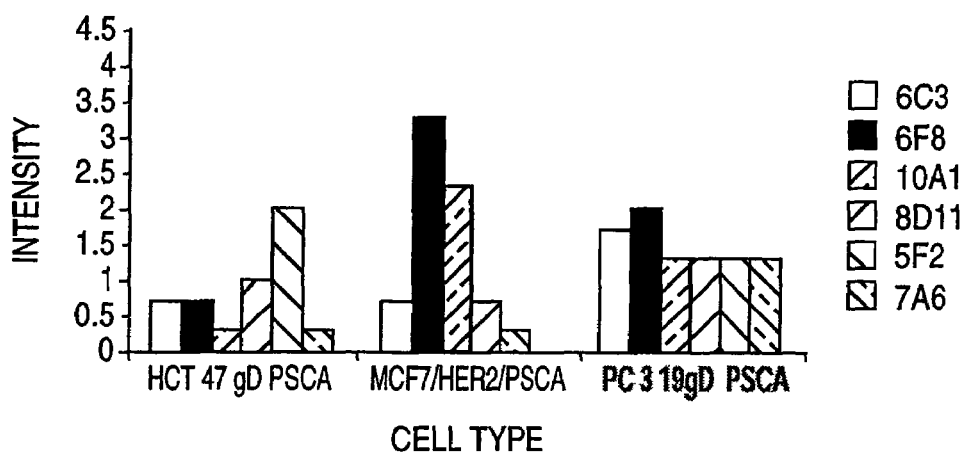
FIG. 5 is a graph showing internalization of the different anti-PSCA monoclonal antibodies (6C3; 6F8; 10A1; 8D11; 5F2; 7A6) in the three cell types, as measured within 1 hour, by the intensity of the Cy3 fluorescence (see Example 3).
Figure 6:
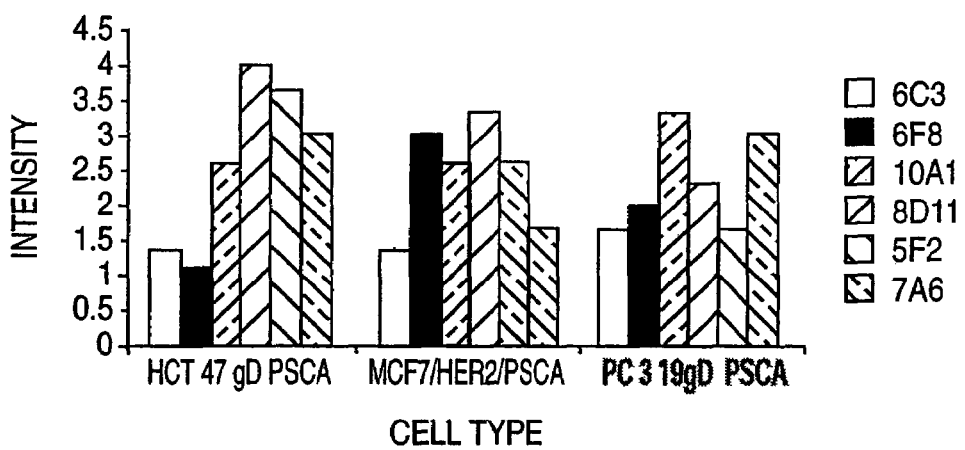
FIG. 6 is a graph showing surface labeling of PSCA by the different anti-PSCA monoclonal antibodies (6C3; 6F8; 10A1; 8D11; 5F2; 7A6) on the three cell types, as measured by the intensity of the Cy3 fluorescence (see Example 3).
Figure 7:
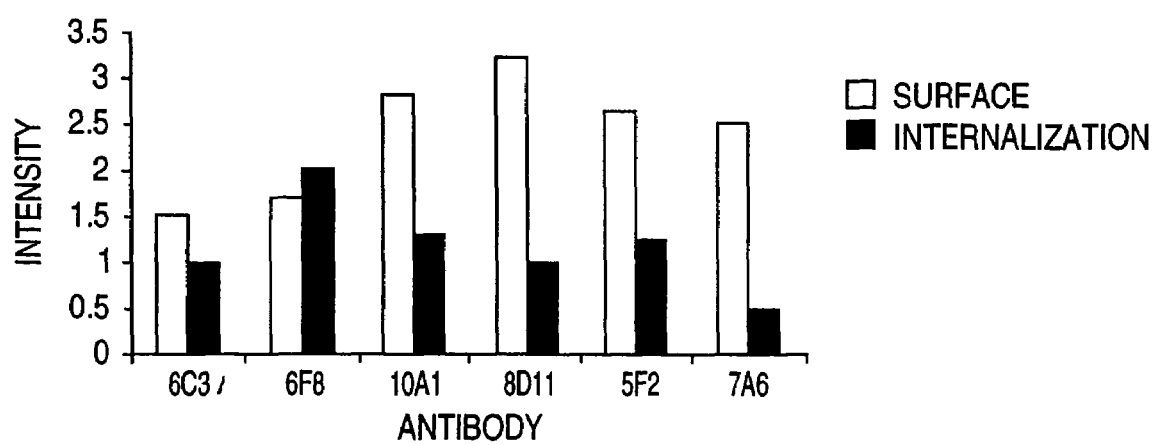
FIG. 7 is a graph comparing the amount of surface versus internalized anti-PSCA monoclonal antibody for each of the antibodies as measured within 1 hour, by the intensity of the Cy3 fluorescence. The amount of surface and internalized antibody is an average of the results from the three different cell lines used in FIGS. 5 and 6.
Figure 8A:
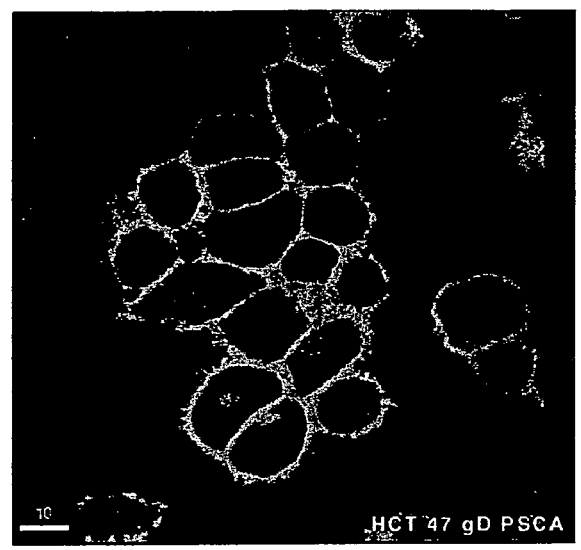
FIGS. 8A, 8B and 8C are micrographs showing the distribution of the fluorescent labeled 8D11 anti-PSCA antibody in PSCA-expressing cell lines HCT 47 gD, MCF7/HER2/PSCA, and PC3 19 gD PSCA respectively, as observed by confocal microscopy (See Example 3).
Figure 8B:
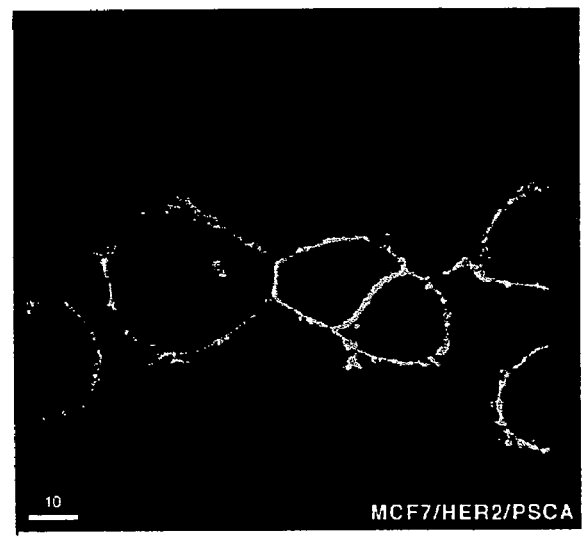
Figure 8C:
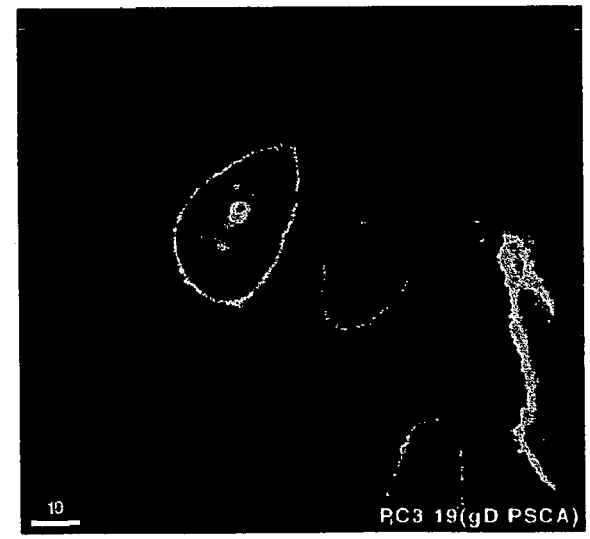
Figure 9A:
FIGS. 9A-D show electron micrographs of CHO cells expressing PSCA treated with anti-PSCA antibodies labeled with gold adducts.
Figure 9B:
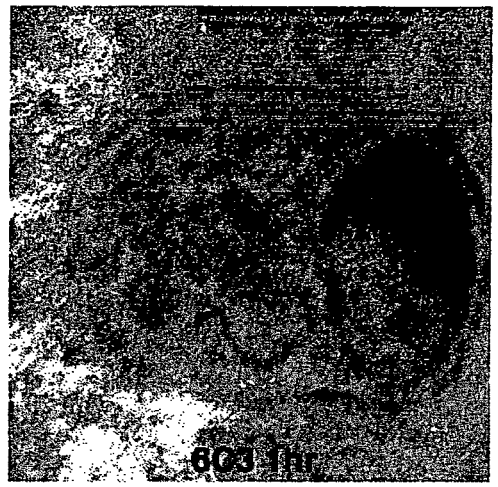
Figure 9C:
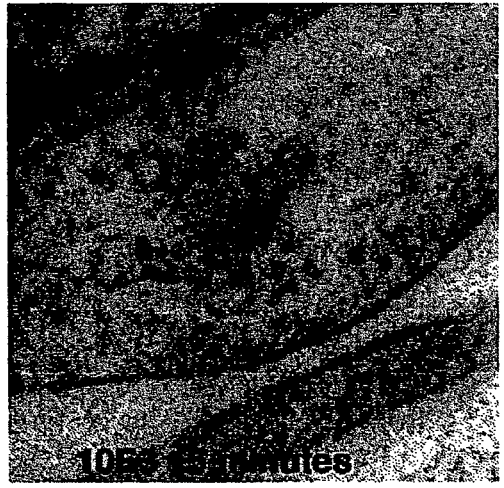
Figure 9D:
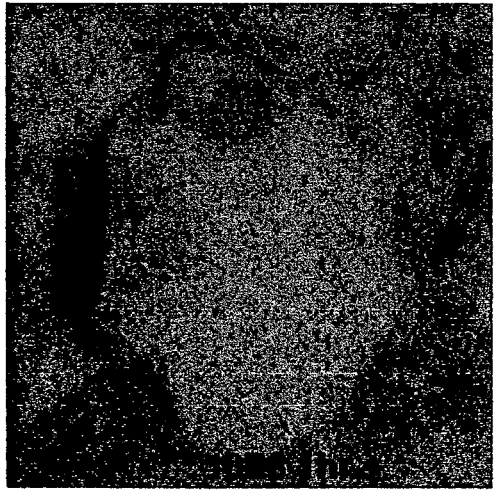

To verify the binding of Mab #2403 to PSCA expressed on the surface of transfected cells, a cold competition binding assay was performed using $^{125}$I-labeled Mab #2403 (lactoperoxidase method). PC3.gD.hu PSCA cells ($1\times10^5$) were plated in a 24 well dish and incubated in medium with various concentrations of unlabeled Mab 2403 and a constant amount of $^{125}$I-Mab 2403 for 16 hours at 4° C. Unbound antibody was removed and cells were washed with ice-cold medium. After solubilization of the cells in 8M Urea/3M glacial acetic acid, the amount of radioactivity bound was determined using a gamma counter. The $IC_{50}$ value was calculated from a four parameter fit calculation of the curve where m3 represent the $IC_{50}$. The results of this assay are plotted in FIG. 4.

A direct ELISA was performed to determine the binding activity of the #2761 (6B8) antibody. HuPSCA and murine PSCA (mPSCA) were coated overnight at 1 µg/ml onto a microtiter plate (Nunc). The anti-PSCA Mab and controls were added to the antigen-coated wells and incubated at room temperature. Unbound antibody was washed off and a horseradish peroxidase (HRP)-conjugated secondary antibody was added to the wells and incubated with the antibodies at room temperature. OPD substrate solution was finally added and concentrated sulfuric acid was used to stop the reaction. The plate was read at 492 nm using a microtiter plate reader.

Epitope groupings were determined by competitive ELISA. Each antibody was biotinylated and tested for binding to PSCA coated on plates, in the presence or absence of an excess of each unlabeled anti-PSCA Mab. Streptavidin-HRP was then added to the plates followed by peroxidase substrate. Decrease (at least 50%) or lack of binding of biotinylated Mabs to PSCA indicated that both cold and biotinylated antibodies bound to the same (or proximal) epitope on PSCA.

Purification and Refolding of His-Tagged Proteins Produced in E. coli

The following procedure has been adapted for use on proteins produced from 0.5 to 1 L fermentations of E. coli expressing His-tagged proteins. It can easily be scaled to much larger amounts.

E. coli paste from 0.5 to 1 L fermentations (6-10 gm pellets) was resuspended in 10 volumes (w/v) in 7M guanidine, 20 mM Tris, pH 8 buffer. Solid sodium sulfite and sodium tetrathionate were added to make final concentrations of 0.1M and 0.02 M, respectively, and the solution was stirred overnight at 4° C. This step results in a denatured protein with all cysteine residues blocked by sulfitolization. The solution was centrifuged at 40 K rpm in a Beckman Ultracentrifuge for 30 min. The supernatant was diluted with 3-5 volumes of metal chelate column buffer (6 M guanidine, 20 mM Tris, pH 7.4) and filtered through 0.22 micron filters to clarify. Depending on the expression of the desired protein, 30-50 mls of the clarified extract were loaded onto a 5 ml Qiagen Ni-NTA metal chelate column equilibrated in the metal chelate column buffer. The column was washed with additional buffer containing 50 mM imidazole (Calbiochem, Utrol grade), pH 7.4. The protein was eluted with buffer containing 250 mM imidazole. Fractions containing the desired protein were pooled and stored at 4° C. Protein concentration was estimated by its absorbance at 280 nm using the calculated extinction coefficient based on its amino acid sequence.

The proteins are usually refolded by diluting sample slowly into freshly prepared refolding buffer consisting of: 20 mM Tris, pH 8.6, 0.3 M NaCl, 2.5 M urea, 5 mM cysteine, 20 mM glycine and 1 mM EDTA. In the case of PSCA, 3.5M Urea and 1 mM cysteine were used instead of 2.5 M Urea and 5 mM cysteine. Refolding volumes were chosen so that the final protein concentration would be between 50 to 100 micrograms/ml. The refolding solution was stirred gently at 4° C. for 12-36 hours. The refolding reaction was quenched by the addition of trifluoroacetic acid (TFA) to a final concentration of 0.4% (pH of approximately 3). Before further purification of the protein, the solution was filtered through a 0.22 micron filter and acetonitrile added to 2-10% final concentration. The refolded protein was chromatographed on a Vydac C4 reversed phase column using a mobile buffer of 0.1% TFA with elution with a gradient of acetonitrile from 10% to 80%. Aliquots of fractions with A280 absorbance were analyzed on SDS polyacrylamide gels and fractions containing homogeneous refolded protein were pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded protein were pooled and the acetonitrile removed using a gentle stream of nitrogen directed at the solution. Proteins were usually formulated into 20 mM Hepes, pH 6.8 with 0.14 M NaCl and 4% mannitol by dialysis or by gel filtration using G25 Superfine (Pharmacia) resins equilibrated in the formulation buffer and sterile filtered. Occasionally, proteins with isoelectric points in the pH range of 6-7.5 would be formulated in a buffer of 1 mM HCl, 0.14 M NaCl to maintain solubility. Formulated proteins were aliquoted and frozen and stored at −80° C. The protein was subsequently characterized by SDS gels, amino acid analysis for quantitation of protein, evaluated for endotoxin levels by an endotoxin assay, N-terminal protein sequencing to establish identity of protein, mass spectrometry to establish integrity of protein and other analytical procedures as necessary or desired.

Immunoglobulin Sequences and Constructs

Purified antibodies were subjected to amino acid sequencing using established methods. The N-terminal sequence was obtained and from that, primers were designed to clone out the Ig variable region (V) sequences by RT-PCR. The DNA fragment encoding the $V_L$ or $V_H$ region was cloned into a vector. Sequencing was performed using established methods, initially with primers to the vector. From the initial nucleotide sequence of the antibody that was obtained, primers specific to the antibody sequence were designed to obtain the remaining sequence.

The chimeric full length and Fab mouse-human anti-PSCA antibodies whose sequences are shown in FIG. 13 were constructed by joining the murine $V_L$ and $V_H$ region domain sequences to the human Cκ and Cγ1 sequences. The murine antibody V region fragments were cloned into vectors as restriction site cassettes which can be readily excised and ligated into preconstructed vectors containing human L and H constant regions of different isotypes to express chimeric mouse-human antibodies with PSCA specificity. The Fab chimeric chains were expressed from the vector called vegfchim derived from pUC119:Ig vector which is a pRK vector (described in EP 307,247).

FIG. 12 shows the amino acid sequences of the light and heavy chain variable region domains ($V_L$ and $V_H$) of the antibodies from hybridoma clones 6F8.2F4, Asc# 2395 (SEQ ID NO. 3 & NO. 4); 5F2.4H4.1E3, Asc# 2403 (SEQ ID NO. 5 & NO.6); 6B8.1D7.2B3, Asc#2761 (SEQ ID NO. 7 & NO. 8), and $V_H$ of the antibody from clone 8D11.2E9 (Asc# 2399 (SEQ ID NO. 9). FIG. 13 shows the amino acid sequences of the full length chimeric 2403 IgG including the signal peptide sequences (L chain is SEQ ID NO. 10; H chain is SEQ ID NO. 11) and the sequences of chimeric 6B8 Fab (L chain is SEQ ID NO. 12; H chain is SEQ ID NO. 13). Chimeric antibody 2403 was made by fusing the murine $V_L$ and $V_H$ sequences of Mab 5F2.4H4.1E3 (#2403) with human immunoglobulin Cκ and Cγ1 sequences, respectively, in the mammalian cell expression vector, pRK. The construction of the pRK5 expression vector is disclosed in EP 307,247 published Mar. 13, 1989. The pRK vectors encoding the chimeric 2403H and L chains have been deposited with the ATCC as DNA pRK-2403H and DNA pRK-2403L (see X below). Mouse $V_H$ was joined to human Cγ1 at sequential residue # Pro122 (denoted by/in sequence in FIG. 13). Mouse $V_L$ was joined to human $C_L$ at sequential residue # Arg113. The 2403 $V_H$ insert can be excised from pRK-2403H as an EcoRI-ApaI fragment or a ClaI-ApaI fragment of 430 bp. The 2403 $V_L$ was cloned into pRK-2403L as an EcoRI-CpoI fragment of 400 bp fragment. The pRK vectors encoding the chimeric 2761H and L chains have been deposited with the ATCC as DNA pRK-2761H and DNA pRK-2761L (see X below). Likewise, the 2761 $V_L$ has been cloned into pRK-2761L as an EcoRI-CpoI fragment of 400 bp fragment. The 2761 $V_H$ insert can be excised from pRK-2761H as an EcoRI-ApaI fragment or a ClaI-ApaI fragment of 430 bp.

Chimeric 6B8 Fab L and H chains were made by fusing the murine $V_L$ and $V_H$ sequences of Mab 6B8.1D7.2B3 with human immunoglobulin Cκ, and $C_H1$ domain of IgG1 sequences, respectively, in the vector called vegf4chim, and expressed in *E. coli*. The vegf4chim vector has an ampR selectable marker and the antibody sequences are operably linked to and expressed under, the alkaline phosphatase promoter.

These V region cassettes can be excised and ligated to constant region domains of the different human immunoglobulin isotypes to produce chimeras with different Fc properties. To produce anti-PSCA antibodies lacking effector funtions such as ADCC, complement binding activity or Fc receptor binding, the murine $V_H$ regions are fused to the human Cγ2 or Cγ4 contant region sequences.

II. Results

Table 2B summarizes the characteristics of the anti-PSCA antibodies as determined by the assays herein. In Table 2B, hu PSCA-*E. coli* refers to his-tagged PSCA expressed in *E. coli*; the protein was purified from the bacteria and then refolded as described above; +formalin indicates that formalin fixed cells were used as immunogen; prk5.hu PSCA refers to the naked cDNA carrying the hu PSCA gene in pRK5 plasmid. Xenomice (Abgenix, Fremont, Calif.) are mice which have been genetically engineered to replace their endogenous murine Ig locus with the human germline immunoglobulin locus such that they make human antibodies. Human antibodies to PSCA are made by immunizing the Xenomice with *E. coli* expressed PSCA, intraperitoneally (i.p.) or via the footpad.

All anti-PSCA Mabs tested produced a significant shift in staining of the PSCA-transfected cells as assayed by FACS. FIG. 1 (Mab 5F2) and FIG. 2 (Mab 10C5) show representative staining results. Cells incubated with FITC-conjugated secondary antibody alone was used as negative control; these cells did not show any antibody binding activity. The anti-gD Mab 1766 gD, used as a positive control, showed significant binding to CHO cells expressing gD-huPSCA. Hybridoma supernatant containing the fully human Mab 10C5.6E4.6D1 also demonstrated strong binding to the cell surface. Murine anti-PSCA Mab 5F2 (#2403) was used as a positive control in this experiment and media as a negative control.

Figure 3:
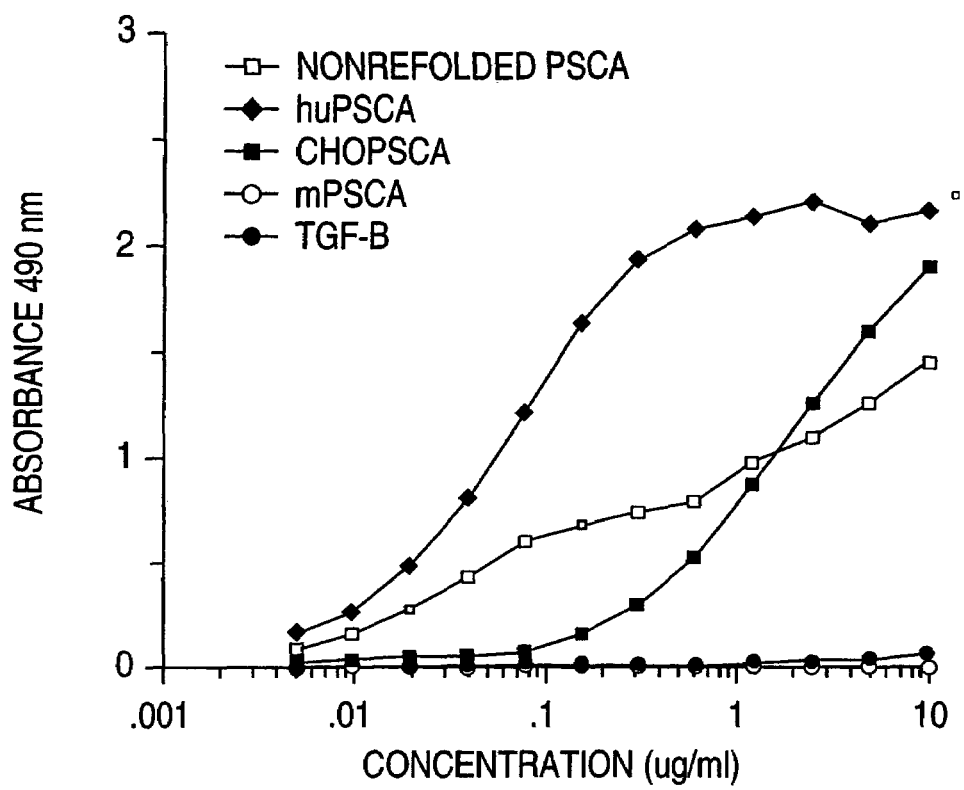
FIG. 3 shows the binding activity of the 6B8.1D7.2B3 anti-PSCA Mab to various soluble PSCA antigens (see Example 1).

Murine Mab 6B8 (#2761) was tested for its ability to bind to various soluble forms of PSCA immobilized onto a plate and the results are shown in FIG. 3. Mab 6B8 generated against denatured PSCA protein, demonstrated stronger affinity for the refolded huPSCA than for nonrefolded huPSCA. The Mab was also shown to bind to gD-huPSCA CHO soluble antigen, but with less affinity as compared to refolded and nonrefolded huPSCA. However, there was no binding to an irrelevant antigen TGF-β and murine PSCA, suggesting that the antibody was specific to huPSCA.

From the cold competition binding assay (see FIG. 4 and table immediately below), the binding affinity for the Mab 2403 was determined to be 12.9 nM.

| $y = ((m1 - m4)/(1 + (m0/m3)\hat{\ }m2)) + m4$ | | |
|---|---|---|
| | Value | Error |
| m1 | 40650 | 657.34 |
| m2 | 1.0449 | 0.074328 |
| m3 | 12.977 | 1.0636 |
| m4 | 1865 | 1102.9 |
| Chisq | 1.9794e+06 | NA |
| R | 0.99921 | NA |

TABLE 2A

| CLONE | MAbs ASC# | ANTIGEN | ADJUV. | DOSE | ROUTE | SCHEDULE | HOST |
|---|---|---|---|---|---|---|---|
| 10E3.5A7.1A7 | 2359 | hisPSCA - *E. coli* | Ribi | 5 ug | FP × 8 | 2/week | Balb/c |
| 6C3.4G12.1B7 | 2360 | hisPSCA - *E. coli* | " | 5 ug | " | " | Balb/c |
| 6F8.2F4 | 2395 | hisPSCA - *E. coli* | Ribi | 5 ug | FP × 6 | 2/week | Balb/c |
| 10A1.2F11 | 2396 | hisPSCA - *E. coli* | " | 5 ug | " | " | Balb/c |
| 2F2.2G7 | 2397 | hisPSCA - *E. coli* | " | 5 ug | " | " | Balb/c |
| 5B12.1C9 | 2398 | hisPSCA - *E. coli* | " | 5 ug | " | " | Balb/c |
| 8D11.2E9 | 2399 | hisPSCA - *E. coli* | " | 5 ug | " | " | Balb/c |
| 5A5.1D11 | 2400 | hisPSCA - *E. coli* | " | 5 ug | " | " | Balb/c |
| 2D2.1B12 | 2401 | hisPSCA - *E. coli* | " | 5 ug | " | " | Balb/c |
| 5F2.4H4.1E3 | 2403 | hisPSCA - *E. coli* | " | 5 ug | " | " | Balb/c |
| 7A6.1H4.2A5 | 2405 | hisPSCA - *E. coli* | " | 5 ug | " | " | Balb/c |
| 7B9.2C1.2H4.1D12 | 2429 | hisPSCA - *E. coli* | " | 5 ug | " | " | Balb/c |
| 12C5.1F10 | 2402 | hisPSCA - *E. coli* | Ribi | 5 ug | FP × 7 | 2/week | Balb/c |
| 2A4.3G2 | 2404 | hisPSCA - *E. coli* | " | 5 ug | " | " | Balb/c |
| 7B11.3H5.5C2 | 2430 | hisPSCA - *E. coli* | " | 5 ug | " | " | Balb/c |
| N/A | N/A | hisPSCA - *E. coli* | Ribi | 5 ug | FP × 6 | 2/week | Balb/c |
| N/A | N/A | gDPSCA Ras 3T3 | none | tumor | SQ | NA | Balb/c |
| N/A | N/A | gDPSCA - CHO membranes | Ribi | ND | FP × 6 | 1/week | Balb/c |
| 5G1.1E5 (S/N) | N/A | hisPSCA - *E. coli*/formalin | Ribi | 5 ug | FP × 10 | 2/week | Balb/c |
| N/A | N/A | gDPSCA - CHO | Ribi | 5 ug | FP × 10 | 1/week | Xenomice |
| N/A | N/A | hisPSCA - *E. coli* | Ribi | 5 ug | FP × 10 | 1/week | Xenomice |
| N/A | N/A | his Mu PSCA - *E. coli* | Ribi | 10 ug | FP × 10 | 1/week | Lewis rats |
| N/A | N/A | hisPSCA - *E. coli* | Ribi | 5 ug | FP × 5 | 1/week | Xenomice |
| N/A | N/A | hisPSCA - *E. coli* | Ribi | 10 ug | IP × 5 | 1/week | Xenomice |
| 4F9.1E8.1C2 (S/N) | 2760 | hisPSCA - *E. coli*/nonrefolded | Ribi | 5 ug | FP × 5 | 1/week | Balb/c |

TABLE 2A-continued

| CLONE | MAbs ASC# | ANTIGEN | ADJUV. | DOSE | ROUTE | SCHEDULE | HOST |
|---|---|---|---|---|---|---|---|
| 6B8.1D7.2B3 | 2761 | hisNonrefolded huPSCA - E. coli | Ribi | 5 ug | FP × 5 | 1/week | Balb/c |
| 3F9.1D4.2F1 (S/N) | 2759 | gDPSCA - CHO | Ribi | 5 ug | FP × 10 | 2/week | Balb/c |
| 2B12.1H6.1F9 (S/N) | 2758 | gDPSCA - CHO | Ribi | 5 ug | FP × 11 | 2/week | Balb/c |
| N/A | N/A | his Mu PSCA - E. coli | Ribi | 10 ug | FP × 5 | 1/week | Lewis rats |
| N/A | N/A | PSCA/GST - E. coli | Ribi | 5 ug | FP × 8 | 1/week | Balb/c |
| NO TITERS | N/A | hPSCA-1/KLH (peptide) | Ribi | 5 ug | FP × 7 | 1/week | Balb/C |
| NO TITERS | N/A | mPSCA-1/KLH (peptide) | Ribi | 5 ug | FP × 7 | 1/week | Lewis rats |
| 2 PARENTAL S/N | N/A | gDPSCA - HCT116 | none | 10 e6 | FP × 10 | 1/week | Balb/c |
| N/A | N/A | gDPSCA - HCT116/formalin | none | 10 e6 | FP × 10 | 1/week | Balb/c |
| NO TITERS | N/A | prk5.hu.PSCA (cDNA) | none | 100 ug | IM × 2 | 2/month | Balb/c |
| pending | pending | HCT116gDPSCA | none | 10 e6 | FP × 10 | 1/week | XenoMice |
| N/A | N/A | his Mu PSCA - E. coli | Ribi | 10 ug | FP × 5 | 1/week | Lewis Rats |
| N/A | N/A | hisPSCA - E. coli/nonrefolded | Ribi | 5 ug | FP × 5 | 1/week | XenoMice |
| N/A | N/A | PSCA/GST - E. coli | Ribi | 5 ug | FP × 6 | 1/week | Balb/c |
| 10C5.6E4.6D1 (S/N) | 2910 | hisPSCA-E. coli | Ribi | 5 ug | IP × 5 | 1/week | XenoMice |
| pending | pending | hisPSCA - E. coli/nonrefolded | Ribi | 5 ug | FP × 5 | 1/week | XenoMice |
| pending | pending | his Mu PSCA - E. coli | Ribi | 10 ug | FP × 5 | 1/week | Lewis Rats |
| pending | pending | PC3gDmPSCA Cells | none | 10 × 106 | FP × 10 | 1/week | Lewis Rats |

TABLE 2B

| CLONE | mAbs Asc# | ANTIGEN | SPECIES OR STRAIN | ISOTYPE | CAPTURE | FACS | IHC | EPITOPE | TUMOR TARGET | INTERNALIZE |
|---|---|---|---|---|---|---|---|---|---|---|
| 10E3.5A7.1A7 | 2359 | hu PSCA-E Coli | Balb/C | IgG1 | Yes | +/− | + | E | ND | Yes |
| 6C3.4G12.1B7 | 2360 | hu PSCA-E Coli | Balb/C | IgG2a | Yes | + | − | B | ND | Yes |
| 6F8.2F4 | 2395 | hu PSCA-E Coli | Balb/C | IgG2b | Yes | ++ | − | A | Yes | Yes |
| 10A1.2F11 | 2396 | hu PSCA-E Coli | Balb/C | IgG2b | Yes | + | − | A | ND | ND |
| 2F2.2G7 | 2397 | hu PSCA-E Coli | Balb/C | IgG2b | No | − | + | ND | ND | ND |
| 5B12.1C9 | 2398 | hu PSCA-E Coli | Balb/C | IgG2b | Yes | − | +/− | C | ND | ND |
| 8D11.2E9 | 2399 | hu PSCA-E Coli | Balb/C | IgG2b | Yes | ++ | − | A | Yes | Yes |
| 5A5.1D11 | 2400 | hu PSCA-E Coli | Balb/C | IgG2a | Yes | + | − | ND | ND | ND |
| 2D2.1B12 | 2401 | hu PSCA-E Coli | Balb/C | IgG2a | Yes | − | − | D | ND | ND |
| 5F2.4H4.1E3 | 2403 | hu PSCA-E Coli | Balb/C | IgG2b | Yes | ++ | − | A | Yes | Yes |
| 7A6.1H4.2A5 | 2405 | hu PSCA-E Coli | Balb/C | IgG2a | Yes | + | − | A | ND | ND |
| 7B9.2C1.2H4.1D12 | 2429 | hu PSCA-E Coli | Balb/C | IgG2a | Yes | − | − | F | ND | ND |
| 12C5.1F10 | 2402 | hu PSCA-E Coli | Balb/C | IgG2b | Yes | +/− | − | A | ND | ND |
| 2A4.3G2 | 2404 | hu PSCA-E Coli | Balb/C | IgG2b | No | − | − | ND | ND | ND |
| 7B11.3H5.5C2 | 2430 | hu PSCA-E Coli | Balb/C | IgG1 | Yes | +/− | +/− | ND | ND | ND |
| N/A | N/A | hu gDPSCA Ras 3T3 | Balb/C | | | | | | | |
| N/A | N/A | hu PSCA-CHO membrane | Balb/C | | | | | | | |
| 5G1.1E5 | N/A | hu PSCA-E Coli + formalin | Balb/C | IgM | ? | ? | − | | | |
| N/A | N/A | hu gDPSCA - CHO | Xenomice | N/A | N/A | N/A | N/A | | | |
| N/A | N/A | hu PSCA-E Coli | Xenomice | N/A | N/A | N/A | N/A | | | |
| pending | N/A | muPSCA-E. coli | Lewis rats | IgG2a | Yes | − | − | | | |
| 4F9.1E8.1C2 (S/N) | 2760 | hu PSCA-E Coli * | Balb/C | IgG2a | Yes | ++ | ++ | | ND | |
| 6B8.1D7.2B3 | 2761 | hu PSCA-E Coli * | Balb/C | IgG2a | Yes | ++ | +++ | B | Yes | Yes |
| 3F9.1D4.2F1(S/N) | 2759 | gDPSCA-CHO | Balb/C | IgG1 | Yes | ++ | − | A | ND | |
| 2B12.1H6.1F9 (S/N) | 2758 | gDPSCA-CHO | Balb/C | IgG1 | Yes | ++ | + | A | ND | |
| 2 parental S/N | | gDPSCA-HCT116 cells | Balb/C | IgM | | + | | | | |
| pending | | gDPSCA-HCT116/formalin | Balb/C | | | | | | | |
| pending | | gDPSCA-HCT116 cells | Xenomice | | | | | | | |
| no titers | | prk5.hu PSCA (cDNA) | Balb/C | | | | | | | |
| 10C5.6E4.6D1(S/N) | 2910 | hu PSCA-E coli | Xenomice | IgG2 | Yes | ++ | + | | | |
| N/A | | hu PSCA-E coli * | Xenomice | | | | | | | |
| pending | | muPSCA-E. coli | Lewis rats | | | | | | | |
| pending | | gDmuPSCA-PC3 cells | Lewis rats | | | | | | | |

ND = not determined
Asc# = Ascites #
IHC = immunohistochemistry
hu PSCA = human PSCA
* nonrefolded huPSCA
S/N = supernatant
IP = intraperitoneal
FP = via footpad
muPSCA = murine PSCA

Example 2

This example demonstrated the binding and localization of anti-PSCA antibodies 2395 (6F8), 2399 (8D11), 2403 (5F2), 2761 (6B8) [ascites number followed by antibody no. in parenthesis; see Table 2B] to PSCA expressing tumor cells (MCF-7Her2gdPSCA and HCT-gdPSCA) in vivo. By labeling antibodies with the fluorescent dye, Cy3, antibody binding can be visualized by fluorescence microscopy. This technology was well established using Cy3 labeled Herceptin (anti-Her2 monoclonal antibody) in mice bearing Her2-expressing tumors. In vivo binding of the anti-PSCA antibodies were tested on tumor cells transfected with human gd-linked PSCA. Control antibodies included Cy3 labeled Herceptin as a positive control for the MCF-7Her2gdPSCA cells. Additionally, a Cy3 labeled anti-gd antibody, with very good binding activity, was used as a positive control for the PSCA antibodies. Transfected PSCA is gd linked, thus the level of gd protein directly correlates with PSCA protein expression. Cell lines not transfected with gdPSCA were used as negative controls.

I. Materials and Methods

Cell Lines

HCT-116 (ATCC CCL-247) is a human colon tumor cell line; HCT-47 is a PSCA expressing clone derived from transfecting the parental HCT-116. MCF-7 (ATCC HTB-22; Soule, D. G. et al., *J. Natl. Cancer Inst.*, 51:1409-1416, 1973) is a human breast tumor cell line which was previously transfected with and expresses Her2 (Benz et al. *Breast Cancer Research and Treatment* 24: 85-95 (1992)). PC3 (ATCC CRL-1435) is a human prostatic carcinoma cell line (Kaign et al. Invest. Urol., 17: 16-23, 1979). These cells were transfected with human PSCA (huPSCA) or with gD-huPSCA. gD or gd refers to the Herpes Simplex virus glycoprotein D epitope tag. In the construction of gD-huPSCA, the signal sequence of PSCA was replaced with the sequence encoding the gD epitope tag; the gD-PSCA sequence was cloned into pRK vector. Her2 expression on the cell surface served as a control since Her2 antibody (HERCEPTIN®) is known to be able to localize to Her2-expressing tumor cells in vivo. From these transfections, human PSCA-expressing tumor cells were obtained.

Antibody Preparation

Refer to Table 2B for a list of the murine monoclonal anti-PSCA antibodies used in these experiments. The antibody names are derived from the first 3-4 characters of the clone producing the antibody. All antibodies were labeled using FluoroLink Cy3 monofunctional dye (Amersham Pharmacia, PA23001) according to the manufacturer's directions. Antibodies for the labeling reaction were in 0.1 M Sodium Carbonate pH 9.3 at a concentration of 1 mg/ml. One ml of the 1 mg/ml of antibody stock was added to the tube with Cy3 labeling mix, mixed thoroughly, and allowed to incubate at room temperature for 30 min on a shaker. Samples were wrapped in tin foil to reduce light exposure. NAP 10 columns (Amicon) were equilibrated with PBS and when the conjugation reaction was done, the reaction solution was added to the column. 1.5 ml PBS were added and the flow through was collected. Spectrophotometer readings were taken at A552 and A280. Protein concentration and dye to protein ratios were calculated as follows:

AB concentration: $\{[A280-(0.08 \times A552)] \times \text{dilution factor}\}/1.4 = \text{mg/ml}$ Dye to Protein ratio: $[1.13 \times (A552)]/[A280-(0.08 \times A552)]$ After labeling, all antibodies were checked for binding by FACS analysis (see Table 2B).

Tumor Inoculations and Growth

NCR nude female mice were implanted with Estrogen pellets and then inoculated subcutaneously with 20 million cells of MCF-7Her2gdPSCA or 20 million cells of non-transfected MCF-7 cell line as a negative control. Male NCR nude mice were inoculated subcutaneously with 5 million HCT-gdPSCA cells. The tumors are injected subcutaneously, so they are situated on the flank of the mouse. Using a caliper with a digital read out, tumor measurements were taken twice weekly until tumor volume reached 100 to 500 mm$^3$.

Cy3 Antibody Injection and Tissue Collection

Once tumors reached at least 150 mm$^3$ in volume, mice were injected IP with 10 mg/kg of one of the three Cy3 labeled anti-PSCA antibodies (6F2, 8D11, 5F2), a Cy3 anti-gd antibody, or Cy3 labeled HERCEPTIN. Twenty four hours later, mice were anesthetized and perfused with 1% paraformaldehyde. Tumor tissue and other organs were collected and frozen in OCT (Tissue-Tek O.C.T. Compound, Sakura Finetek U.S.A. Inc., Torrance Calif. 90504) cryoprotectant for antibody localization by fluorescence microscopy. Similar experiments were also carried out with Cy3 labeled 6B8 antibody.

Fluorescence Microscopy

Frozen samples were sectioned into 5 um sections and fluorescent mounting media with dapi (Vectastain) was applied. Dapi stains nuclei and provides a counterstain.

II. Results

TABLE 3

Antibody Preparations and FACS Analysis

| ANTIBODY | dye/protein (D/P) ratio | Post-labeling FACS analysis |
|---|---|---|
| 2395 (6F8) | 4 | shift |
| 2399 (8D11) | 4 | shift |
| 2403 (5F2) | 3 | shift |
| Herceptin (4D5) | 5 | shift |
| anti-gd (952) | 5 | shift |

To confirm that Cy3 labeling of the antibodies did not negatively affect their ability to bind antigen, the antibodies were tested for their binding specificity on cells by FACS analysis. In Table 3 "shift" refers to a shift in the cell population when screened for fluorescence and indicates that the Cy3 labeled antibodies maintain their abilities to bind their specific antigen.

TABLE 4

Summary of Antibody Localization

| ANTIBODY | MCF-7Her2gdPSCA Tumors staining positive | MCF-7 Tumors staining positive |
|---|---|---|
| 2395 (6F8) | 3 (n = 4) | 0 (n = 3) |
| 2399 (8D11) | 2 (n = 2) | 0 (n = 2) |
| 2403 (5F2) | 3 (n = 4) | 0 (n = 3) |
| Herceptin (4D5) | 2 (n = 2) | 0 (n = 2) |
| anti-gd(952) | 2 (n = 2) | 0 (n = 2) |

| ANTIBODY | HCT-gdPSCA Tumors staining positive |
|---|---|
| 2395 (6F8) | 1 (n = 1) |
| 2399 (8D11) | 2 (n = 2) |

The results summarized in Table 4, demonstrated that the anti-PSCA antibodies were able to specifically localize and bind to PSCA-expressing tumor cells in vivo. No staining was detected in the lung or the kidney. Cy3 staining was observed in the liver for all PSCA antibodies, anti-gd, and Herceptin in what are most likely phagocytic Kupffer cells that have taken up the antibody. Non-malignant cells associated with the tumors, most likely macrophages, were also seen to stain positive for Cy3 for all antibodies on both the transfected and non-transfected cell lines. Additionally, antibody 6B8 was also shown to localize to PCSA-expressing PC-3 tumor cells but not on control-transfected PC3 tumor cells in vivo. The staining pattern was primarily membranous. Positive staining was also observed in macrophages in and adjacent to the tumor.

Example 3

This example describes the ability of the anti-PSCA monoclonal antibodies of the invention, to be internalized by PSCA-expressing cells. These studies were performed using fluorescent or radiolabeled antibodies or antibodies with gold adducts. With the radiolabeled antibodies, quantitation of the amount of antibody internalized in each cell line was analyzed.

I. Materials and Methods

In Vitro studies

Transfected cells expressing gD PSCA (HCT-47 and PC3-19 cells) and MCF7cells expressing PSCA/HER2 (also referred to herein as MCF7/PSCA/HER2 cells) were grown on coverslips, incubated with a series of monoclonal anti-PSCA antibodies (10 µg/mL) for one hour (hr), washed in PBS, fixed in 3% PBS buffered formaldehyde, permeabilized with 1% Triton in PBS and labeled with Cγ3-fluorescent labeled anti-mouse IgG. In control experiments, parental, untransfected cells were used. Immunolabeled cells were observed in a Molecular Dynamics confocal microscope.

For electron microscopy, transfected NIH-3T3 expressing gD-PSCA were incubated at 4° C. with 25 ug/ml of anti-gD antibody for one hr. In another set of experiments, CHO cells expressing PSCA were incubated at 4° C. with 20 µg/ml of 10E3 and 6C3 anti-PSCA antibodies. Following incubation with primary antibodies, the cells were treated with 10 nm gold adducts of goat anti-mouse IgG for one hour. The cells were switched to 37° C. for 15 min and 1 hr before fixation in Karnovsky's fixative, and processed for electron microscopy. Thin sections were observed in a Philips CM12 equipped with a digitizing GATAN camera.

For electron microscopy autoradiography, 10A1 and 8D11 anti-PSCA antibodies were iodinated according to the manufacturer's instructions for Iodo-Gen. $^{125}$I-10A1 and $^{125}$I-8D11 anti-PSCA antibodies were incubated for 15 min, 1 hr and 6 hr with HCT116 gD PSCA cells (human colon tumor cell line transfected with gD human PSCA, described above). After incubation, the cells were washed and fixed in 2% formaldehyde, 2.5% glutaraldehyde in 0.1M cacodylate buffer pH 7.2 and postfixed in 1% osmium tetroxide. After dehydration and embedding in EPONATE 12 epoxy resin, thin sections were cut, coated with Ilford L4 emulsion. After exposure, the sections were developed in Microdol X, stained with uranyl acetate and lead citrate, and observed in a Philips CM12 electron microscope.

Internalization of 6B8 anti-PSCA antibody was studied by electron microscopy using PC3 cells expressing gD.huPSCA. 6B8 antibodies were iodinated according to manufacturer's instructions for Iodo-Gen. $^{125}$I-6B8 antibodies were incubated for 15 min and 24 hr with PC3.gD.huPSCA clone4 cells. After incubation, the cells were washed and fixed with 2% formaldehyde, 2.5% glutaraldehyde in 0.1M cacodylate buffer pH 7.2 and postfixed with 1% osmium tetroxide. After dehydration and embedding in EPONATE 12 epoxy resin, thin sections were cut and coated with Ilford 1.4 emulsion. After exposure, the sections were developed in Microdol X, stained with uranyl acetate and lead citrate, and observed in a Philips CM 12 electron microscope.

A steady state internalization study was performed as follows: MCF7/Her2 cells (FIG. 11, right panel) are transfected with vector alone containing the puromcyin selectable marker (PurR); this cell line served as negative control for internalization of the PSCA antibodies. MCF7/Her2/gD.PSCA cell line is described in Example 2. MCF7/Her2 and MCF7/Her2/gD.PSCA cells were incubated with one of the following antibodies for 5 hours at 37° C.: 22 nM $^{125}$I labeled anti-PSCA monoclonal antibodies 2395, 2399, 2403, and 0.8 nM $^{125}$I labeled anti-Her2 antibody, Herceptin. Unbound antibody was removed and the cells were washed with cold medium. The amount of radioactivity bound to the cells was determined by incubating the cells in Acid Wash (2M Urea, 0.5M Nacl, 50 mM Glycine pH2.4) for 10 minutes and then removing and counting the wash. The cells were then solubilized with Lysis Buffer (8M Urea, 3M glacial acetic acid) and the resulting lysates counted to determine the amount of radioactivity internalized. Using the specific activity of the radio-labeled antibodies and the number of cells in each assay sample, cpm were converted to molecule/cell.

In Vivo Studies

MCF7/HER2/PSCA xenograft tumor bearing mice were dosed IP with Cγ3 labeled 6F8, 5F2, or 8D11 PSCA antibodies. After 24 hrs, the tumors were removed and cryosectioned at 5, 10, 20 and 50 µm and observed by confocal microscopy.

Anti-PSCA antibodies are labeled with $^{125}$I as described for the in vitro experiment above. MCF-7/Her2/gdPSCA cells are prepared and inoculated into NCR nude mice and $^{125}$I labeled anti-PSCA antibodies, a $^{125}$I-anti-gd antibody, or $^{125}$I labeled HERCEPTIN® are injected into the mice as described in Example 2 above. Tumor cells are sectioned for analysis.

II. Results

In the in vitro studies, confocal microscopy of immunolabeled HCT 47 gD PSCA, PC3-19 gD PSCA and MCF7/HER2/PSCA cells showed that these cells bind and internalize the following anti-PSCA monoclonal antibodies, 8D11, 10A1, 6C3, 6F8, 5F2, 7A6 and 10E3 to varying extents (See FIGS. 5-8). Internalization staining pattern was characterized by the presence of cytoplasmic vesicles and perinuclear organelles likely to correspond to the endosomes in proximity of the Golgi apparatus.

In the in vivo study, labeling can be seen on the cell surface of most of the cryosectioned cells and internalized into small vesicles near the cell surface in a small percentage of the cells.

EM internalization studies using the above-described 3T3 cells incubated with anti-gD antibodies visualized with 10 nm gold particles indicated that gD-PSCA was internalized and transported to the endosomal compartment. Gold particles were visualized in calveolae and multivesicular bodies. EM internalization studies using PSCA-transfected CHO cells also showed that the same pathway was involved in the internalization of both 10E3 and 6C3 antibodies (see FIG. 9A-9D). The kinetics of PSCA internalization appeared to be rapid (15 min from the plasma membrane to the endosomes).

Figure 10:
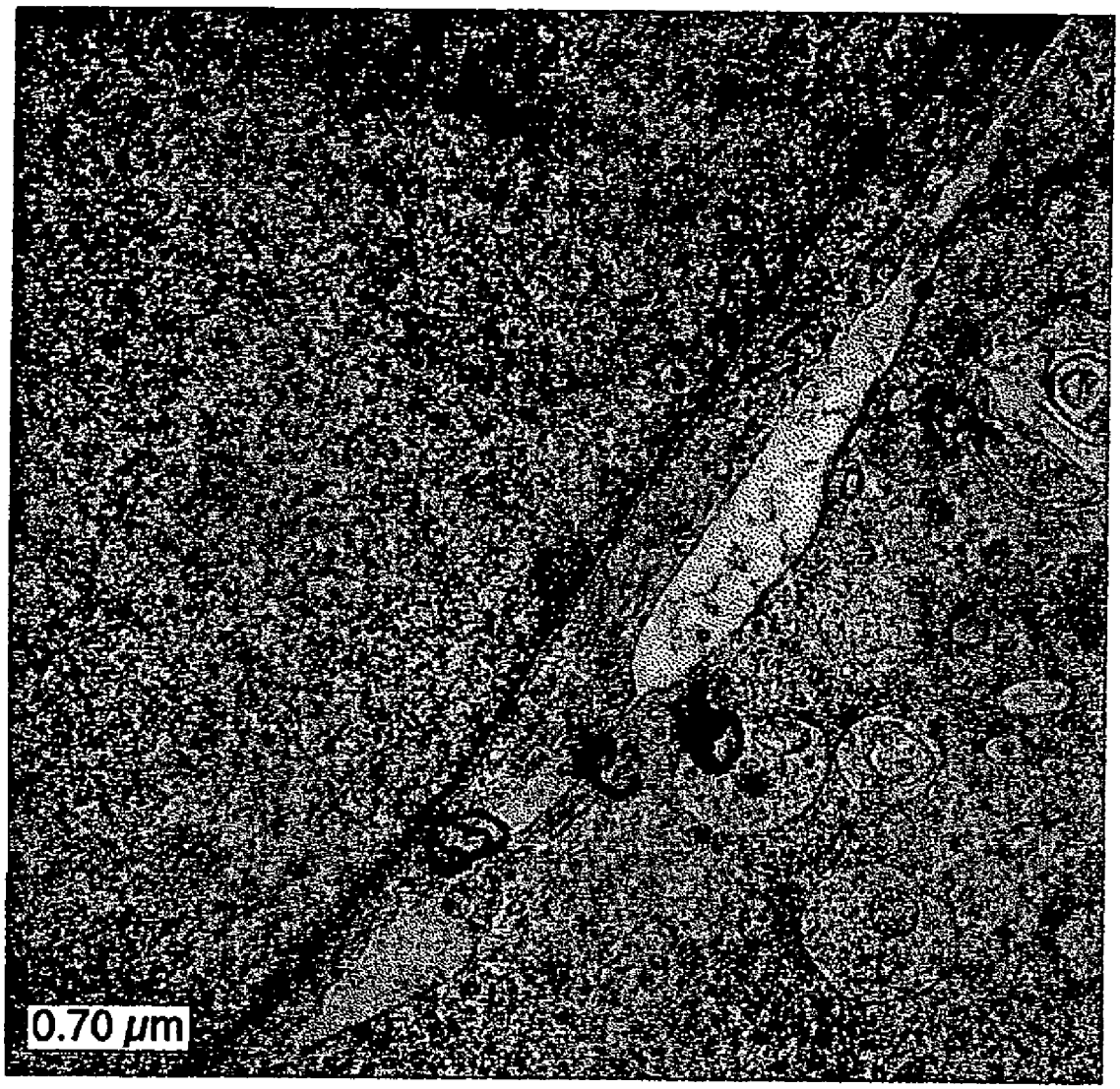
FIG. 10 is a micrograph showing internalization of $^{125}$I-8D11 antibody in HCT116 gDPSCA cells 15 minutes after contact with the antibody (see Example 3 below).

With $^{125}$I-10A1 and $^{125}$I-8D11 anti-PSCA antibodies, autoradiographic silver grains were observed associated with the cell membrane, particularly with the microvilli. Autoradiographic grains were also seen internalized within the cells as early as 15 minutes after addition of the $^{125}$I-labeled 10A1 and 8D11 antibodies. The internalization seen in the micrograph of FIG. 10 is representative of the results of this experiment. Control HCT116 cells transfected with neo marker but not PSCA, showed no internalization.

The results with the 6B8 antibody were similar to those obtained with $^{125}$I-10A1 anti-PSCA antibody. Internalization of antibody 6B8 was observed by 15 minutes, continuing through the 24-hour time-point. Autoradiographic grains were first observed associated with the caveolae of the cell membrane and later internalized in the endosomes.

Figure 11:
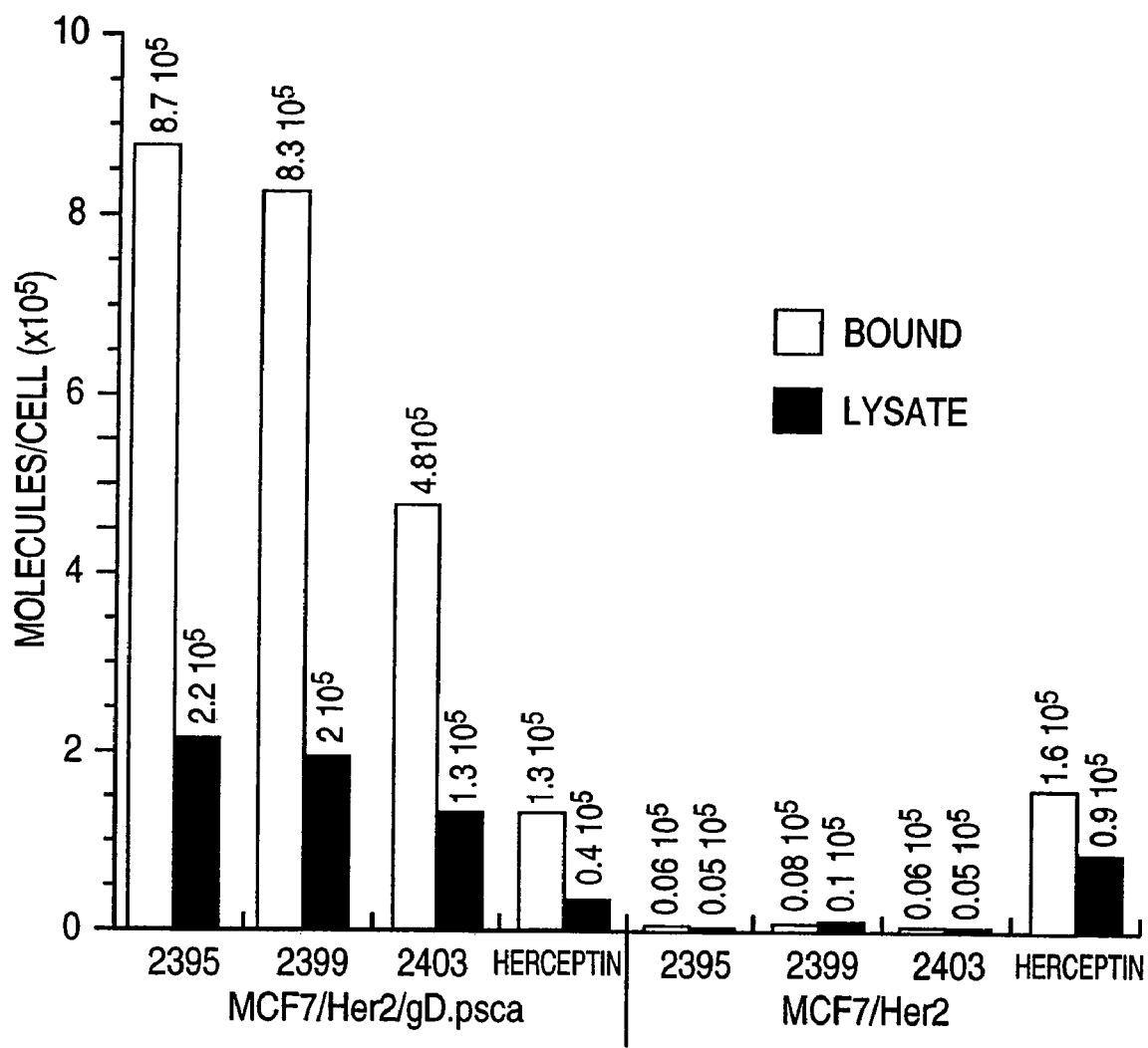
FIG. 11 shows the levels of internalization of three anti-PSCA antibodies [ascites # 2395 (6F8), #2399 (8D11), #2403 (5F2)] at 37° C. after 5 hours, in Her2-expressing MCF7 cells transfected with either gD-PSCA or vector alone (see Example 3 below). Herceptin, is an anti-Her2 antibody.

FIG. 11 shows the steady state levels of internalization of three anti-PSCA antibodies [ascites no. 2395 (6F8), 2399 (8D11), 2403(5F2)] at 5 hours in Her2-expressing MCF7 cells transfected with gD-PSCA. Herceptin served as a control antibody. The number of molecules of anti-PSCA antibodies per cell bound versus free in the lysate, was quantitated.

III. Conclusion

The antibodies directed against PSCA (6C3, 10E3, 10A1, 6F8, 5F2, 8D11, 6B8) were efficiently endocytosed and internalized both in vivo and in vitro. Ultrastructural analysis indicated that the internalization of 6C3, 10E3 and 6B8 likely takes place via calveolae. The antibodies accumulate in multivesicular bodies in close proximity to the Golgi apparatus. Thus, by different approaches, the anti-PSCA antibodies of the invention were shown to be internalized upon binding to PSCA on the cell surface.

Example 4

Figure 14:
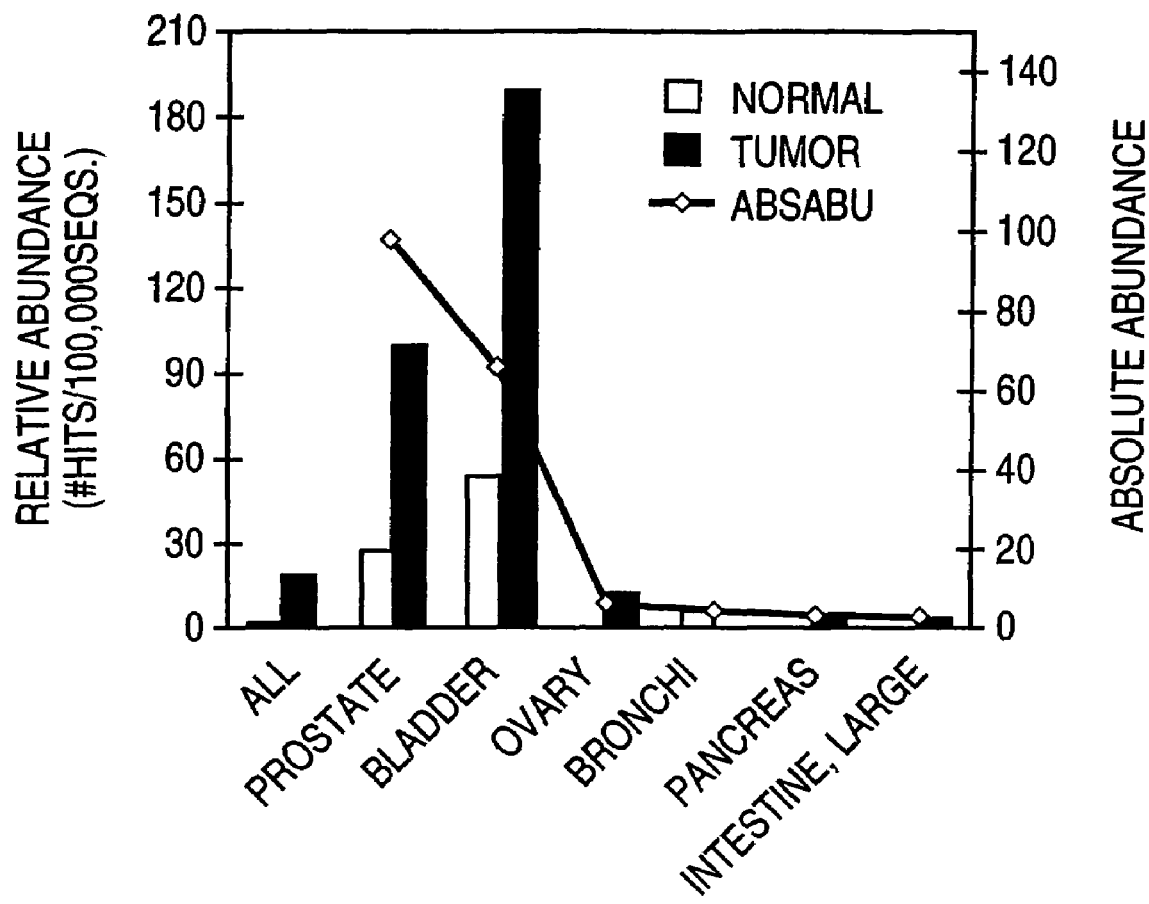
FIG. 14 shows a comparison of the relative expression levels of PSCA in various tumor versus normal tissues (see Example 4).

The abundance of PSCA in various normal and tumor tissues was assessed by determining from a database of cDNA libraries, the number of copies of the PSCA nucleotide sequence present in cDNA libraries representing genes expressed in different tissues and organs (see FIG. 14). For each organ indicated in FIG. 18 (x-axis), pools of several dozen cDNA libraries are represented. "All" means a mixture of the cDNA libraries representative of the different organs indicated in the figure, as well as cDNA libraries prepared from various tissues including bone, uterus, small intestine, thymus, stomach, connective tissue and unclassified tissue type. The relative abundance in normal and tumor organs is determined by the number of copies of the PSCA sequence in the pooled library divided by the total number of sequences in that pooled library and is represented in FIG. 14 as #hits/100,000 random sequences. From the absolute abundance (Absabu), it is clear that PSCA expression is highly upregulated in prostate and bladder tumors.

Example 5

The anti-tumor activity of the anti-PSCA antibodies was assessed in vivo.

I. Materials and Methods

The human prostate cancer cell line, PC3, was obtained from the ATCC (ATCC CRL-1435). The cell line PC3.gDhuPSCA subclone was obtained by transfecting the parental PC3 line with pRK.gDPSCA.tkneo using the Fugene method (Roche Molecular Biochemical) and plating in 400 ug/ml G418 (Life Technologies). After two weeks of growth, G418 resistant sub-clones were selected, expanded and assayed for gDPSCA expression. The cell line PC3.Neo was made by transfecting the parental PC3 line with the vector pRK.tkneo and selection in 400 ug/ml G418. Stable colonies were pooled and expanded.

Figure 18:
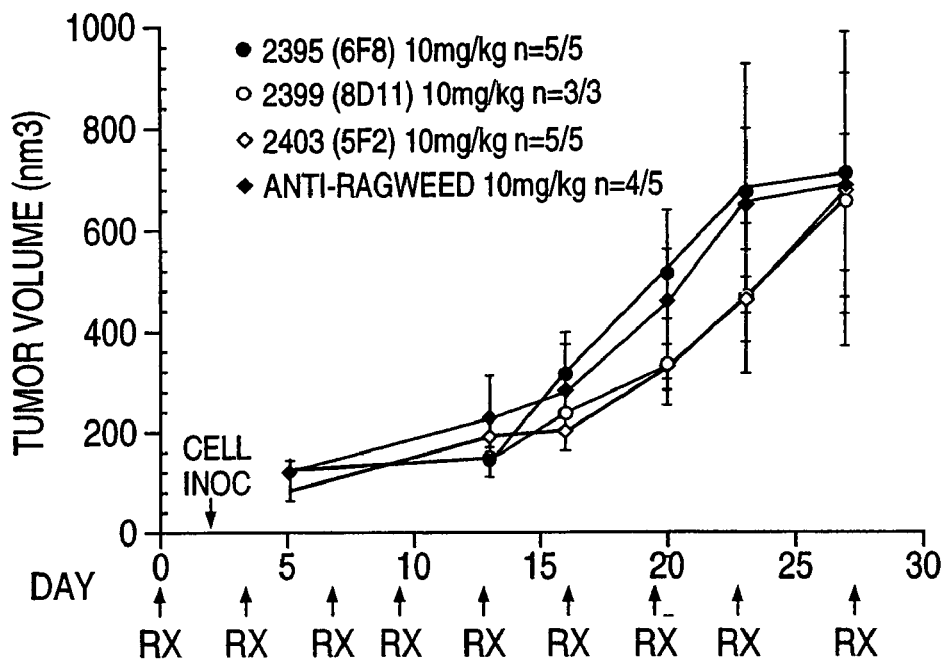
FIG. 18 shows the growth of control PC-3 tumor cells (PSCA-negative) in mice treated with 3 of the anti-PSCA antibodies (6B8, 8D11, and 5F2) as compared to the anti-ragweed negative control antibody (see Example 5).
Figure 19:
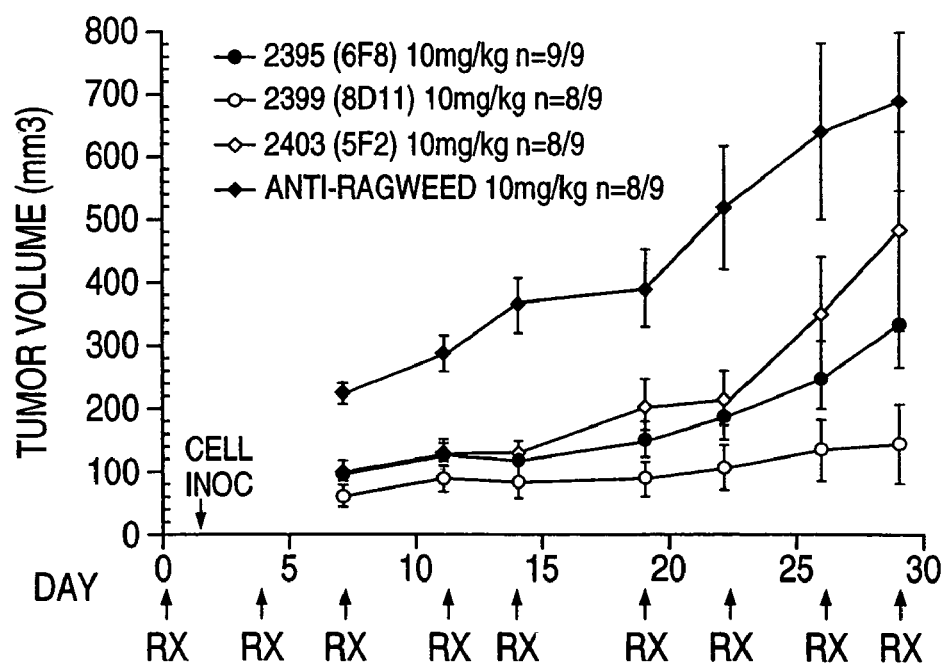
FIG. 19 shows the growth of PC-3.gDPSCA tumors in mice treated with 3 of the anti-PSCA antibodies (6F8, 8D11, and 5F2) as compared to the negative control, anti-ragweed antibody. The antibodies were administered by intraperitoneal injection starting one day prior to inoculation with PSCA-transfected PC-3 cells, followed by biweekly injections following cell inoculation. "RX" under the arrows indicates the time point (day) of injection of the antibodies into the mice (see Example 5).
Figure 20:
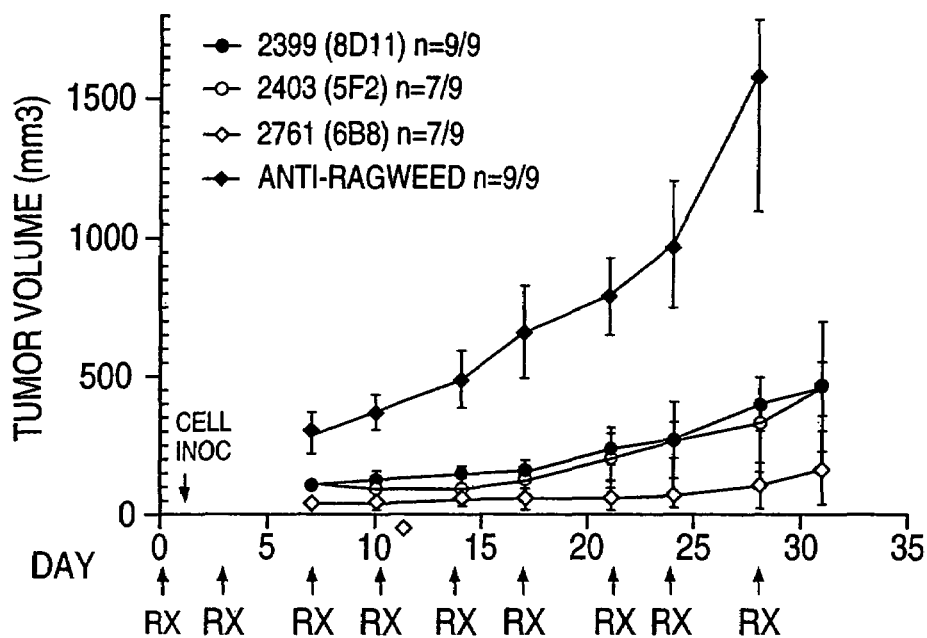
FIG. 20 shows the growth of PC-3.gDPSCA tumors treated with antibodies 8D11, 5F2, 6B8 and control ragweed antibodies, as described in FIG. 19 (see Example 5).

NCR nude mice (Taconic, Germantown, N.Y., USA) were injected subcutaneously with $5\times10^6$ gDPSCA transfected PC-3 cells or neo transfected PC-3 cells. Anti-PSCA monoclonal antibodies 2395 (6F8), 2399 (8D11), 2403 (5F2), and 2761 (6B8) were administered intraperitoneally by injection at a dose of 10 mg/kg one day prior to cell inoculation. As a negative control, an anti-ragweed monoclonal antibody, MARG2 (Genentech), was administered by the same dosing regimen. Following cell inoculation, animals were treated biweekly with 10 mg/kg antibody. Tumor measurements were taken biweekly. The results of these experiments are shown in FIGS. 18-20.

Figure 21:
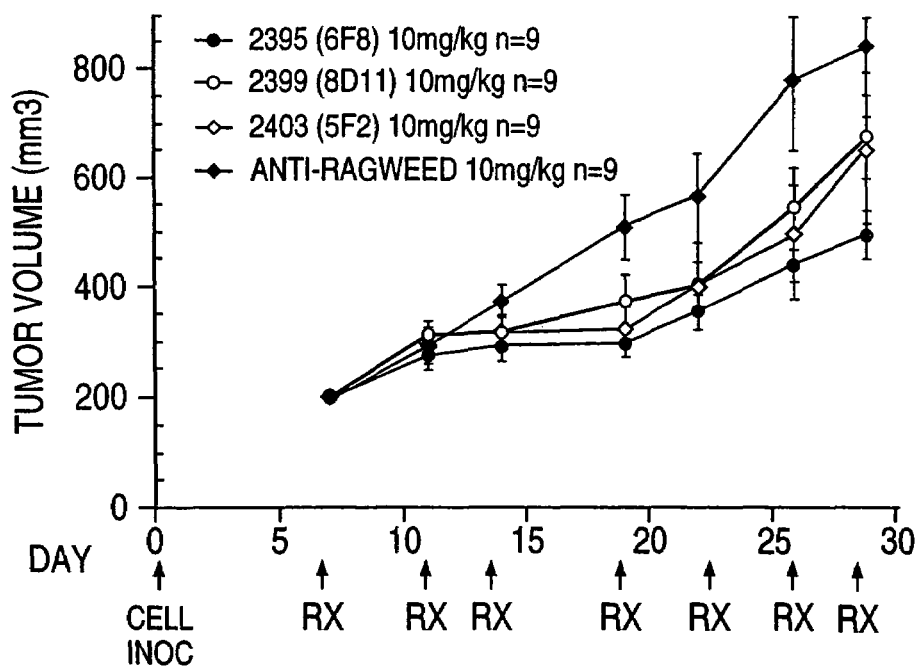
FIG. 21 shows the growth of PC-3.gDPSCA tumors in mice wherein treatment with anti-PSCA antibodies 6F8, 8D11, or 5F2 was initiated after the tumors had been allowed to grow for 1 week in the mice and had reached a mean tumor volume of approximately 200 mm$^3$ per group of mice. Antibody administration was biweekly. "RX" under the arrows indicates the time point (day) of intraperitoneal injection of the antibodies into the mice (see Example 5).

In a separate experiment (posttreatment), tumors were allowed to establish to a certain size before the mice were treated with anti-PSCA antibody, mimicking the condition and treatment in prostate cancer patients. Optimally, the tumor size should be approximately 75-100 mm$^3$ before antibody treatment. In this experiment, the NCR nude mice (Taconic, Germantown, N.Y., USA) were injected subcutaneously with $5\times10^6$ gDPSCA transfected PC-3 cells and tumors were allowed to grow for 1 week. Mice were then grouped into four groups of nine mice, each group with a mean tumor volume of approximately 200 mm$^3$. The mice were then treated biweekly with 10 mg/kg anti-PSCA monoclonal antibodies 2395 (6F8), 2399 (8D11), 2761 (6B8), and 2403 (5F2) or anti-ragweed, MARG2 (Genentech). Tumor measurements were taken biweekly. The results of these experiments are shown in FIG. 21.

II. Results

The four anti-PSCA antibodies tested, i.e., 2395 (6F8), 2399 (8D11), 2403 (5F2), and 2761 (6B8), showed cytotoxic activity as naked (unconjugated) antibodies in killing the PSCA-expressing prostate cancer cells in vivo (see FIGS. 19-21), compared to the control ragweed antibody. The p values were significantly different from the control group at p<0.05 for 2395 and 2399 in FIG. 19, 2399, 2403 and 2761 in FIG. 20, and 2395 in FIG. 21. Tumoricidal activity was specific to PSCA expressing tumor cells (FIGS. 19-21) and absent in the control, PSCA-negative PC3 tumor cells (FIG. 18). It was difficult to predict or control the growth rate of the PC3 tumor cells once injected into the mice, to timely initiate the antibody treatment. As a result, in these initial posttreatment experiments, the tumors were at a bigger (150-200 mm$^3$) than optimum size (75-100 mm 3) at the time of administration of the anti-PSCA antibody. Greater efficacy in tumor cytotoxicity can be expected if treatment with anti-PSCA antibody is initiated at a time when the tumor is smaller and of a more representative size and if the antibody dose was increased above 10 mg/kg.

Example 6

Cynomolgus Monkey PSCA

This example describes the cloning of the Cynomolgus monkey PSCA and shows that the present anti-human PSCA antibodies bind the highly homologous Cynomolgus PSCA and human PSCA with similar affinities. In addition to the high homology, we have found that Cynomolgus urothelium expresses PSCA in a manner that is identical to that observed for human urothelium, thus making this primate a good and appropriate animal model for anti-PSCA antibody toxicity studies. Naked and toxin-conjugated anti-PSCA antibodies will be tested in this model.

I. Materials and Methods

Cloning of Cynomolgus PSCA

RNA was purified from one cynomolgus monkey bladder. To clone PSCA, RT-PCR was performed using primers psca.2F (AAGGCTGTGCTGCTTGCCCT—SEQ ID NO:

14) and psca.1R (GAGTGGCACAAAGGCCTGGG—SEQ ID NO: 15). The resulting PCR products from two independent PCR reactions were subcloned into the PCR subcloning vector pCR2.1-TOPO (Invitrogen) and then sequenced.

Affinity Measurements on Cell Surface PSCA

The entire coding sequence for human and for Cynomolgus PSCA were cloned into an expression vector, pRK. Anti-PSCA monoclonal antibody 5F2 (ascites no. 2403) was labeled with $^{125}$I using the lactoperoxidase method. PC3 cells or CHO cells were transiently transfected with either pRK.gD.human psca or pRK.gD.cynomolgus psca using Fugene Reagent (Roche). After 2 days of transfection, the cells were replated in a 24 well dish and incubated in medium with various concentrations of unlabeled Mab 2403 and a constant amount of $^{125}$I-Mab 2403 for 16 hours at 4° C. Unbound antibody was removed and cells were washed with ice-cold medium. The amount of radioactivity bound was determined by solubilizing the cells in 8M Urea/3M glacial acetic acid. The Kd value was calculated by scatchard analysis using the NewLigand program.

FACS Analysis:

COS Cells (African green monkey kidney cells) were transiently transfected with either vector pRK.human.psca or pRK.cynomolgus.psca. Two days after transfection, cells were removed from the culture dishes with 5 mM EDTA and washed 1× with PBS. Cells were divided into several tubes and stained at 4° C. for one hour with 10 ug/ml antibody 8D11 (ascites #2399) or 6B8. After washing 2× with PBS, cells were stained with FITC anti-mouse (ICN) antibodies and then analyzed using flow cytometry. Xenomouse antibodies (from 10C5 subclones 1D8, 3B8 and 6D1) were used at 100 ul of hybridoma supernatant per reaction and were stained with FITC anti-human Kappa chain antibodies and again analyzed by flow cytometry. The results of the FACS analysis are shown in Table 5 below.

II. Results

Seven subclones of the monkey PSCA were sequenced from which two types of sequences were obtained: type 1 (4 subclones) and type II (3 subclones). The DNA and translated amino acid sequences are shown in FIG. 15 for type I (SEQ ID NO. 16 & 17) and FIG. 16 for type II (SEQ ID NO. 18 & 19). As RNA was purified from an individual monkey bladder and the monkey was from the wild (not an inbred strain), these two types most likely represent different alleles of the same gene. Type I and Type II Cynomolgus PSCA show 98.64% identity at the DNA level, and 99.18% identity at the protein level with only a single amino acid difference the two, at amino acid 119 (Ser vs. Gly). PSCA is a GPI-anchored surface protein. In human PSCA, the cleavage position for GPI attachment is at amino acid 100. Assuming that cleavage and GPI-linkage occurs at a similar position in Cynomolgus PSCA, the mature type I and type II monkey PSCA would be 100% identical in amino acid sequence. Both types show approximately 94% identity to human PSCA across the entire coding sequence. FIG. 17 compares the amino acid sequence of human (SEQ ID NO. 1) and Cynomolgus Type I PSCA (SEQ ID NO.17).

The mean FACS shifts (indicated in units of FITC) for anti-PSCA antibodies on human or Cynomologus PSCA expressed in COS Cells are shown in Table 5 (for murine antibodies) and Table 6 (for Xenomouse antibodies). It was known from other studies that the 5F2, 8D11 and 6F8 antibodies have very similar binding affinities for human PSCA. Therefore, of these 3 antibodies, 5F2 was used as a representative in the cold competition assay. Table 7 compares the affinities of antibodies 5F2 and 6B8 for cell surface human and Cynomolgus PSCA as determined by cold competition assay. The results from PC3 and CHO transfected cells were similar. The results from FACS analysis and cold competition assay indicated that the murine and xenomouse human antibodies bound human and cynomolgus PSCA that was expressed in its native context on the cell surface, with equivalent affinity (within the margin of error).

TABLE 5

| | Mean FACS Shifts | | |
|---|---|---|---|
| | no Mab | 8D11 | 6B8 |
| human | 4.2 | 22.6 | 11 |
| cynomolgus | 3.9 | 21.9 | 10 |

TABLE 6

| | Mean FACS Shifts | | | |
|---|---|---|---|---|
| | no Mab | 1D8 | 3B8 | 6D1 |
| human | 3.6 | 10 | 9.6 | 14.3 |
| cynomolgus | 3.8 | 10.9 | 12.3 | 14.4 |

TABLE 7

Antibody Affinity for Cell Surface PSCA

| anti-psca mab | PSCA species | cell line | Kd |
|---|---|---|---|
| 5F2 | human | PC3.gD.hu.psca clone 4 | 13.2 |
| 5F2 | cynomolgus | PC3.cyn.psca clone 8 | 7 |
| 6B8 | human | PC3.gD.hu.psca clone 4 | 21 |
| 6B8 | cynomolgus | PC3.cyn.psca clone 8 | 3.3 |

Example 7

Anti-PSCA Antibody—DM1 Conjugation

Figure 22:
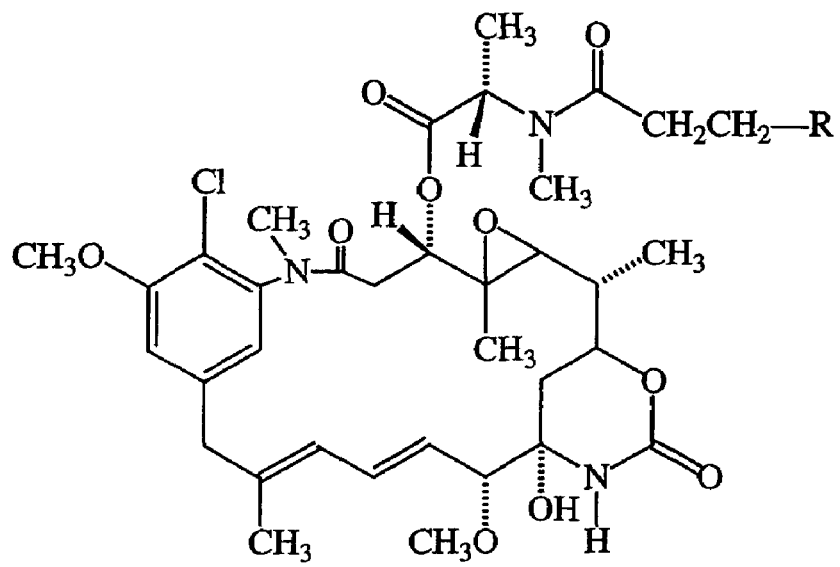
FIG. 22 shows the structure of the maytansinoid designated "DM1" (see Example 7).
Figure 23:
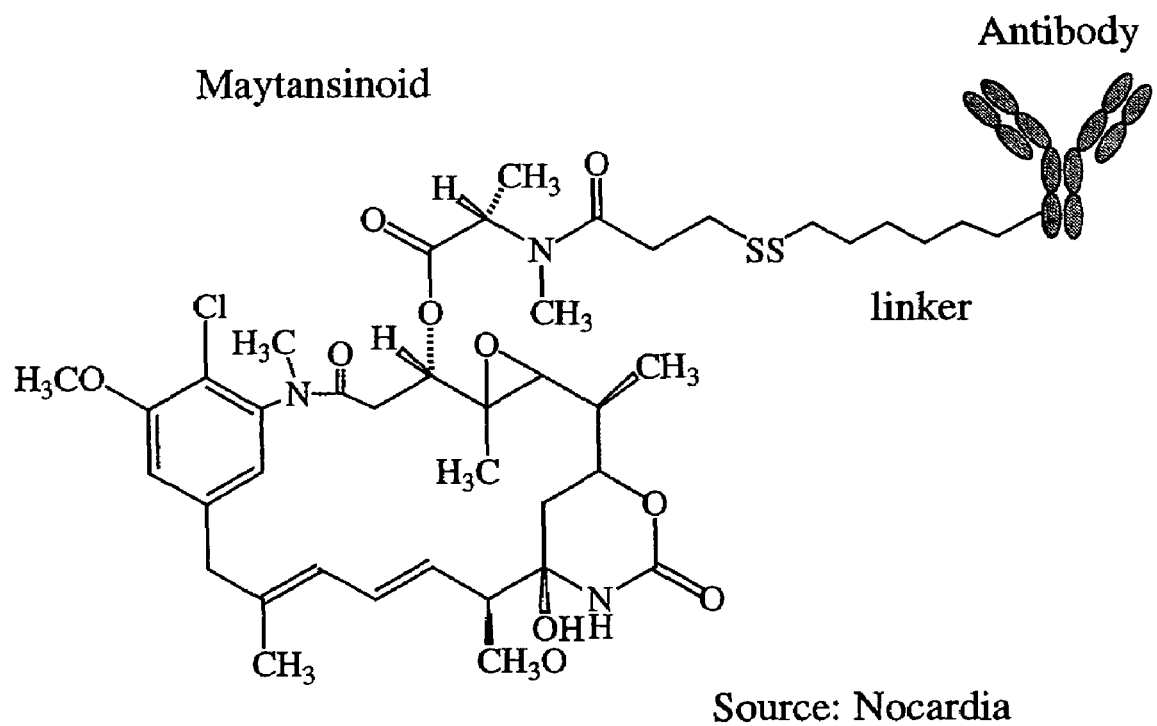
FIG. 23 illustrates the structure of anti-PSCA antibody-DM1 conjugate (see Example 7).

This example describes the conjugation of an anti-PSCA antibody to the maytansinoid, DM1. DM1 is a prodrug that gets activated in the cell; it is a potent inhibitor of microtubule formation and disrupts mitosis. The structure of DM1 is shown in FIG. 22. The structure of anti-PSCA antibody-DM1 conjugates is illustrated in FIG. 23. For the following conjugation, the R group in FIG. 22 is SH or a protected derivative thereof; particularly preferred is a disulfide derivative. Modifications may be made to this protocol, e.g., to optimize the pH or concentrations of reagents for individual antibodies; these modifications are routine in nature and will be familiar to a protein chemist of skill in the art.

Modification of Anti-PSCA Antibody with SPP

A purified anti-PSCA antibody (e.g., one of the anti-PSCA antibodies listed in Table 2B) is modified with N-succinimidyl-4-(2-pyridylthio)pentanoate (SPP) to introduce dithiopyridyl groups. The antibody (e.g., at about 6-10 mg/mL) in potassium phosphate buffer (PPB; e.g., 50 mM PPB at pH 6.5) containing NaCl (50 mM) and EDTA (1 mM) is treated with SPP (e.g. at 5.3 molar equivalents in 2.3 mL ethanol). After incubation for 90 minutes under argon at ambient temperature, the reaction mixture is filtered following standard procedures e.g., by gel filtration through a Sephadex G25 column equilibrated with 35 mM sodium citrate, 154 mM NaCl, 2 mM EDTA. Antibody containing fractions are pooled and assayed. The degree of modification of the antibody is determined as described above.

Conjugation of Anti-PSCA Antibody-SPP-Py with DM1

The modified antibody (e.g., with 9.5 μmols of releasable 2-thiopyridine groups) is diluted with the above 35 mM sodium citrate buffer, pH 6.5, to a final concentration of e.g., 2.5 mg/mL. DM1 (e.g., at 1.7 equivalents, 16.1 μmols) in 3.0 mM dimethylacetamide (DMA, 3% v/v in the final reaction mixture) is then added to the antibody solution. The reaction proceeded at ambient temperature under argon for 20 hours.

The reaction is loaded on a gel filtration column, e.g., Sephacryl S300 gel filtration column (5.0 cm×90.0 cm, 1.77 L) equilibrated with 35 mM sodium citrate, 154 mM NaCl, pH 6.5. The flow rate is at e.g., 5.0 mL/min and 65 fractions (20.0 mL each) are collected. The major peak comprises monomeric anti-PSCA antibody-DM1. Fractions around the major peak are pooled and assayed. The number of DM1 drug molecules linked per antibody molecule is determined, e.g., by measuring the absorbance at 252 nm and 280 nm, and found to be around 3-5 drug molecules per antibody molecule.

Example 8

Cytotoxicity of Anti-PSCA-DM1 Conjugates on Cultured Cells

Figure 24:
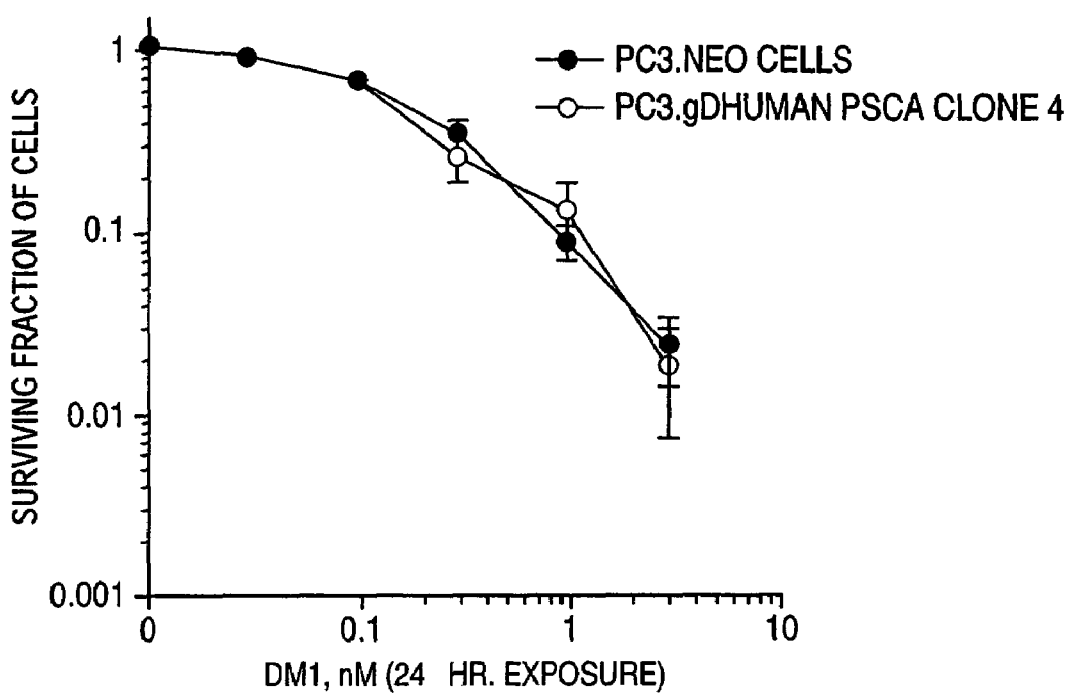
FIG. 24 shows the sensitivity of assay cell lines, PC3.Neo cells and PC3.gD human PSCA clone 4 cells, to non-conjugated DM1 (see Example 8).

Anti-PSCA antibodies #2761 (6B8) and #2399 (8D11) were conjugated to DM1 as described above. From the internalization studies, it was expected that the DM1 antibody conjugates should be efficiently taken up by PSCA expressing cells. Two anti-ragweed antibodies were used as controls for antigen specificity and immunoglobulin isotype. The results for the in vitro cytotoxicity of the first four DM1 conjugates are reported. Cytotoxicity was measured in clonogenic assays on PC3.Neo cells and PC3.gD human PSCA clone 4 cells. These two cell lines were shown to be equally sensitive to the non-conjugated DM1 (FIG. 24), suggesting that PC3.Neo cell line was a good antigen-negative control for the PC3.gDhuman PSCA clone 4 cells.

I. Method

Cells were plated in 6-well tissue culture grade plates in growth medium that contained or did not contain the antibody conjugate to be tested. Control cultures were plated at 500 cells/plate. Cultures that were exposed to the conjugate were plated at several densities between 500 and 5000 cells/well. The cells were then incubated at 37° C. for 5 to 7 days to allow colony formation. The cells were fixed, stained with Crystal violet dye, and the colonies were scored. Plating efficiency (PE) was calculated as the number of colonies/number of cells plated. Surviving fraction was calculated as PE of treated cells/PE of non-treated cells. Plating efficiencies of control cultures were in the range of 40 to 60% for both the control and the PSCA-expressing cell line.

II. Results: (Concentrations are Given as Those for the Respective Antibodies)

| Conjugate | Reference # | Isotype | DM1/Ab | $IC_{10}$, M |
|---|---|---|---|---|
| Anti-PSCA antibody #2761-DM1 | 1461-44 | $IgG_{2a}$ | 3.39 | $\sim 1 \times 10^{-9}$ |
| Anti-PSCA antibody #2399-DM1 | 1461-165 | $IgG_{2b}$ | 2.94 | $\sim 3 \times 10^{-10}$ |
| Anti-Ragweed antibody #1428-DM1 | 1461-154 | $IgG_{2a}$ | 2.68 | not toxic |
| Anti-Ragweed antibody #1429-DM1 | 1461-175 | $IgG_{2b}$ | 1.85 | not toxic |

Figure 25:
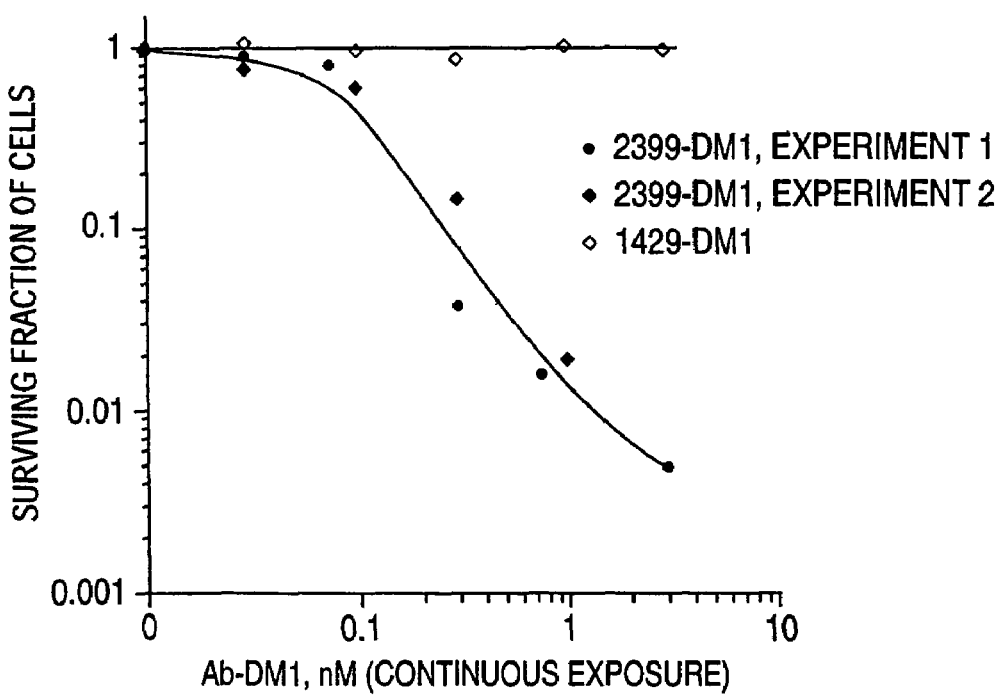
FIG. 25 shows the cytotoxicity of antibody conjugate 2399-DM1 to PC3.gDhuman PSCA clone 4 cells compared to isotype control 1429-DM1 (see Example 8).
Figure 26:
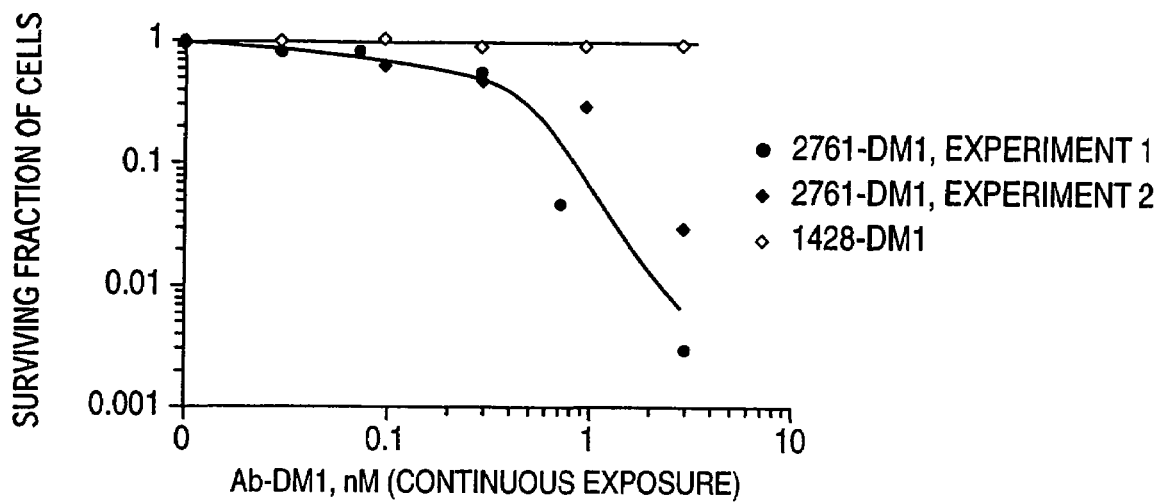
FIG. 26 shows the cytotoxicity of 2761-DM1 to PC3.gDhuman PSCA clone 4 cells compared to isotype control 1428-DM1 (see Example 8).
Figure 27:
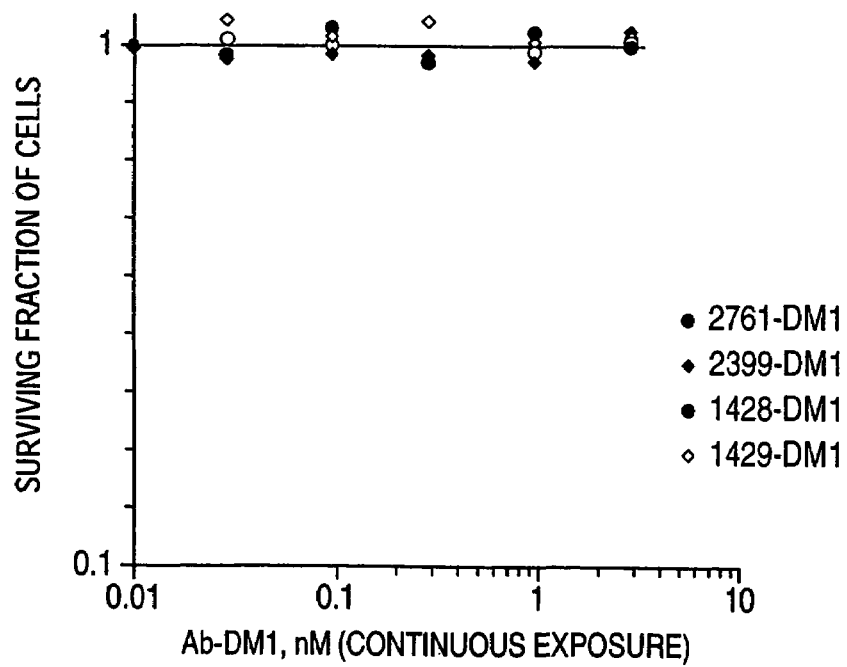
FIG. 27 shows the lack of toxicity of antibody-DM1 conjugates in antigen-negative PC3.Neo cells (see Example 8).

Antibody conjugate 2399-DM1 was cytotoxic for PC3.gDhuman PSCA clone 4 cells with an $IC_{10} \sim 3 \times 10^{-10}$ M, continuous exposure (FIG. 25). An isotype-matched control, 1429-DM1 was not toxic for the cells up to the highest concentration tested ($3 \times 10^{-9}$ M). The second conjugate, 2761-DM1, was cytotoxic for PC3.gDhuman PSCA clone 4 cells with an $IC_{10} \sim 1 \times 10^{-9}$ M, continuous exposure (FIG. 26). An isotype-matched control, 1428-DM1 was not toxic for the cells up to the highest concentration tested ($3 \times 10^{-9}$ M). None of the four antibody-DM1 conjugates were toxic for PC3.Neo cells up to the highest concentration tested ($3 \times 10^{-9}$ M), see FIG. 27.

Conclusion

Antibody conjugates 2399-DM1 and 2761-DM1 were specifically cytotoxic towards the PSCA antigen-positive cells.

Example 9

Effect of Antibody-DM1 Conjugates on Tumor Growth In Vivo

I. Materials and Methods

Female NCR nude mice (Taconic, Inc.) 6-8 weeks of age were injected with $5 \times 10^6$ PC-3gdPSCA cells subcutaneously in a volume of 0.2 ml on Day 1. Tumors were allowed to grow for 5 days and then were measured in two dimensions using a caliper. Tumor volume was expressed in $mm^3$ using the formula: $V=0.5 a \times b^2$, where a and b are the long and the short diameters of the tumor, respectively. Mice were grouped into 6 groups of 7 mice with a mean tumor volume of 160 $mm^3$. On Day 6, antibody treatments were started. Naked (non-DM1 conjugated) anti-PSCA antibodies 2399 (8D11), 2761 (6B8) and the anti-Ragweed negative control antibody, 1428, were injected intraperitoneally (IP) twice a week at a dose of 10 mg/kg. This treatment regimen was continued through out the experiment. The same antibodies conjugated to the maytansinoid cytotoxin, DM1, were injected intravenously (IV) at a concentration of 75 ug/kg of DM1. DM1 antibodies were administered twice a week for a total of 8 doses. Tumors were measured twice a week through out the experiment. Table 8 below shows the dosing regimen.

TABLE 8

| Group | Antibody | DM1 dose | AB dose | Schedule |
|---|---|---|---|---|
| 1 | 2399-naked IP | N/A | 10 mg/kg | 2 × week entire duration |
| 2 | 2761-naked IP | N/A | 10 mg/kg | 2 × week entire duration |
| 3 | Anti-Ragweed Naked (1428) IP | N/A | 10 mg/kg | 2 × week entire duration |
| 4 | 2399-DM1 IV | 75 ug/kg | 5.5 mg/kg | 2 × week 8 total doses |
| 5 | 2761-DM1 IV | 75 ug/kg | 5 mg/kg | 2 × week 8 total doses |
| 6 | Anti-ragweed-DM1(1428) IV | 75 ug/kg | 6.1 mg/kg | 2 × week 8 total doses |

Results

Figure 28:
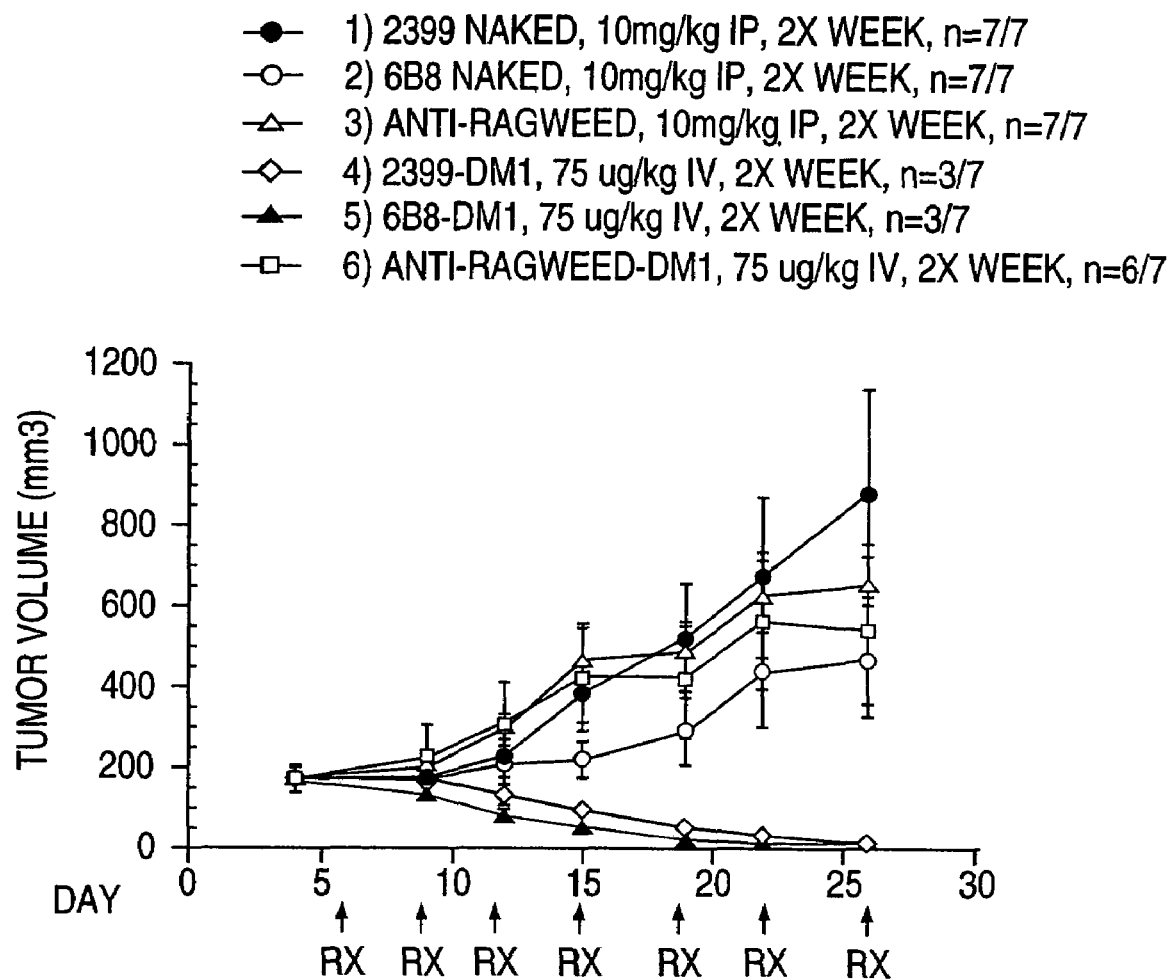
FIG. 28 shows the growth of PSCA-expressing, PC3 human prostate tumor cells in a mouse model in which the mice were treated with either naked (non-toxin conjugated) antibody or DM1-conjugated antibody. The anti-PSCA antibodies were 2399 or 6B8 and the anti-ragweed antibody 1428 serves as the control antibody (see Example 9).

As shown in FIG. 28, by day 26 of treatment, the human prostate tumors (PSCA-expressing cells) were virtually eliminated in the animals treated with DM1-conjugated anti-PSCA antibodies (2399 and 2761) compared to both the non-conjugated anti-PSCA antibodies and the DM1-antiragweed control antibody. Within each group of 7 animals treated with DM1-2399 or DM1-2761, four of the animals had no detectable tumor. For the three animals with remaining tumor, the average tumor size was just 6 mm$^3$ compared to a tumor volume of about 550 mm$^3$ for the DM1-ragweed control antibody group. DM1 treatments will continue for one more dose ending on day 29. On day 33, mice from all groups are sacrificed and tumor tissues are collected for histological analysis. Other tissues including liver, kidney and bladder are collected and examined for evidence of cytotoxicity related to antibody treatments.

Example 10

PSCA Expression Analysis Using Tissue Microarray

The expression of human PSCA in normal tissues and malignant tumors was investigated using isotopic in-situ hybridization (ISH) on multi-tissue arrays. A tissue microarray (TMA) is a paraffin block which typically contains between one hundred to more than one thousand individual tissue samples. TMAs are constructed by taking small biopsy samples from "donor" tissues embedded in paraffin blocks and re-embedding the biopsies together in a single "recipient" block to form an array.

I. Method

PCR primers (upper-5' ACC CAC GCG TCC GGC TGC TT 3' [SEQ ID NO. 24] and lower-5' CGG GGG ACA CCA CGG ACC AGA 3' [SEQ ID NO. 25]) were designed to amplify a 768 bp fragment of human PSCA. Primers included extensions encoding 27-nucleotide T7 or T3 RNA polymerase initiation sites to allow in vitro transcription of sense or antisense probes, respectively, from the amplified products. Tumor microarray slides were deparaffinized, deproteinated in 20 µg/ml of proteinase K for 15 minutes at 37° C., and further processed for in situ hybridization. $^{33}$P-UTP labeled sense and antisense probes were hybridized to the sections at 55° C. overnight. Unbound probe was removed by incubation in 20 mg/ml RNase A for 30 min at 37° C., followed by a high stringency wash at 55° C. in 0.1×SSC for 2 hours and dehydration through graded concentrations of ethanol. The slides were dipped in NBT2 nuclear track emulsion (Eastman Kodak), exposed in sealed plastic slide boxes containing desiccant for 4 weeks at 4° C., developed and counterstained with hematoxylin and eosin.

II. Results

The results of the ISH assay for normal prostate and prostate tumors are as summarized in Table 9.

TABLE 9

| | In-situ Hybridization | | |
|---|---|---|---|
| Tissue | Negative | Weakly Positive | Strongly Positive |
| Normal Prostate (n = 29) | 55% | 28% | 17% |
| Normal Urothelium (n = 4) | 0% | 25% | 75% |
| Primary Prostate Cancer (n = 97) | 48% | 27% | 25% |
| Metastatic Prostate Cancer (n = 28) | 22% | 39% | 39% |

The group of primary prostate cancer contains seven cases of prostatic intraepithelial neoplasia (PIN; one case is negative, one case is weakly positive and five cases are strongly positive for PSCA). The group of metastatic prostate cancers consists of 25 cases of lymph node metastases, two cases of liver metastases (both cases are strongly positive for PSCA) and one case of a brain metastasis (weakly positive for PSCA). Preliminary results on an additional prostate multi-tissue array (normal prostate, primary and metastatic prostate cancer) confirm these numbers. The results for other tumor types (lung and colon) are preliminary and appear to indicate that approximately 10% of lung tumors and 5% of colon tumors express PSCA at a weak or moderate level.

Example 11

PSCA Distribution in Tumors and Normal Tissue

Example 11 describes the distribution of PSCA in tumors and normal tissue as evaluated by immunohistochemistry (IHC) using the anti-PSCA mabs herein. A series of primary, organ-confined prostate cancers is evaluated for expression of PSCA. The expression of PSCA is also assayed in frozen sections of breast, lung, colon and kidney tumors, and in colon carcinoma cell lines. Separately, Taqman™ analysis for PSCA is being performed on some of the same cases used for this IHC study. TaqMan™ is a fluorescent PCR-based technique which makes use of the 5' exonuclease activity of Taq DNA polymerase enzyme to monitor gene amplification in real time.

Staining Procedure for PSCA on Frozen Sections

Five micron thick frozen sections are cut from fresh frozen tumor tissue on a Leica cryostat and stored at −20° C. until further use.

Sections are dried thoroughly and fixed in Acetone/Ethanol for 5 minutes. They are then rinsed twice with phosphate-buffered saline (PBS), for 5 minutes each. Endogenous peroxidase activity is quenched using the glucose oxidase/glucose method at 37° C. for 60 minutes. This is followed by rinses with PBS, 2 changes for 5 minutes each. Blocking for endogenous biotin is done using Vector Avidin/Biotin Blocking Kit. Blocking for endogenous immunoglobulin binding sites is done with 10% normal horse serum for 30 minutes. Blocking serum is not washed off.

The sections are incubated with anti-PSCA murine antibody at 10 ug/ml diluted in blocking serum for 60 minutes at room temperature (RT). A mouse isotype control antibody (Zymed) is used for negative control. The sections are rinsed with PBS twice for 5 minutes each. The detection of specifically bound primary antibody is accomplished with biotinylated horse anti-mouse Ig. The sections are incubated with diluted biotinylated horse anti-mouse IgG 1:200 in blocking serum for 30 minutes. The sections are rinsed with PBS twice for 5 minutes each, incubated with diluted ABC reagent for 30 minutes and again rinsed with PBS twice for 5 minutes each. Sections are incubated with Pierce Metal Enhanced DAB for 5 minutes, then rinsed with tap water for 5 minutes, counterstained with Mayer's hematoxylin for 1 minute, rinsed with water, transferred into 70%, 95% and 100% Ethanol, followed by xylene and coverslipped. The sections are then dehydrated, cleared and mounted in synthetic mounting media.

Results

PSCA expression in malignant epithelial cells is seen. The level of expression ranges from weak to very strong, the proportion of malignant cells positive ranges from less than 10% to >95%. PSCA mRNA has previously been demonstrated in a case of colorectal adenocarcinoma by in-situ hybridization.

Example 12

Animal models are useful for understanding pathogenetic mechanisms and for the development of novel therapeutics. This study reports the pattern of expression of the murine PSCA in fetal and adult tissues by in situ hybridization, as well as a murine model for human prostate adenocarcinoma.

Structurally, PSCA is a GPI-linked membrane glycoprotein with homology to members of the Thy-1/Ly-6 family of proteins. It is most closely related to Sca2, a cell surface maker for immature lymphocytes (Noda S. et al. Journal of Experimental Medicine 1996; 183:2355-60). Expression of human PSCA RNA in normal tissues was originally described not only as tissue specific, but essentially limited to prostatic basal cells. The authors inferred from this latter observation and from the structural homology to Sca2 that PSCA may represent a "stem" cell antigen.

The murine homologue has been shown to demonstrate 70% identity to human PSCA at the nucleotide and the amino acid level. (Reiter R E et al., 1998, Proc. Nat. Acad. Sci. 95:1735-40). One well established animal model for human prostate cancer is the Transgenic Adenocarcinoma of the Mouse Prostate™ (TRAMP™) (Greenberg N M, 1995, PNAS 92:3439-43). Though there are significant anatomical differences in the mouse prostate compared to that of the human, there are inherent common characteristics including secretory function and hormonal regulation. In the TRAMP™ model, the minimal promoter of the rat probasin gene targets expression of the SV40 large T-antigen to the prostatic epithelium. All male TRAMP mice progress to prostate cancer usually by 8-12 weeks (Gingrich J R et al., 1997, Cancer Research 57:4687-91). The autochthonous TRAMP™ model is particularly relevant to human prostate carcinoma in that the development of the cancer is specific to the prostatic epithelium and is initially regulated by androgens. Furthermore, metastases to distant sites eventually occur (Gingrich J R et al., 1996, Cancer Research 56:4096-102; Gingrich J R et al., 1999, Prostate Cancer & Prostatic Diseases 2:70-75).

I. Materials and Methods

Mice and Tissue Collection

Male and female adult CD-1 mice between the ages of 10 and 24 weeks were obtained form Charles River laboratories. Pregnant mice were ordered for the collection of embryos. The day of isolation with copulatory plug was considered day 1 of embryonic development. Fetal tissues examined by ISH included: E10, E13, E14, E15, E17 and E18. Adult tissues examined included: tissues of the male urogenital system, female urinary bladder and kidney, pubescent mammary gland, 14 day pregnant mammary gland, lactating mammary gland, liver, heart, skin and intestine. All tissues were fixed in 4% formalin and paraffin-embedded. Breeder pairs of TRAMP™ transgenic mice were obtained from Dr. Norman Greenberg (Baylor College of Medicine, Houston, Tex.). Urogenital tissues from wild type litter mate C57BL/6 were taken at age 12 and 24 for comparison to age matched TRAMP™ transgenic mice. By the age of 12 weeks, TRAMP™ mice have typically progressed to PIN and or well differentiated tumors. Nine TRAMP™ male mice between the ages of 12 to 39 weeks of age were sacrificed and tissues were collected for routine histology and ISH studies. The histological grade of prostate cancer was determined as according to previously published studies in the TRAMP™ model (Gingrich J R et al., 1999, Prostate Cancer & Prostatic Diseases 2:70-75).

Cloning of the Murine PSCA Orthologue

Full-length cDNA for murine PSCA was amplified from mouse 17-day embryo Marathon-Ready cDNA (Clontech). Primers were designed based on EST sequences present in Genbank. Sense primer (5' ACT ATG AAG CTT TGC AGC TCA TCC CTT CAC AAT CG 3' (SEQ ID NO. 20)) and anti-sense primer in the 3' untranslated region (5' GAA TTC GGA TCC ACC ATG AAG ACC GTC TTC TTT CTC CTG CTG 3' (SEQ ID NO. 21)) were used resulting in a 420 bp fragment that was subsequently cloned into the PCR subcloning vector PCR2.1TOPO (Invitrogen). Clones were confirmed by DNA sequencing.

In Situ Hybridization

PCR primers (upper-5' CCT GCT GGC CAC CTA CT 3' and lower-5' CCT TCA CAA TCG GGC TAT 3'-SEQ ID NOs. 22 & 23, respectively) were designed to amplify a 388 bp fragment of murine PSCA. Primers included extensions encoding 27-nucleotide 17 or T3 RNA polymerase initiation sites to allow in vitro transcription of sense or antisense probes, respectively, from the amplified products (Lu et al. Cell Vision 1994, 1:169-176). Five µm thick sections were deparaffinized, deproteinated in 4 µg/ml of proteinase K for 30 minutes at 37° C., and further processed for in situ hybridization. $^{33}$P-UTP labeled sense and antisense probes were hybridized to the sections at 55° C. overnight. Unbound probe was removed by incubation in 20 mg/ml RNase A for 30 minutes at 37° C., followed by a high stringency wash at 55° C. in 0.1 X SSC for 2 hours and dehydration through graded concentrations of ethanol. The slides were dipped in NBT2 nuclear track emulsion (Eastman Kodak), exposed in sealed plastic slide boxes containing desiccant for 4 weeks at 4° C., developed and counterstained with hematoxylin and eosin. The in situ hybridization was routinely performed on duplicate sections with sense and antisense probes. No significant hybridization signal was observed on sections hybridized with the sense probe.

Results

In summary of the results, murine PSCA is expressed during fetal development in the urogenital sinus, skin and gastrointestinal tract. The expression in these tissues is restricted to the most superficial cell layer. In the adult mouse, expression is highest in the mucosal lining of the urinary tract. In the normal adult prostate, expression of PSCA is detected exclusively in the secretory epithelium. Examination of PSCA during carcinogenesis of the murine prostate in the TRAMP™ model showed a markedly increased expression in areas of neoplasia.

These studies demonstrate that expression of murine PSCA is neither prostate specific or consistent with it being a stem cell marker. The results clearly indicate that PSCA expression in epithelial surfaces is restricted to the adluminal or superficial cell layer and not, as reported for the human gene, to basal cells. Cells of the adluminal outer layer typically display a high degree of differentiation, but unlike stem cells, low proliferative or self-renewal capability. The designation of this molecule as a "stem cell antigen" is therefore questionable. These results suggest that the pattern of expression of murine PSCA in normal tissues and in tissues of murine prostatic adenocarcinoma is different from published data on human prostate adenocarcinomas. Most likely, the differences in PSCA expression between the TRAMP™ tumors and human prostatic adenocarcinoma either indicate species-specific regulation of PSCA expression or are related to the type of carcinogenic event at play.

The strongest expression of PSCA is detected in the urothelium of the developing and mature urinary tract. In the adult organism the expression appears continuous from the renal pelvis throughout the urethra. Prostatic expression is patchy, but increases noticeably at the juncture of the large prostatic ducts and urethra. It is tempting to speculate, whether this finding is related to urinary reflux into these structures providing a potential clue to the function of this protein. A common feature of the epithelial surfaces exhibiting PSCA expression is the fact that they line structures which are in continuous contact with fluids, mucous or secretions. This is obviously the case for urothelium, however, this notion also holds true for the observation that significant PSCA expression is present in the amniotic membrane, anal canal, oropharynx, esophagus and skin of the developing fetus. Not to be limited by any one hypothesis or mechanism, it is likely that additional denominators are at play, because other fluid-exposed epithelial tissues such as the fetal tracheobronchial tree, do not express PSCA. Whether the expression in fetal skin is temporally regulated is difficult to determine at this point as the number of embryos evaluated is small. However it appears that expression of PSCA in skin is no longer required in postnatal, extrauterine life. The pattern of expression within multilayered epithelial surfaces suggests that PSCA may function as a barrier or buffer against external insults. Further studies, such as the generation of PSCA knockout mice would be helpful to clarify the primary function of PSCA in normal tissue.

The rather selective expression of PSCA in fetal and adult tissues makes the mouse a suitable model to determine the physiologic function of this protein. Though PSCA is lost in the advanced tumor stages, the TRAMP™ model may still represent a potentially useful tool to study PSCA as a target for prostate cancer.

Conclusion

The working examples above demonstrated that the anti-PSCA antibodies of the invention effectively targeted PSCA-expressing cancer cells in vivo and that the GPI-linked PSCA molecule and the antibody bound to it were rapidly internalized upon the binding of the antibody to a PSCA-expressing cancer cell. The anti-PSCA antibodies showed specificity and efficacy in tumor cell killing and arresting tumor growth in vivo. Cytotoxicity of the tumor cells was greatly enhanced using toxin-conjugated antibody, specifically the maytansioid, DM1, which is a toxin that acts intracellularly. Treatment with DM1-conjugated anti-PSCA antibody completely eliminated the PSCA-expressing, human prostate tumor cells in vivo (see Example 9).

IX. References

References cited within this application, including patents, published applications and other publications, are hereby incorporated by reference.

The practice of the present invention will employ, unless otherwise indicated, conventional techniques of molecular biology and the like, which are within the skill of the art. Such techniques are explained fully in the literature. See e.g., *Molecular Cloning: A Laboratory Manual*, (J. Sambrook et al., Cold Spring Harbor Laboratory, Cold Spring Harbor, N.Y., 1989); *Current Protocols in Molecular Biology* (F. Ausubel et al., eds., 1987 updated); *Essential Molecular Biology* (T. Brown ed., IRL Press 1991); *Gene Expression Technology* (Goeddel ed., Academic Press 1991); *Methods for Cloning and Analysis of Eukaryotic Genes* (A. Bothwell et al. eds., Bartlett Publ. 1990); *Gene Transfer and Expression* (M. Kriegler, Stockton Press 1990); *Recombinant DNA Methodology II* (R. Wu et al. eds., Academic Press 1995); *PCR: A Practical Approach* (M. McPherson et al., IRL Press at Oxford University Press 1991); *Oligonucleotide Synthesis* (M. Gait ed., 1984); *Cell Culture for Biochemists* (R. Adams ed., Elsevier Science Publishers 1990); *Gene Transfer Vectors for Mammalian Cells* (J. Miller & M. Calos eds., 1987); *Mammalian Cell Biotechnology* (M. Butler ed., 1991); *Animal Cell Culture* (J. Pollard et al. eds., Humana Press 1990); *Culture of Animal Cells*, $2^{nd}$ Ed. (R. Freshney et al. eds., Alan R. Liss 1987); *Flow Cytometry and Sorting* (M. Melamed et al. eds., Wiley-Liss 1990); the series *Methods in Enzymology* (Academic Press, Inc.); Wirth M. and Hauser H. (1993); *Immunochemistry in Practice*, 3rd edition, A. Johnstone & R. Thorpe, Blackwell Science, Cambridge, Mass., 1996; *Techniques in Immunocytochemistry*, (G. Bullock & P. Petrusz eds., Academic Press 1982, 1983, 1985, 1989); Handbook of Experimental Immunology, (D. Weir & C. Blackwell, eds.); *Current Protocols in Immunology* (J. Coligan et al. eds. 1991); Immunoassay (E. P. Diamandis & T. K. Christopoulos, eds., Academic Press, Inc., 1996); Goding (1986) *Monoclonal Antibodies: Principles and Practice* (2d ed) Academic Press, New York; Ed Harlow and David Lane, *Antibodies A laboratory Manual*, Cold Spring Harbor Laboratory, Cold Spring Harbor, N.Y., 1988; *Antibody Engineering*, $2^{nd}$ edition (C. Borrebaeck, ed., Oxford University Press, 1995); and the series Annual Review of Immunology; the series Advances in Immunology.

X. Deposit of Cell Lines and DNA

The following hybridoma cell lines were deposited with the American Type Culture Collection (ATCC), located at 10801 University Boulevard, Manassas, Va. 20110-2209, U.S.A., and accorded the accession numbers:

| Hybridoma | ATCC Accession No. | Deposit Date |
|---|---|---|
| PSCA.10E3 | PTA-717 | Sep. 16, 1999 |
| PSCA.6F8 | PTA-718 | Sep. 16, 1999 |
| PSCA.8D11 | PTA-719 | Sep. 16, 1999 |
| PSCA.5F2 | PTA-720 | Sep. 16, 1999 |
| PSCA.6C3 | PTA-880 | Oct. 26, 1999 |
| PSCA.6B8 | PTA-2265 | Jul. 25, 2000 |
| PSCA.10C5 | PTA-2264 | Jul. 25, 2000 |

The folowing vector DNAs (see Example 1) were deposited with the ATCC

| pRK-2403L | PTA-2623 | Oct. 24, 2000 |
|---|---|---|
| pRK-2761L | PTA-2621 | Oct. 24, 2000 |
| pRK-2403H | PTA-2622 | Oct. 24, 2000 |
| pRK-2716H | PTA-2620 | Oct. 24, 2000 |

The names of the deposited hybridoma cell lines above have been shortened for convenience of reference; these hybridomas correspond to the clones (with their full names) listed in Table 2B.

This deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S.

Commissioner of Patents and Trademarks to be entitled thereto according to 35 USC §122 and the Commissioner's rules pursuant thereto (including 37 CFR §1.14 with particular reference to 8860G 638).

The assignee of the present application has agreed that if the cultures on deposit should die or be lost or destroyed when cultivated under suitable conditions, they will be promptly replaced on notification with a viable specimen of the same culture. Availability of the deposited strains are not to be construed as a license to practice the invention in contravention of the rights granted under the authority of any government in accordance with its patent laws. The making of these deposits is by no means an admission that deposits are required to enable the invention.

What is claimed is:

1. A method of killing a PSCA-expressing cancer cell, comprising contacting the cancer cell with an isolated PSCA antibody that internalizes upon binding to PSCA on a mammalian cell in vivo, wherein the antibody is a humanized form of the antibody produced by a hybridoma selected from the group of hybridomas having ATCC accession number PTA-718, PTA-719, PTA-720, PTA-880, or PTA-2265, and wherein the cancer cell is selected from the group consisting of prostate cancer, bladder cancer and lung cancer cell.

2. The method of claim 1, wherein the prostate cancer is androgen independent.

3. The method of claim 1, wherein the cancer cell is from metastatic prostate cancer.

4. The method of claim 1, wherein the antibody is conjugated to a cytotoxic agent.

5. The method of claim 4, wherein the cytotoxic agent is a toxin selected from the group consisting of maytansinoid or calicheamicin.

6. The method of claim 5, wherein the cytotoxic agent is a maytansinoid.

7. The method of claim 4, wherein the cytotoxic agent is a radioactive isotope.

* * * * *